US012570719B2

(12) United States Patent
Chae et al.

(10) Patent No.: US 12,570,719 B2
(45) **Date of Patent: *Mar. 10, 2026**

(54) CHIMERIC ANTIGEN RECEPTOR COMPRISING ANTI C-MET ANTIBODY OR ANTIGEN BINDING FRAGMENT THEREOF, AND USE THEREOF

(71) Applicant: HELIXMITH CO., LTD, Seoul (KR)

(72) Inventors: Jin-A Chae, Seoul (KR); Seung Shin Yu, Seoul (KR)

(73) Assignee: HELIXMITH CO., LTD, Seoul (KR)

( * ) Notice: Subject to any disclaimer, the term of this patent is extended or adjusted under 35 U.S.C. 154(b) by 1021 days.

This patent is subject to a terminal disclaimer.

(21) Appl. No.: 17/763,712

(22) PCT Filed: Sep. 25, 2020

(86) PCT No.: PCT/KR2020/013127
§ 371 (c)(1),
(2) Date: Mar. 25, 2022

(87) PCT Pub. No.: WO2021/060932
PCT Pub. Date: Apr. 1, 2021

(65) Prior Publication Data
US 2022/0362298 A1 Nov. 17, 2022

(30) Foreign Application Priority Data
Sep. 26, 2019 (KR) ........................ 10-2019-0119148

(51) Int. Cl.
| | |
|---|---|
| A61K 40/31 | (2025.01) |
| A61K 40/11 | (2025.01) |
| A61K 40/42 | (2025.01) |
| A61P 35/00 | (2006.01) |
| C07K 14/705 | (2006.01) |
| C07K 14/725 | (2006.01) |
| C07K 14/73 | (2006.01) |
| C07K 14/735 | (2006.01) |
| C07K 16/28 | (2006.01) |
| C12N 5/0783 | (2010.01) |
| A61K 38/00 | (2006.01) |

(52) U.S. Cl.
CPC ........ *C07K 14/70521* (2013.01); *A61K 40/11* (2025.01); *A61K 40/31* (2025.01); *A61K 40/4209* (2025.01); *A61P 35/00* (2018.01); *C07K 14/7051* (2013.01); *C07K 14/70514* (2013.01); *C07K 14/70532* (2013.01); *C07K 14/70535* (2013.01); *C07K 14/70578* (2013.01); *C07K 14/70596* (2013.01); *C07K 16/2863* (2013.01); *C12N 5/0636* (2013.01); *A61K 38/00* (2013.01)

(58) Field of Classification Search
CPC .................................................... A61K 40/31
See application file for complete search history.

(56) References Cited

U.S. PATENT DOCUMENTS

| | | | |
|---|---|---|---|
| 10,106,622 B2 | 10/2018 | Yoo et al. | |
| 2017/0233492 A1 | 8/2017 | Yoo et al. | |
| 2019/0269727 A1* | 9/2019 | Fachin | A61M 1/3496 |
| 2019/0315872 A1 | 10/2019 | Yu et al. | |
| 2020/0271647 A1* | 8/2020 | Lee | C07K 16/42 |
| 2021/0130456 A1 | 5/2021 | Xie | |
| 2021/0403576 A1 | 12/2021 | Jeong et al. | |

FOREIGN PATENT DOCUMENTS

| | | | |
|---|---|---|---|
| CN | 106008721 A | 10/2016 | |
| CN | 108341881 A | 7/2018 | |
| CN | 108707198 A | 10/2018 | |
| CN | 109422815 A | 3/2019 | |
| CN | 113166244 A | 7/2021 | |
| KR | 10-2016-0017918 A | 2/2016 | |
| KR | 10-2018-0102116 A | 9/2018 | |
| WO | WO-2012079000 A1 * | 6/2012 | A61P 35/02 |

OTHER PUBLICATIONS

Office Action from corresponding Chinese Patent Application No. 202080067658.8, dated Apr. 13, 2023.
Liu, B., et al.; "Development of c-MET-specific chimeric antigen receptor-engineered natural killer cells with cytotoxic effects on human liver cancer HepG2 cells", Molecular Medicine RE POR TS 20: 2823-2831, 2019.
Tchou, J., et al.; "Safety and Efficacy of Intratumoral Injections of Chimeric Antigen Receptor (CAR) T Cells in Metastatic Breast Cancer", Cancer Immunol Res; 5(12) Dec. 2017.
Huang, "c-Met CAR-T", 2018, pp. 1-76.
Office Action from corresponding Japanese Patent Application No. 2022-519423, dated Mar. 20, 2023.
International Search Report cited in International Application No. PCT/KR2020/013127 filed on Jan. 22, 2021.
June, Carl H. et al.; "Car T cell immunotherapy for human cancer", Science 359; 1361-1365, 2018.
Office Action from corresponding Korean Application No. 10-2019-0119148, Dated Jun. 21, 2023.

* cited by examiner

*Primary Examiner* — Arthur S Leonard
(74) *Attorney, Agent, or Firm* — Harness, Dickey & Pierce, P.L.C.

(57) ABSTRACT

The present invention relates to a chimeric antigen receptor comprising a c-Met binding domain, and a use thereof. The chimeric antigen receptor comprising a c-Met domain, of the present invention, can be effectively usable as an agent for treating various diseases associated with c-Met expression.

16 Claims, 44 Drawing Sheets
Specification includes a Sequence Listing.

c-Met-CAR-002
1497 bp

CHIMERIC ANTIGEN RECEPTOR COMPRISING ANTI C-MET ANTIBODY OR ANTIGEN BINDING FRAGMENT THEREOF, AND USE THEREOF

CROSS-REFERENCE TO RELATED APPLICATIONS

This application is a national phase application of PCT Application No. PCT/KR2020/013127 filed on Sep. 25, 2020, which claims the benefit and priority to Korean Patent Application No. 10-2019-0119148 filed on Sep. 26, 2019. The entire disclosures of the applications identified in this paragraph are incorporated herein by references.

TECHNICAL FIELD

The present disclosure relates to a chimeric antigen receptor including a c-Met-binding domain, and a use thereof.

BACKGROUND ART

Activation of c-Met induces a variety of biological responses including cell growth, scattering and motility, invasion, protection against cell death, branching morphogenesis, and increase of angiogenesis. Therefore, dispensable activation of c-Met under a pathological condition may provide cancer cells with proliferation, survival, and invasion/metastasis potentials. Considering the various biological and physiological functions affected by c-Met activity, c-Met protein has become a multi-purpose therapeutic target.

Recently, increased attention has been paid to adoptive cell therapy, a kind of immunotherapy, in which immune cells are strengthened in vivo and genetically modified in vitro and then returned back into the same body. Particularly, active research is ongoing into the use of a chimeric antigen receptor (CAR), which is an artificial receptor expressed through genetically recombinant modification.

SUMMARY

Technical Problem

Leading to the present disclosure, intensive and thorough research conducted by the present inventors into the development of a chimeric antigen receptor capable of effectively treating c-Met expression-related diseases and an effector cell including same, resulted in constructing an anti-c-Met CAR binding specifically to c-Met and a T cell expressing same and finding that the anti-c-Met CAR-T exhibits therapeutic effects on various carcinomas associated with c-Met expression.

Therefore, an aspect of the present disclosure is to provide a nucleic acid molecule encoding an anti-c-Met chimeric antigen receptor, and a vector carrying same.

Another aspect of the present disclosure is to provide an anti-c-Met chimeric antigen receptor molecule including a polypeptide encoded by the nucleic acid molecule, and an effector cell expressing same on the surface thereof.

A further aspect of the present disclosure is to provide a pharmaceutical composition including the effector cell and a pharmaceutically acceptable carrier.

Solution to Problem

According to an aspect thereof, the present disclosure provides a nucleic acid molecule coding for an anti-c-Met chimeric antigen receptor including:

a c-Met-binding domain, a transmembrane domain, and an intracellular signaling domain.

In an embodiment of the present disclosure, the c-Met-binding domain is an antibody or an antigen binding fragment thereof, which binds specifically to c-Met.

In a specific embodiment of the present disclosure, the antibody or the antigen-binding fragment thereof is a nucleic acid molecule including complementarity determining region 1 of heavy chain (CDRH1), complementarity determining region 2 of heavy chain (CDRH2), and complementarity determining region 3 of heavy chain (CDRH3), which have the amino acid sequences of SEQ ID NOS: 15, 16, and 17, respectively; and complementarity determining region 1 of light chain (CDRL1), complementarity determining region 2 of light chain (CDRL2), and complementarity determining region 3 of light chain (CDRL3), which have the amino acid sequences of SEQ ID NOS: 18, 19, and 20, respectively.

In another specific embodiment of the present disclosure, the antibody or the antigen-binding fragment thereof is a nucleic acid molecule including a heavy chain variable region (VH) consisting of the amino acid sequence of SEQ ID NO: 21; and a light chain variable region (VL) consisting of the amino acid sequence of SEQ ID NO: 22.

In another specific embodiment of the present disclosure, the antibody or the antigen-binding fragment thereof is a nucleic acid molecule including a heavy chain variable region (VH) consisting of the amino acid sequence of SEQ ID NO: 64; and a light chain variable region (VL) consisting of the amino acid sequence of SEQ ID NO: 22.

In another specific embodiment of the present disclosure, the antibody or the antigen-binding fragment thereof is a nucleic acid molecule including a heavy chain variable region (VH) consisting of the amino acid sequence of SEQ ID NO: 65; and a light chain variable region (VL) consisting of the amino acid sequence of SEQ ID NO: 22.

In another specific embodiment of the present disclosure, the antibody or the antigen-binding fragment thereof is a nucleic acid molecule including a heavy chain variable region (VH) consisting of the amino acid sequence of SEQ ID NO: 65; and a light chain variable region (VL) consisting of the amino acid sequence of SEQ ID NO: 66.

As used herein, the term "antibody" or "Ab" refers to a protein or polypeptide sequence derived from an immunoglobulin molecule which binds specifically to a given antigen. The antibody may be a natural antibody or a recombinant antibody.

As used herein, the term "recombinant antibody" refers to an antibody which is generated using a recombinant DNA technology, for example, an antibody expressed by an animal cell expression system. The term should also be construed to mean an antibody produced through the translation of a synthetic DNA molecule coding for the antibody.

The antibody is intended to encompass an intact antibody and an antigen binding fragment of an antibody molecule. An intact antibody has a structure composed of two full-length light chains and two full-length heavy chains, with a disulfide linkage between each of the light chains and the heavy chains.

The term "heavy chain", as used herein, refers to the larger of the two types of polypeptide chains present in antibody molecules in their naturally occurring conformations, and which normally determines the class to which the antibody belongs. The "heavy chain" means both the full-length heavy chain and a fragment thereof that includes a VH domain, which is a heavy chain variable region of an antibody, comprising an amino acid sequence having a variable region sequence sufficient to impart specificity to an antigen, and CH1, CH2, and CH3 domains, which are three heavy chain constant regions. The constant region of heavy chain has gamma (γ), mu (μ), alpha (α), delta (δ), and epsilon (ε) types, and gamma1 (γ1), gamma2 (γ2), gamma3 (γ3), gamma4 (γ4), alpha1 (α1), and alpha2 (α2) subclasses.

As used herein, the term "light chain" refers to the smaller of the two types of polypeptide chains present in antibody molecules in their naturally occurring conformations. The term "light chain" means both the full-length light chain and a fragment thereof that include VL domain, which is a light chain variable region of an antibody, comprising an amino acid sequence having a variable region sequence sufficient to impart specificity to an antigen, and CL domain, which is a light chain constant region. The constant region of light chain has kappa and lambda types (Cellular and Molecular Immunology, Wonsiewicz, M. J., Ed., Chapter 45, pp. 41-50, W. B. Saunders Co. Philadelphia, PA (1991); Nisonoff, A., Introduction to Molecular Immunology, 2nd Ed., Chapter 4, pp. 45-65, Sinauer Associates, Inc., Sunderland, MA (1984)).

The term "antigen" or "Ag" refers to a molecule that provokes an immune response. This immune response may involve either antibody production, or the activation of specific immunologically-competent cells, or both.

As used herein, the term "complementarity determining region (CDR)" refers to an amino acid sequence of a hypervariable region in an immunoglobulin heavy or light chain (Kabat et al., Sequences of Proteins of Immunological Interest, 4th Ed., U.S. Department of Health and Human Services, National Institutes of Health (1987)). The heavy chain (CDRH1, CDRH2, and CDRH3) and the light chain (CDRL1, CDRL2, and CDRL3) each include three CDRs. CDRs provide major contact residues in the binding of an antibody to an antigen or epitope.

The antibody of the present disclosure includes monoclonal antibodies, multi-specific antibodies, human antibodies, humanized antibodies, chimeric antibodies, single-chain Fv (scFv), single-chain antibodies, Fab fragments, F(ab') fragments, disulfide-linked Fv (sdFv), anti-idiotype (anti-Id) antibodies, epitope-binding fragments of the above-mentioned antibodies, and the like, but is not limited thereto.

As used herein, the term "framework" or "FR" refers to a variable domain residue other than a hypervariable region (HVR) residue. The FR of the variable domain is generally composed of four FR domains FR1, FR2, FR3, and FR4. Therefore, the HVR and FR sequences are typically shown in the following order in VH (or VL/Vk):

(a) FRH1 (Framework region 1 of Heavy chain)-CDRH1 (complementarity determining region 1 of Heavy chain)-FRH2-CDRH2-FRH3-CDRH3-FRH4; and (b) FRL1 (Framework region 1 of Light chain)-CDRL1 (complementarity determining region 1 of Light chain)-FRL2-CDRL2-FRL3-CDRL3-FRL4.

c-Met (mesenchymal-epithelial transition factor), which is expressed on cell surfaces, is a receptor tyrosine kinase that is encoded by the Met proto-oncogene. Structurally, c-Met is a disulfide-linked heterodimer consisting of an extracellular alpha subunit (50 kDa) and a transmembrane beta subunit (140 kDa) and is characterized by an extracellular domain for ligand binding, a membrane-spanning segment, and a tyrosine kinase catalytic motif involved in phosphorylation of tyrosine residues within the intracellular domain (Dean et al., Nature, 4: 318 (6044): 385, 1985; Park et al., PNAS, 84 (18): 6379, 1976; Maggiora et al., J. Cell Physiol., 173:183, 1997). Upon binding to the ligand HGF (hepatocyte growth factor), c-Met dimerizes, autophosphorylates cytoplasmic tyrosine residues and, in turn, interacts with various proteins that mediate downstream signaling pathways. c-Met activation results in a variety of biological responses which lead to increased cell growth, scattering and motility, invasion, protection from apoptosis, branching morphogenesis, and angiogenesis. Under pathological conditions, improper activation of c-Met may confer proliferative, survival and invasive/metastatic abilities of cancer cells. In light of the variety of biological and physiological functions impacted by c-Met activity, the c-Met protein has become a therapeutic target for versatile purposes.

As used herein, the term "specifically bind" or similar expressions thereto mean that an antibody or antigen-binding fragment thereof, or other constructs, such as scFv, form a complex with an antigen that is relatively stable under physiological conditions.

In an embodiment of the present disclosure, the specific binding of the anti-c-Met antibody or antigen-binding fragment thereof can be at least characterized as an equilibrium dissociation constant of about $1\times10^{-6}$ M or less (e.g., $9\times10^{-7}$ M, $8\times10^{-7}$ M, $7\times10^{-7}$ M, $6\times10^{-7}$ M, $5\times10^{-7}$ M, $4\times10^{-7}$ M, $3\times10^{-7}$ M, $2\times10^{-7}$ M, or $1\times10^{-7}$ M), at least about $1\times10^{-7}$ M or less (e.g., $9\times10^{-8}$ M, $8\times10^{-8}$ M, $7\times10^{-8}$ M, $6\times10^{-8}$ M, $5\times10^{-8}$ M, $4\times10^{-8}$ M, $3\times10^{-8}$ M, $2\times10^{-8}$ M, or $1\times10^{-8}$ M), or at least about $1\times10^{-8}$ M or less (e.g., $9\times10^{-9}$ M, $8\times10^{-9}$ M, $7\times10^{-9}$ M, $6\times10^{-9}$ M, $5\times10^{-9}$ M, $4\times10^{-9}$ M, $3\times10^{-9}$ M, $2\times10^{-9}$ M, or $1\times10^{-9}$ M) (a smaller KD indicates tighter binding). Methods of determining specific binding between two molecules are well known in the art, as exemplified by equilibrium dialysis, surface plasmon resonance, and the like. However, an isolated antibody which specifically bind to human c-Met may exhibit cross-reactivity with different antigens such as c-Met molecules from other species.

As used herein, the term "affinity" refers to the total strength of non-covalent interactions between a single binding site of a molecule (e.g., an antibody) and a binding partner thereof (e.g., an antigen). Unless specified otherwise, the term "binding affinity" refers to the intrinsic binding affinity which reflects a 1:1 interaction between the members of a binding pair (e.g., an antibody and an antigen). The affinity between molecule Y and its partner Y may be typically represented by a dissociation constant (Kd). The affinity can be measured by common methods known in the art, including those described in the present disclosure.

The term "human antibody", as used herein, refers to an antibody possessing an amino acid sequence which corresponds to an antibody produced by human or a human cell, or an antibody amino acid sequence derived from a non-human source that utilizes human antibody repertoires or other human antibody encoding sequences. Such a definition of the human antibody excludes a humanized antibody comprising non-human antigen binding residues.

As used herein, the term "chimeric antibody" refers to an antibody in which a portion of the heavy chain and/or light chain is derived from a particular source or species while the remainder of the heavy chain and/or light chain is derived from a different source or species.

As used herein, the term "humanized antibody" refers to a chimeric immunoglobulin which comprises the minimal sequence derived from non-human immunoglobulin of non-human (e.g., mouse) antibodies, or an immunoglobulin chain or fragment thereof (e.g., Fv, Fab, Fab', F(ab')$_2$ or other antigen-binding sub-sequences of the antibody). In most cases, humanized antibodies are human immunoglobulins (recipient antibodies) in which residues from a complementarity-determining region (CDR) of the recipient are replaced by residues from a CDR of a non-human species (donor antibody), such as mouse, rat or rabbit having desired specificity, affinity, and capacity. In some instances, Fv framework region (FR) residues of the human immunoglobulin are replaced by corresponding non-human residues. In addition, humanized antibodies may include residues which are found neither in the recipient antibody nor in the imported CDR or framework sequences. These modifications are made to further improve and optimize antibody performance. In general, the humanized antibody will include substantially all of at least one, and typically two, variable domains, in which all or substantially all of the CDR regions correspond to CDR regions of a non-human immunoglobulin and all or substantially all of the FR regions have sequences of FR regions of a human immunoglobulin sequence. The humanized antibody includes at least a portion of an immunoglobulin constant region (Fc region), typically a constant region (Fc region) of a human immunoglobulin.

The anti-c-Met antibody or antigen-binding fragment thereof according to the present disclosure may include variants of the amino acid sequence within a range capable of specifically recognizing c-Met as recognized by a person skilled in the art. For example, in order to improve binding affinity and/or other biological properties of an antibody, modifications may be made to an amino acid sequence of the antibody. Such modifications include, for example, deletions, insertions, and/or substitutions of amino acid sequence residues of the antibody.

Such amino acid variations are made based on relative similarity of amino acid side chain substituents such as hydrophobicity, hydrophilicity, charge, and size. According to analysis on sizes, shapes, and types of amino acid side chain substituents, it can be seen that arginine, lysine, and histidine are all positively charged residues; alanine, glycine, and serine have similar sizes; and phenylalanine, tryptophan, and tyrosine have similar shapes. Thus, based on these considerations, arginine, lysine, and histidine; alanine, glycine, and serine; and phenylalanine, tryptophan, and tyrosine are regarded biologically functional equivalents.

In the introduction of variations, account may be taken of the hydropathic index of amino acids. Each amino acid has been assigned a hydropathic index on the basis of hydrophobicity and charge characteristics thereof: isoleucine (+4.5); valine (+4.2); leucine (+3.8); phenylalanine (+2.8); cysteine/cystine (+2.5); methionine (+1.9); alanine (+1.8); glycine (-0.4); threonine (-0.7); serine (-0.8); tryptophan (-0.9); tyrosine (-1.3); proline (-1.6); histidine (-3.2); glutamate (-3.5); glutamine (-3.5): aspartate (-3.5); asparagine (-3.5); lysine (-3.9); and arginine (-4.5).

The hydrophobic amino acid indexes are very important in giving interactive biological functions of proteins. It is known in the art that similar biological activity is retained upon substitution between amino acids similar in hydropathic index. In cases where a variation is introduced with reference to the hydrophobic indexes, the substitution is made between amino acids having a difference in the hydrophobic index within preferably ±2, more preferably ±1, and still more preferably ±0.5.

Meanwhile, it is also well known that substitutions between amino acids having similar hydrophilicity values result in proteins with equivalent biological activity. As disclosed in U.S. Pat. No. 4,554,101, each amino acid residue has been assigned the following hydrophilicity values: arginine (+3.0); lysine (+3.0); aspartate (+3.0±1); glutamate (+3.0±1); serine (+0.3); asparagine (+0.2); glutamine (+0.2); glycine (0); threonine (-0.4); proline (-0.5±1); alanine (-0.5); histidine (-0.5); cysteine (-1.0); methionine (-1.3); valine (-1.5); leucine (-1.8); isoleucine (-1.8); tyrosine (-2.3); phenylalanine (-2.5); tryptophan (-3.4).

In cases where variations are introduced with reference to the hydrophilicity values, substitutions may be made between amino acids that exhibit a hydrophilicity value difference of preferably within ±2, more preferably within ±1, and even more preferably within ±0.5.

Amino acid exchanges in proteins which do not entirely alter activity of a molecule are known in the art (H. Neurath, R. L. Hill, The Proteins, Academic Press, New York, 1979). The most common exchanges are occurring between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

In an embodiment of the present disclosure, the anti-c-Met antibody or the antigen-binding fragment thereof according to the present disclosure includes an anti-c-Met antibody defined by the above-descried concrete amino acid sequences or an antigen-binding fragment thereof (e.g., the amino acid sequences of the variable regions of heavy chain and the variable regions of light chains, or a fragment of the amino acid sequence including CDRH1 to CDRH3 and CDRL1 to CDRL3).

In an embodiment of the present disclosure, the anti-c-Met antibody or the antigen-binding fragment thereof includes a sequence having a homology of at least about 60% (e.g., 60%, 61%, 62%, 63%, 64%, 65%, 66%, 67%, 68%, or 69%), more preferably at least 70% (e.g., 70%, 71%, 72%, 73%, 74%, 75%, 76%, 77%, 78%, or 79%), still more preferably at least 80% (e.g., 80%, 81%, 82%, 83%, 84%, 85%, 86%, 87%, 88%, or 89%), and most preferably at least 90% (e.g., 90%, 91%, 92%, 93%, 94%, 95%, 96%, 97%, 98%, 99%, or 100%) to the antibody defined with the specific amino acid sequences described above, or the amino acid sequence of CDR, heavy chain variable region, or light-chain variable region of the antigen-binding fragment thereof. All integers between 70% and 100% (inclusive of both endpoints) and decimal percentages thereof are considered to fall within the scope of the present disclosure with respect to percent homology.

The term "chimeric antigen receptor" (CAR), as used herein, refers to a recombinant polypeptide including at least one extracellular antigen-binding domain, a transmembrane domain, and a stimulatory molecule-derived intracellular signaling domain.

The chimeric antigen receptor of the present disclosure includes the foregoing anti-c-Met antibody or antigen-binding fragment thereof as an extracellular antigen domain. Therefore, the chimeric antigen receptor of the present disclosure is expressed as an anti-c-Met chimeric antigen receptor (anti-c-Met CAR), anti-c-Met CAR, or the like.

In the terms "c-Met CAR-001" to "c-Met CAR-003", "pMT-c-Met-CAR", and "pGemT-c-Met-CAR", used in the example of the present disclosure, "c-Met CAR" is a code name standing for the anti-c-Met chimeric antigen receptor invented by the present inventors, and refer to a chimeric antigen receptor including an extracellular antigen-binding domain that specifically binds to the foregoing c-Met.

The term "stimulatory molecule," refers to a molecule expressed by a T cell that provides the primary cytoplasmic signaling sequence(s) that regulate primary activation of the TCR complex in a stimulatory way for at least some aspects of the T cell signaling pathway. In greater detail, the primary signal is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (or "primary signaling domain") that acts in a stimulatory manner may contain a signaling motif which is known as immunoreceptor tyrosine-based activation motif or ITAM. Examples of an ITAM containing a primary cytoplasmic signaling sequence that is of particular use in the disclosure includes, but is not limited to, those derived from TCR zeta, FcR gamma, FcR beta, CD3 gamma, CD3 delta, CD3 epsilon, CD5, CD22, CD79a, CD79b, CD278 (also known as "ICOS") and CD66d.

As used herein, the term "signaling domain" refers to the functional portion of a protein which acts by transmitting information within the cell to regulate cellular activity via defined signaling pathways by generating second messengers or functioning as effectors by responding to such messengers.

According to an embodiment of the present disclosure, the chimeric antigen receptor optionally further includes a leader sequence (LS). The leader sequence is located at the amino-terminal (N-terminal) of a recombinant polypeptide constituting the chimeric antigen receptor. The leader sequence is optionally cleaved from the antigen binding domain during intracellular processing and localization of the chimeric antigen receptor to the cellular membrane.

In a specific embodiment of the present disclosure, the leader sequence may be a leader sequence of hCD8 alpha, a leader sequence of hGM-CSF receptor alpha-chain, or a leader sequence of 3E8 antibody.

In a more specific embodiment of the present disclosure, the leader sequence is a leader sequence including the amino acid sequence encoded by the nucleotide sequence of SEQ ID NO: 26, 28, or 30.

In an embodiment, the c-Met-binding domain of the chimeric antigen receptor is linked to the transmembrane domain by a hinge region, a spacer region, or a combination thereof.

According to a specific embodiment of the present disclosure, the hinge region, the spacer region, or the combination thereof may be a hinge derived from human IgG1, IgG4, or IgD, a hinge derived from CD8 alpha, CH3 derived from IgG1, an extracellular domain derived from CD28, or a combination of all or some of these sequences.

According to a more specific embodiment of the present disclosure, the hinge region includes the amino acid sequence encoded by the nucleotide sequence of 32, 34, 36, 38, 40, or 44.

In a specific embodiment of the present disclosure, the transmembrane domain includes a transmembrane domain selected from the group consisting of an alpha, beta, or zeta chain of a T-cell receptor, CD28, CD3 epsilon, CD45, CD4, CD5, CD8, CD9, CD16, CD22, CD33, CD37, CD64, CD80, CD86, CD134, CD137, and CD154.

According to a more specific embodiment of the present disclosure, the transmembrane domain includes the amino acid sequence encoded by the nucleotide sequence of SEQ ID NO: 42, 46, or 47.

In an embodiment of the present disclosure, the intracellular signaling domain includes a signaling domain of CD3 zeta.

In a specific embodiment of the present disclosure, the signaling domain of CD3 zeta includes an amino acid sequence encoded by the nucleotide sequence of SEQ ID NO: 55, 57, or 59.

In another embodiment of the present disclosure, the intracellular signaling domain further includes as a costimulatory domain a signaling domain of a protein selected from the group consisting of OX40, CD2, CD27, CD28, CDS, ICAM-1, LFA-1 (CD11a/CD18), ICOS (CD278), and 4-1BB (CD137). That is, the chimeric antigen receptor of the present disclosure may be a recombinant polypeptide including an antigen binding domain, a transmembrane domain, a stimulatory molecule-derived intracellular signaling domain, and a costimulatory molecule-derived signaling domain.

In a specific embodiment of the present disclosure, the costimulatory domain includes an amino acid sequence encoded by the nucleotide sequence of SEQ ID NO: 49, 51, or 53.

In accordance with another aspect thereof, the present disclosure provides a vector carrying a nucleic acid molecule coding for the chimeric antigen receptor stated above.

As used herein, the term "nucleic acid" is intended to encompass DNA (gDNA and cDNA) and RNA molecules, and the nucleotides that are the basic building blocks of the nucleic acid molecule include not only natural nucleotides, but also analogues having modified sugar or base moieties (Scheit, Nucleotide Analogs, John Wiley, New York (1980); and Uhlman and Peyman, Chemical Reviews, 90:543-584 (1990)).

In one embodiment of the present disclosure, the nucleotide sequence encoding the chimeric antigen receptor polypeptide of the present disclosure is sufficient to be a nucleotide sequence encoding the amino acid sequence constituting the chimeric antigen receptor molecule, and it would be obvious to a person skilled in the art that such a nucleotide sequence is not limited to any particular nucleotide sequence.

The reason is that even if the nucleotide sequence undergoes mutation, the expression of the mutated nucleotide sequence into a protein may not cause a change in the protein sequence. This is called codon degeneracy. Therefore, the nucleotide sequence includes nucleotide sequences comprising functionally equivalent codons, codons encoding the same amino acid (e.g., the number of codons for arginine or serine is six due to codon degeneracy), or codons encoding biologically equivalent amino acids.

Considering the foregoing variation having biological equivalent activity, the nucleic acid molecule encoding the chimeric antigen receptor polypeptide of the present disclosure is construed to also include sequences having substantial identity to the sequences described in the sequence listings. The substantial identity means that, when the sequence of the present disclosure and any other sequences are aligned to correspond to each other as much as possible and the aligned sequences are analyzed using an algorithm that is commonly used in the art, the sequences have at least 60% homology (e.g., 60%, 61%, 62%, 63%, 64%, 65%, 66%, 67%, 68%, or 69%), more preferably at least 70% homology (e.g., 70%, 71%, 72%, 73%, 74%, 75%, 76%, 77%, 78%, or 79%), still more preferably at least 80% homology (e.g., 80%, 81%, 82%, 83%, 84%, 85%, 86%, 87%, 88%, or 89%), and most preferably at least 90% homology (e.g., 90%, 91%, 92%, 93%, 94%, 95%, 96%, 97%, 98%, 99%, or ≟ 100%). All integers between 70% and 100% (inclusive of both endpoints) and decimal percentages thereof are considered to fall within the scope of the present disclosure with respect to percent identify.

Methods of the alignment for sequence comparison are known in the art. Various methods and algorithms for the alignment are disclosed in Smith and Waterman, *Adv. Appl. Math.* 2:482 (1981); Needleman and Wunsch, *J. Mol. Bio.* 48:443 (1970); Pearson and Lipman, *Methods in Mol. Biol.* 24: 307-31 (1988); Higgins and Sharp, *Gene* 73:237-44

(1988); Higgins and Sharp, *CABIOS* 5:151-3 (1989); Corpet et al., *Nuc. Acids Res.* 16:10881-90 (1988); Huang et al., *Comp. Appl. BioSci.* 8:155-65 (1992) and Pearson et al., *Meth. Mol. Biol.* 24:307-31 (1994). The NCBI Basic Local Alignment Search Tool (BLAST) (Altschul et al., *J. Mol. Biol.* 215:403-10 (1990)) is accessible from the NBCI (National Center for Biotechnology Information) or the like and, on the Internet, may be used in connection with sequence analysis programs, such as BLASTP, BLASTN, BLASTX, TBLASTN and TBLASTX. BLAST may be accessed through the BLAST webpage of the NCBI's website. The method for comparing sequence homology using such a program is available from the BLAST help page of the NCBI's website.

In an embodiment of the present disclosure, the vector is selected from the group consisting of DNA, RNA, a plasmid, a lentiviral vector, an adenoviral vector, an adeno-associated viral vector, and a retroviral vector.

In an embodiment of the present disclosure, the vector is a lentiviral vector. In a specific embodiment, the vector further includes a promoter. The promoter may be, for example, EF-1 promoter, but is not limited thereto.

In another embodiment of the present disclosure, the vector may be a retroviral vector. Retroviruses provide a convenient platform for a gene delivery system. A gene selected for gene delivery may be inserted in the retroviral vector and may be packaged within a retroviral particle. Then, the recombinant retrovirus may be delivered to a target host cell in vivo or in vitro. Many retroviral vectors are known in the art, and in a specific embodiment of the present disclosure, the retroviral vector may be a pMT retroviral vector, which is an MLV-based retroviral vector, but is not limited thereto.

Methods of introducing the vector of the present disclosure into a cell and expressing the same are well known in the related art. The vector may be easily introduced into a host cell, e.g., a mammalian cell, a bacterial cell, a yeast cell, or an insect cell according to methods known in the art. For example, the vector may be delivered into a host cell by physical, chemical, or biological means. The physical means includes calcium phosphate coprecipitation, lipofection, particle bombardment, microinjection, electroporation, and the like. The chemical means includes colloidal dispersion systems, such as a macromolecular complex, a nanocapsule, a microsphere, and a bead, and lipid-based systems including an oil-in-water emulsion, a micelle, a mixed micelle, and a liposome. The biological means includes use of a DNA or RNA vector, such as a lentiviral vector or a retroviral vector, as described above.

Provided according to another aspect of the present disclosure is an anti-c-Met chimeric antigen receptor molecule including a polypeptide encoded by the above-described nucleic acid molecule.

The anti-c-Met chimeric antigen receptor according to an embodiment of the present disclosure can be obtained by introducing the above-described nucleic acid and a vector carrying the same into cells, followed by expression thereof. Thus, a description of the nucleic acid molecule and the vector carrying the same is omitted within the overlapping extent thereof.

In accordance with still another aspect thereof, the present disclosure provides an effector cell expressing the anti-c-Met chimeric antigen receptor molecule on the surface.

In an embodiment of the present disclosure, the effector cell is selected from the group consisting of dendritic cells, killer dendritic cells, mast cells, natural killer cells, B lymphocytes, T lymphocytes, macrophages, and progenitor cells thereof, but is not limited thereto. The T lymphocytes are selected from the group consisting of inflammatory T lymphocytes, cytotoxic T lymphocytes, regulatory T lymphocytes, or helper T lymphocytes.

In the present disclosure, the effector cell includes a group of autologous cells or allogenic cells. That is to say, the effector cell includes a group of autologous cells or allogenic cells expressing the present anti-c-Met CAR polypeptide.

As used herein, the term "autologous" refers to any material which is derived from an individual and is to be re-introduced to the same individual. As used herein, the term "allogeneic" refers to any material derived from a different animal of the same species as an individual to which the material is introduced.

According to an embodiment of the present disclosure, the effector cell includes a group of cells transfected or transduced with a vector comprising a nucleic acid molecule encoding the anti-c-Met CAR polypeptide. The transfection or transduction may be achieved by various means known in the art without limitation.

Accordingly, according to a specific embodiment of the present disclosure, the anti-c-Met CAR encoding nucleic acid molecule is delivered into an effector cell, e.g., a T lymphocyte or a natural killer cell, and transcribed into mRNA. The anti-c-Met CAR polypeptide is translated from the mRNA and expressed on the surface of the effector cell.

As validated in the examples of the present disclosure, the effector cell expressing the anti-c-Met chimeric antigen receptor of the present disclosure effectively kills the cancer cell lines A549, PC-3, MCF-7, SKOV3, and SK-HEP-1. Therefore, the effector cell expressing the anti-c-Met chimeric antigen receptor of the present disclosure can be advantageously used as an active ingredient of compositions for treatment of various carcinomas.

In accordance with another aspect thereof, the present disclosure provides a pharmaceutical composition for immunotherapy, the pharmaceutical composition including the effector cell expressing the anti-c-Met CAR polypeptide and a pharmaceutically acceptable carrier.

Here, the "immunotherapy" refers to a treatment of cancer wherein the immune system helps to remove cancer. Immunotherapy is classified into active immunotherapy and passive immunotherapy. The active immunotherapy includes i) cancer vaccine therapy of activating the immune system by injecting cancer cells or substances produced by cancer cells into human body, and ii) immunomodulatory therapy of activating specific leukocytes by administering immuno-modulatory agents, such as cytokines (interferons, interleukins, etc.), and growth factors. Passive immunotherapy includes antibody therapy and immune cell therapy binding to specific cancer cells. Specifically, immune cell therapy includes dendritic cell vaccine therapy, chimeric antigen receptor T (CAR-T) cell therapy, natural killer (NK) cell therapy, cytotoxic T lymphocyte (CTL) therapy, adoptive cell transfer, and the like, but is not limited thereto. In the present disclosure, the immunotherapy mainly refers to the above-described immune cell therapy.

The pharmaceutical composition of the present disclosure includes effector cells expressing an antibody or antigen-binding fragment thereof that binds to the c-Met antigen of a target cell, or a chimeric antigen receptor including the same, and thus is effective in the diagnosis or treatment of a disease associated with high expression of c-Met.

Thus, in an embodiment of the present disclosure, the pharmaceutical composition of immunotherapy is a pharmaceutical composition for treatment of a disease associated with c-Met expression.

In the present disclosure, the disease associated with c-Met expression is selected from the group consisting of brain cancer (malignant brain tumor), glioma, breast cancer, pancreatic cancer, pleural mesothelioma, liver cancer, gastric cancer, lung cancer, ovarian cancer, and colorectal cancer, but with no limitations thereto.

In an embodiment of the present disclosure, the glioma is a type of tumor that starts in the glial cells, which are located within the nervous system of the human body. Glial cells are classified into central nervous glial cells including astrocytes, oligodendrocytes (oligodendroglia), and ependymal cells; and peripheral nervous glial cells including Schwann's cells and capsular cells. Gliomas are also classified by cell type into i) astrocytic tumor (inclusive of glioblastoma), ii) oligodendroglial tumor, and iii) ependymoma.

The pharmaceutical composition of the present disclosure may include the CAR-expressing effector cells, for example, a plurality of CAR-expressing effector cells, in combination with one or more pharmaceutically or physiologically acceptable carriers, diluents or excipients. The pharmaceutical composition may include a buffer, such as neutral buffered saline or phosphate buffered saline; a carbohydrate, such as glucose, mannose, sucrose, dextran, or mannitol; a protein; a polypeptide or an amino acid such as glycine; an antioxidant; a chelating agent, such as EDTA or glutathione; an adjuvant (e.g., aluminum hydroxide); and a preservative. In an embodiment of the present disclosure, the pharmaceutical composition is formulated for intravenous administration.

The pharmaceutical composition of the present disclosure may be administered orally or parenterally, and may be attained by, for example, intravenous administration, subcutaneous administration, intradermal administration, intramuscular administration, intraperitoneal administration, intratumoral injection, intracerebral administration, intracranial administration, intrapulmonary administration, and intrarectal administration, but is not limited thereto.

The pharmaceutical composition including the effector cell of the present disclosure is administered to a patient by intradermal or subcutaneous injection. In one embodiment, the pharmaceutical composition of the present disclosure is administered by intravenous injection. In another embodiment, the pharmaceutical composition of the present disclosure is administered directly into tumors, lymph nodes, or infected sites.

A subject in need of the present disclosure can receive standard treatment using high-dose chemotherapy after peripheral blood stem cell transplantation. In an embodiment of the present disclosure, a subject in need of the present disclosure may receive expanded CAR T cells of the present disclosure by administration, after or simultaneously with the peripheral blood stem cell transplantation. In another embodiment, the expanded cells are administered before or after surgery.

The appropriate dose for the "immunologically effective amount", "anti-tumor effective amount", "tumor-suppressing effective amount", or "therapeutic amount" of the pharmaceutical composition of the present disclosure is determined by factors, such as a formulating method, a manner of administration, patient's age, body weight, and sex, pathological condition, food, administration time, administration route, excretion rate, and responsiveness, and an ordinarily skilled practitioner can easily determine and prescribe the dose that is effective for the desired treatment or prevention, and the appropriate dose will be determined by clinical trials. As used herein, the term "treatment" refers to a reduction, suppression, amelioration, or eradication of a disease condition. As used herein, the term "anti-tumor" encompasses a decrease in tumor volume, a decrease in the number of tumor cells, a decrease in the number of metastases, an increase in life expectancy, a decrease in tumor cell proliferation, a decrease in tumor cell survival, or ameliorations of various physiological symptoms associated with the cancerous condition, but with no limitations thereto.

It may generally be stated that the pharmaceutical composition including T cells described herein may be administered at a dosage of $10^4$ to $10^9$ cells/kg body weight, in some cases, $10^5$ to $10^6$ cells/kg body weight (including all integer values within those ranges). The T cell composition may also be administered multiple times at these doses. The cells may be administered by using infusion techniques that are commonly known in immunotherapy (see, e.g., [Rosenberg et al., New Eng. J. of Med. 319:1676, 1988]).

The pharmaceutical composition of the present disclosure may also be used in combination with other pharmaceutically active drugs and therapies in addition to the above-described active ingredient. The term "combination" may be expressed as simultaneous or coadministration. The CAR-expressing effector cell described herein and at least one additional therapeutic agent may be administered simultaneously, in the same composition or in separate compositions, or sequentially. For sequential administration, the CAR-expressing cell described herein may be administered first, and the additional agent may be administered second, or the order of administration can be reversed.

Examples of a therapeutic agent that can be used in combination with the pharmaceutical composition of the present disclosure include: one or more chemotherapeutic agents; one or more targeted therapies; PD-1/PD-L1-specific immune checkpoint inhibitors, which are known in the art, but are not limited thereto.

In accordance with still another aspect thereof, the present disclosure provides an immunotherapeutic method including a step of administering an effector cell expressing the chimeric antigen receptor to a subject in need of the immunotherapy.

The disease associated with c-Met expression, which is the target disease of the immunotherapeutic method of the present disclosure, is the same as those defined with respect to the target diseases of the treatment of the pharmaceutical composition.

In one embodiment of the present disclosure, the subject is a mammal or a human.

Since the method for treatment of a disease associated with c-Met expression according to the present disclosure commonly uses the foregoing effector cell expressing the chimeric antigen receptor as an active ingredient, the description of overlapping contents therebetween is omitted in order to avoid excessive complexity of the present specification.

Advantageous Effects of Invention

The present disclosure aims to provide an anti-c-Met chimeric antigen receptor and a pharmaceutical composition using the same. The chimeric antigen receptor including the c-Met-binding domain according to the present disclosure can find advantageous applications as a therapeutic agent for various diseases associated with c-Met expression.

DETAILED DESCRIPTION

A better understanding of the present disclosure may be obtained via the following examples which are set forth to illustrate, but are not construed to limit the present disclosure.

EXAMPLES

Throughout the present specification, the "%" used to express the concentration of a specific material, unless otherwise particularly stated, refers to (wt/wt) % for solid/solid, (wt/vol) % for solid/liquid, and (vol/vol) % for liquid/liquid.

Example List

Examples 1 to 4: Preparation of Anti-c-Met-Chimeric Antigen Receptor Gene

Example 5. Construction of pGemT-c-Met-CAR Vector

Example 6. Construction of pMT-c-Met-CAR Retroviral Vector

Example 7. Preparation of Anti-c-Met-CAR Gene-Expressing T Cell

Example 8. In Vitro Assay for Anticancer Activity of Anti-c-Met-CAR-Expressing T Cell

Example 1. Preparation of c-Met-CAR-001 Gene

Example 1-1. Preparation of Anti-c-Met scFv Antibody Gene

The nucleotide sequence of the polynucleotide coding for the heavy-chain variable region and light-chain variable region of the c-Met-specific antibody of the present disclosure was obtained through the previous application (Korean Patent Application No. 10-2018-0140196) (Table 1).

TABLE 1

| Nucleotide sequence of finally selected unique anti-c-Met scFv clones | | |
|---|---|---|
| ID | Nucleotide sequence | SEQ ID NO |
| 1E4-H4k2 | CAGGTGCAGCTGGTGCAGTCTGGCGCCGAAGTGAAGAAGCC CGGCTCCTCCGTGAAGGTCTCCTGCCAGGGCTCCGGCTACTC CTTCCCCACCCACTGGATCACCTGGGTGCGACAGGCCCCCGG CCAAGGCCTGGAATGGATGGGCACCATCGACCCCACCGACTC CTACAACTTCTACGGCCCCAGCTTCCAGGGCAGAGTGACCAT CACCGCCGACTCCTCCACGTCCACCGCCTACATGGAGCTGTC CTCCCTGAGATCTGAGGACACCGCCATGTACTACTGCGCCAG GGACGGCAACTACTACGACTCCCGGGGCTACTACTACGATAC CTTCGACATGTGGGGCCAGGGCACCCTGGTCACCGTCTCCTC AGGCGGTGGAGGATCTGGAGGAGGCGGCTCTGGGGGGGGC GGCTCTGACATCCAGATGACCCAGTCCCCCAGCTCCCTGTCC GCCTCCGTGGGCGACAGAGTGACCATCACCTGTCGGGCCTCC CAGGGCATCTCCACCTACCTGGCCTGGTATCAGCAGAAGCCC GGCAAAGCCCCCAAGCTGCTGATCTACTCCGCCTCCACCCTG GAATCCGGCGTGCCCTCCAGATTCTCCGGCTCCGGCTCTGGC ACCGACTTCACCCTGACCATCTCCAGCCTGCAGCCCGAGGAC TTTGCCACCTACTACTGCCAGCAGGCCGACTCCTTCCCCCTG ACCTTCGGCGGAGGCACCAAGGTGGAAATCAAACGT | 24 |

Example 1-2. Preparation of c-Met-CAR-001 Gene

Figure 1:
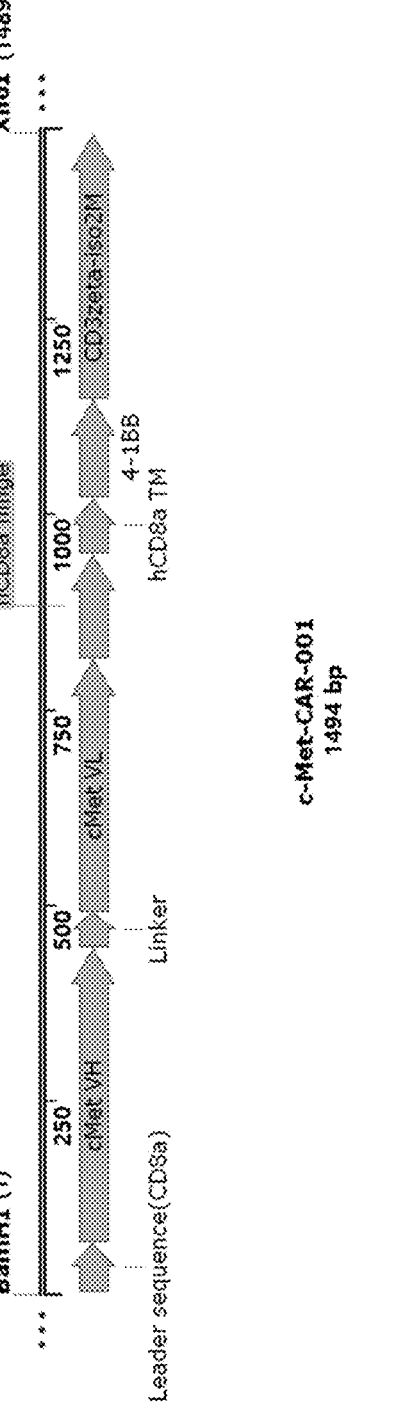
FIG. 1 is a schematic diagram illustrating the structure of c-Met-CAR-001 construct according to the present disclosure.
Figure 2:
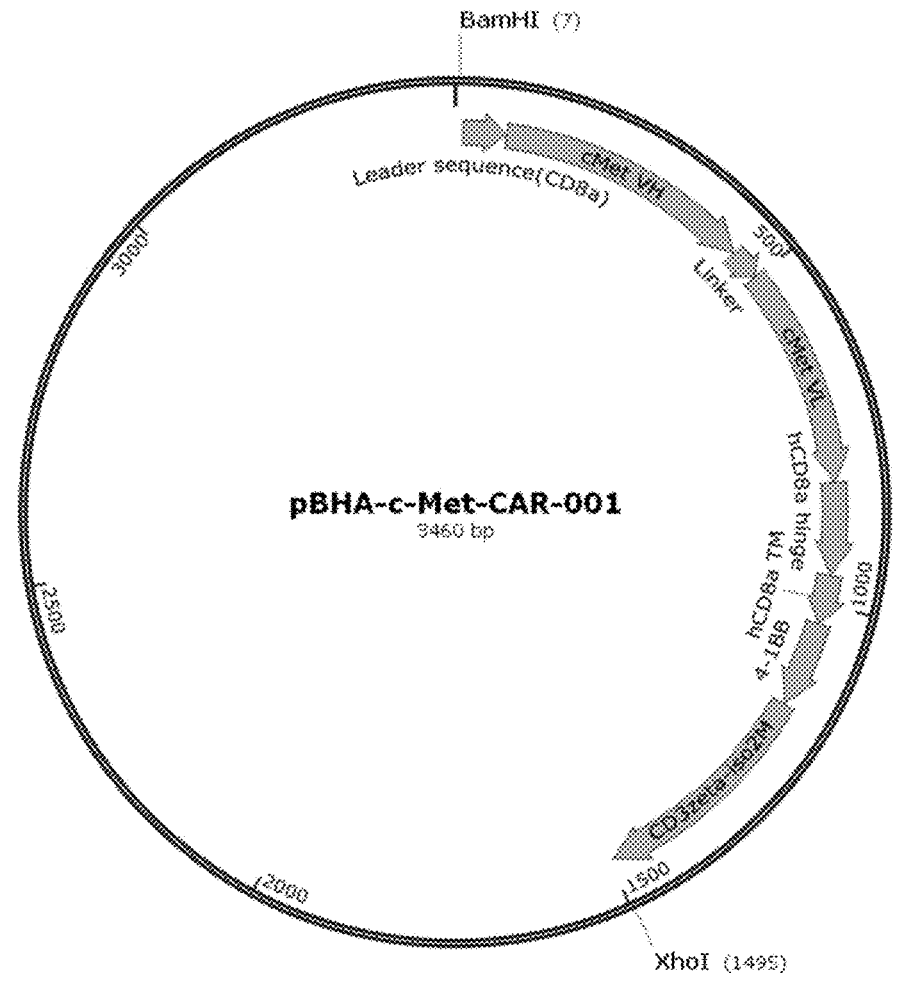
FIG. 2 is a map illustrating the structure of pBHA-c-Met-CAR-001 plasmid according to the present disclosure.

A nucleotide sequence for the anti-c-Met scFv antibody of the present disclosure was designed to include the BamH I restriction site and the leader sequence of CD8 alpha in the 5' region of the variable heavy chain (VH) and the hinge and TM of hCD8 alpha, the costimulatory domains 4-1BB, CD3ζ-iso2M (modified CD3ζ-iso2), and the Xho I restriction site in the 3' region of the variable light chain (VL). The nucleotide sequence thus obtained has the structure of BamH I-hCD8αLS-scFv-hCD8α hinge-hCD8αTM-41BB-CD3ζ-iso2M-Xho I (Table 2). Based on this structure, c-Met-CAR-001 construct of SEQ ID NO: 60 (FIG. 1) was synthesized. The synthesized pBHA-c-Met-CAR-001 (FIG. 2) was used to establish other c-Met-CAR constructs.

TABLE 2

| ID | Nucleotide sequence |
| --- | --- |
| | LS, Hinge, TM, ICD, Costimulatory Domain, and CD3ζ Gene Sequences |
| BamH I-start codon- hCD8a LS | GGATCCATGGCCCTCCCTGTCACCGCCCTGCTGCTTCCGCTGGC TCTTCTGCTCCACGCCGCTCGGCCC |
| ScFv | (Table 1) |
| hCD8a hinge | ACCACTACCCCAGCACCGAGGCCACCCACCCCGGCTCCTACCAT CGCCTCCCAGCCTCTGTCCCTGCGTCCGGAGGCATGTAGACCCG CAGCTGGTGGGGCCGTGCATACCCGGGGTCTTGACTTCGCCTG CGAT |
| hCD8a TM | ATCTACATTTGGGCCCCTCTGGCTGGTACTTGCGGGGTCCTGCT GCTTTCACTCGTGATCACTCTTTACTGT |
| 4-1BB | AAGCGCGGTCGGAAGAAGCTGCTGTACATCTTTAAGCAACCCTT CATGAGGCCTGTGCAGACTACTCAAGAGGAGGACGGCTGTTCAT GCCGGTTCCCAGAGGAGGAGGAAGGCGGCTGCGAACTG |
| CD3ζ-iso2M- stop codon- Xho I | CGCGTGAAATTCAGCCGCAGCGCAGATGCTCCAGCCTACAAGCA GGGGCAGAACCAGCTCTACAACGAACTCAATCTTGGTCGGAGAG AGGAGTACGACGTGCTGGACAAGCGGAGAGGACGGGACCCAGA AATGGGCGGGAAGCCGCGCAGAAAGAATCCCCAAGAGGGCCTG TACAACGAGCTCCAAAAGGATAAGATGGCAGAAGCCTATAGCGA GATTGGTATGAAAGGGGAACGCAGAAGAGGCAAAGGCCACGAC GGACTGTACCAGGGACTCAGCACCGCCACCAAGGACACCTATGA CGCTCTTCACATGCAGGCCCTGCCGCCTCGGTAACTCGAG |

Example 2. Preparation of c-Met-CAR-002 Gene

Example 2-1. Preparation of Anti-c-Met scFv Antibody Gene

Amplification was performed by PCR using the primers of SEQ ID NOS: 1 and 2 (Table 3) on the template pBHA-c-Met-CAR-001 (FIG. 2) obtained through gene synthesis. In this regard, the primer designed to bind to the 5' region of the variable heavy chain (VH) of the anti-c-Met scFv antibody had 12 nucleotide sequences of hGM-CSF rec.α (human GM-CSF receptor alpha-chain) while the primer designed to bind to the 3' region of the variable light chain (VL) of the anti-c-Met scFv antibody had nine nucleotide sequences of hinges and three nucleotide sequences of hCD28 pECD. The PCR product thus obtained had the nucleotide sequence of hGM-CSF rec.α-scFv-hinge-hCD28 pECD (Table 4). The PCR product was used in subsequent PCR procedures.

TABLE 3

Information on Nucleotide Sequence of Primer

| SEQ ID NO | Primer | Nucleotide sequence |
| --- | --- | --- |
| 1 | GMCSF rec.a LS + 1E4-H4k2 scFv(F) | CTCCTGATCCCACAGGTGCAGCTGGTG |
| 2 | 1E4-H4k2 scFv + hinge + hCD28 pECD(R) | AATTGCGGCCGCACGTTTGATTTCCAC |
| 3 | AS + BamHI + GMCSF rec.a LS(F) | CGGGATCCATGCTTCTCCTGGTGACAA |
| 4 | GMCSF rec.a LS + 1E4-H4k2 scFv(R) | CAGCTGCACCTGTGGGATCAGGAGGAA |
| 5 | 1E4-H4k2 scFv + hinge + CD28 pECD(F) | GAAATCAAACGTGCGGCCGCAATTGAA |
| 6 | AS + Xho1 + CD3-ζ(R) | CCGCTCGAGTTATTAGCGAGGGGGCAGG |
| 7 | 3E8 LS + 1E4-H4k2 scFv(F) | GGTGTCCACTCCCAGGTGCAGCTGGTG |
| 8 | 1E4-H4k2 scFv + hIgD hinge(R) | ACCTGGCCAGCGACGTTTGATTTCCAC |
| 9 | BamHI + 3E8 VH(F) | GGATCCATGGAATGGAGCTGGGTC |
| 10 | 1E4-H4k2 scFv + 3E8 LS(R) | CAGCTGCACCTGGGAGTGGACACCTGT |

TABLE 3-continued

| SEQ ID NO | Primer | Nucleotide sequence |
|---|---|---|
| | Information on Nucleotide Sequence of Primer | |
| 11 | 1E4-H4k2 scFv + hIgD hinge(F) | GAAATCAAACGTCGCTGGCCAGGTTCT |
| 12 | XhoI + CD3zeta(R) | CCGCTCGAGTTAGCGAGGGGGCAGGGC |
| 13 | T7(F) | TATACGACTCACTATAGGG |
| 14 | SP6(R) | ATTTAGGTGACACTATAG |

Example 2-2. Preparation of Signal Sequence Gene of hGM-CSF Receptor Alpha-Chain Amplification was performed by PCR using the primers of SEQ ID NOS: 3 and 4 (Table 3) on the template pMT-CAR-001 plasmid carrying the signal sequence of hGM-CSF rec.α. In this regard, the primer designed to bind to a 5' region of hGM-CSF rec.α had the BamH I restriction site while the primer designed to bind to a 3' region of hGM-CSF rec.α had 12 nucleotide sequences of the variable heavy chain (VH) of the anti-c-Met antibody. The PCR product thus obtained had the nucleotide sequence of BamHI-hGM-CSF rec.α-scFv (Table 4). The PCR product was used in subsequent PCR procedures.

bind to 5' regions of the hinge had 12 nucleotide sequences of the variable light chain (VL) of anti-c-Met antibody while the primer designed to bind to a 3' region of CD3ζ-iso2 had a Xho I restriction site. The PCR product thus obtained had the nucleotide sequence of scFv-Hinge-hCD28 pECD-hCD28 TM-hCD28 ICD-CD3ζ-iso2-XhoI (Table 4). The PCR product was used in subsequent PCR procedures.

Example 3. Preparation of c-Met-CAR-003 Gene

Example 3-1. Preparation of Anti-c-Met scFv Antibody Gene

Amplification was performed by PCR using the primers of SEQ ID NOS: 7 and 8 (Table 3) on the template

TABLE 4

| ID | Nucleotide sequence |
|---|---|
| | LS, Hinge, TM, ICD, Costimulatory Domain, and CD3ζ Gene Sequences |
| BamH I-start codon-hGM-CSF rec.a LS | GGATCCATGCTTCTCCTGGTGACAAGCCTTCTGCTCTGTGAGTT ACCACACCCAGCATTCCTCCTGATCCCA |
| ScFv | (Table 1) |
| hinge | GCGGCCGCA |
| hCD28pECD | ATTGAAGTTATGTATCCTCCTCCTTACCTAGACAATGAGAAGAGC AATGGAACCATTATCCATGTGAAAGGGAAACACCTTTGTCAAG TCCCCTATTTCCCGGACCTTCTAAGCCC |
| hCD28TM | TTTTGGGTGCTGGTGGTGGTTGGGGGAGTCCTGGCTTGCTATA GCTTGCTAGTAACAGTGGCCTTTATTATTTTCTGGGTG |
| hCD28 ICD | AGGAGTAAGAGGAGCAGGCTCCTGCACAGTGACTACATGAACA TGACTCCCCGCCGCCCCGGGCCCACCCGCAAGCATTACCAGCC CTATGCCCCACCACGCGACTTCGCAGCCTATCGCTCC |
| CD3ζ-iso2-stop codon-Xho I | AGAGTGAAGTTCAGCAGGAGCGCAGACGCCCCCGCGTACCAGC AGGGCCAGAACCAGCTCTATAACGAGCTCAATCTAGGACGAAG AGAGGAGTACGATGTTTTGGACAAGAGACGTGGCCGGGACCCT GAGATGGGGGGAAAGCCGAGAAGGAAGAACCCTCAGGAAGGC CTGTACAATGAACTGCAGAAAGATAAGATGGCGGAGGCCTACA GTGAGATTGGGATGAAAGGCGAGCGCCGGAGGGGCAAGGGGC ACGATGGCCTTTACCAGGGTCTCAGTACAGCCACCAAGGACAC CTACGACGCCCTTCACATGCAGGCCCTGCCCCCTCGCTAATAA CTCGAG |

Figure 3:
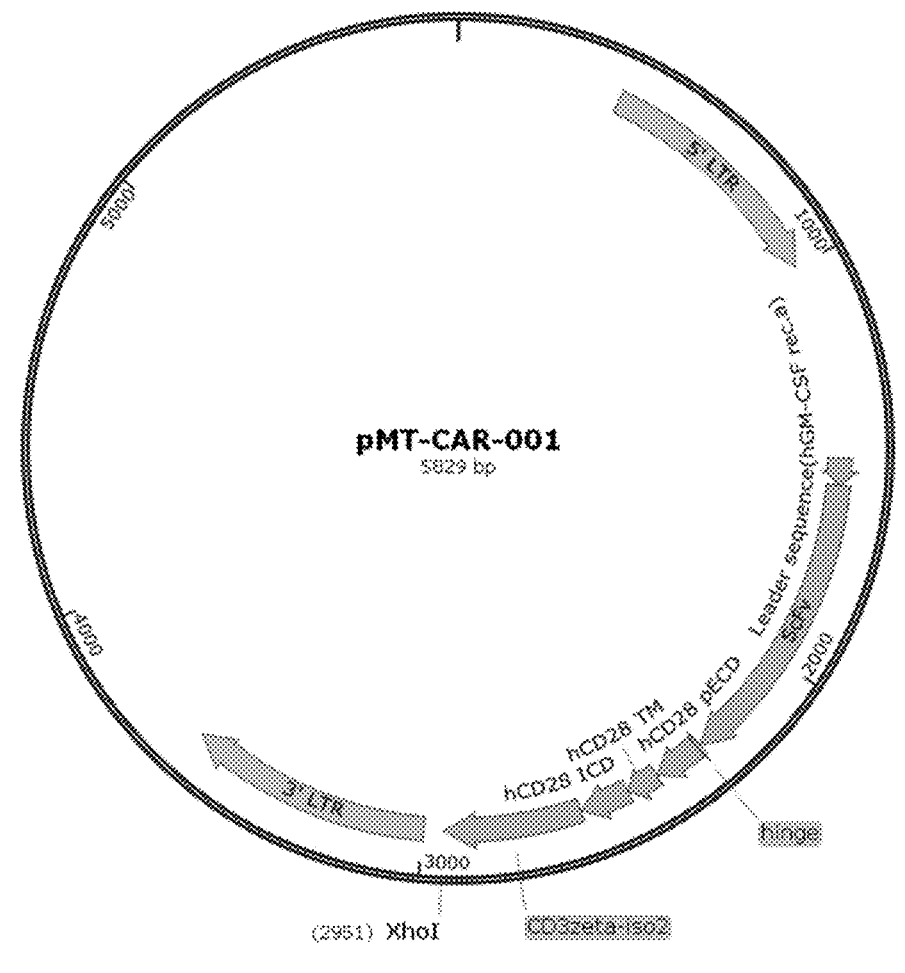
FIG. 3 is a map illustrating the structure of pMT-CAR-001 plasmid according to the present disclosure.

Example 2-3. Preparation of Hinge, TM, ICD, Costimulatory Domain, and CD3ζ Gene Sequences PCR was performed using the primers of SEQ ID NOS: 5 and 6 (Table 3) on the template pMT-CAR-001 plasmid including a hinge, pECD and TM of hCD28, ICD, and hCD3ζ-iso2 (FIG. 3). In this regard, the primers designed to pBHA-c-Met-CAR-001 (FIG. 2) obtained through gene synthesis. In this regard, the primer designed to bind to a 5' region of the variable heavy chain (VH) of the anti-c-Met scFv antibody had 12 nucleotide sequences of 3E8 leader sequence (LS) while the primer designed to bind to a 3' region of the variable light chain (VL) of the anti-c-Met scFv antibody had 12 nucleotide sequences of hIgD hinge. The PCR product thus obtained had the nucleotide sequence of 3E8 LS-scFv-hIgD hinge (Table 5). The PCR product was used in subsequent PCR procedures.

TABLE 5

| LS, Hinge, TM, ICD, Costimulatory Domain, and CD3ζ Gene Sequence | |
| --- | --- |
| ID | Nucleotide sequence |
| BamH I-start codon-3E8 LS | GGATCCATGGAATGGAGCTGGGTCTTTCTCTTCTTCCTGTCAGTAAC TACAGGTGTCCACTCC |
| ScFv | (Table 1) |
| IgD hinge | CGCTGGCCAGGTTCTCCAAAGGCACAGGCCTCCTCCGTGCCCACTG CACAACCCCAAGCAGAGGGCAGCCTCGCCAAGGCAACCACAGCCC CAGCCACCACCCGTAACACAGGTAGAGGAGGAGAAGAGAAGAAGAA GGAGAAGGAGAAAGAGGAACAAGAAGAGAGAGAGAGACAAAGACACCA GGTTGTCCG |
| IgG1 hinge | GAGCCCAAATCTTGTGACAAAACTCACACATGCCCACCGTGCCCA |
| IgG1 CH3 | GGGCAGCCCCGAGAACCACAGGTGTACACCCTGCCCCCCATCCCGG GATGAGCTGACCAAGAACCAGGTCAGCCTGACCTGCCTGGTCAAAG GCTTCTATCCCAGCGACATCGCCGTGGAGTGGGAGAGCAATGGGCA GCCGGAGAACAACTACAAGACCACGCCTCCCGTGCTGGACTCCGAC GGCTCCTTCTTCCTCTACAGCAAGCTCACCGTGGACAAGAGCAGGT GGCAGCAGGGGAACGTCTTCTCATGCTCCGTGATGCATGAGGCTCT GCACAACCACTACACGCAGAAGAGCCTCTCCCTGTCTCCGGGTAAA |
| CD28 TM | TTTTGGGTGCTGGTGGTGGTTGGTGGAGTCCTGGCTTGCTATAGCTT GCTAGTAACAGTGGCCTTTATTATTTTCTGGGTG |
| CD28 ICD | AGGAGTAAGAGGAGCAGGCTCCTGCACAGTGACTACATGAACATGA CTCCCCGCCGCCCCGGGCCCACCCGCAAGCATTACCAGCCCTATGC CCCACCACGCGACTTCGCAGCCTATCGCTCC |
| OX40 | GCCCTGTACCTGCTCCGGAGGGACCAGAGGCTGCCCCCCGATGCC CACAAGCCCCCTGGGGGAGGCAGTTTCCGGACCCCCATCCAAGAG GAGCAGGCCGACGCCCACTCCACCCTGGCCAAGATC |
| CD3ζ-iso1-stop codon-Xho I | AGAGTGAAGTTCAGCAGGAGCGCAGACGCCCCCGCGTACCAGCAG GGCCAGAACCAGCTCTATAACGAGCTCAATCTAGGACGAAGAGAGG AGTACGATGTTTTGGACAAGAGACGTGGCCGGGACCCTGAGATGGG GGGAAAGCCGCAGAGAAGGAAGAACCCTCAGGAAGGCCTGTACAAT GAACTGCAGAAAGATAAGATGGCGGAGGCCTACAGTGAGATTGGGA TGAAAGGCGAGCGCCGGAGGGGCAAGGGGCACGATGGCCTTTACC AGGGTCTCAGTACAGCCACCAAGGACACCTACGACGCCCTTCACAT GCAGGCCCTGCCCCCTCGCTAACTCGAG |

Example 3-2. Preparation of Leader Sequence (LS) Gene of 3E8 Antibody

Figure 4:
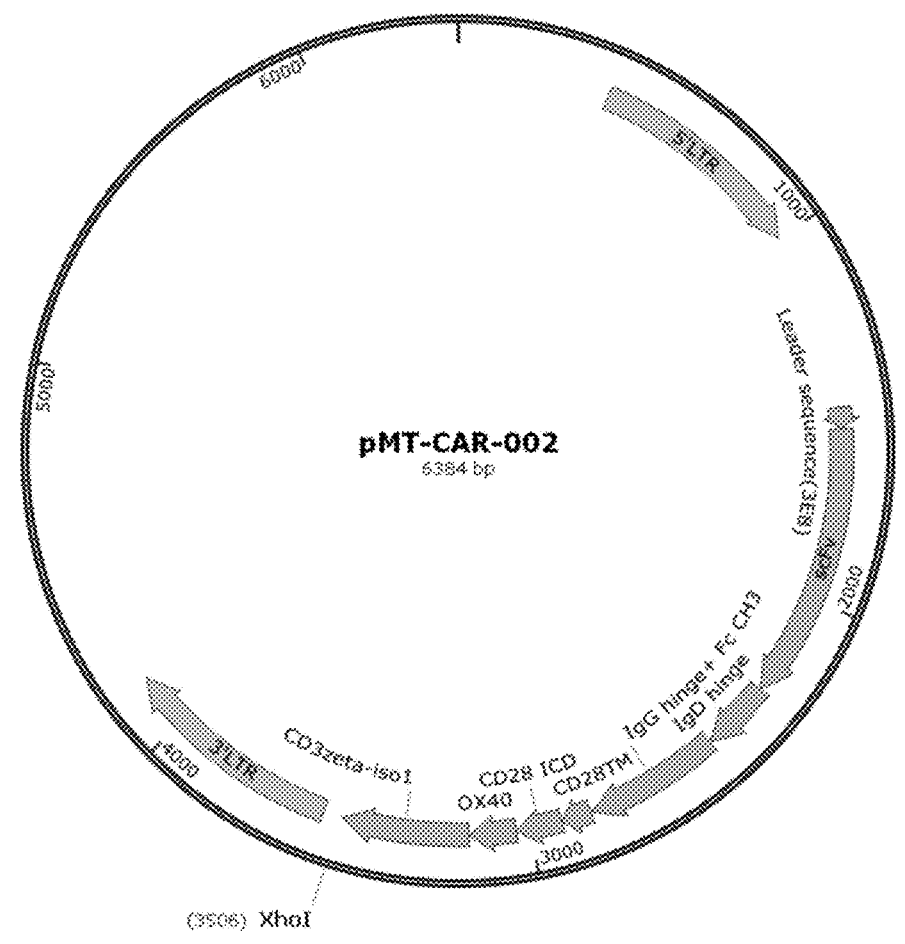
FIG. 4 is a map illustrating the structure of pMT-CAR-002 plasmid according to the present disclosure.

Amplification was performed by PCR using the primers of SEQ ID NOS: 9 and 10 (Table 3) on the template pMT-CAR-002 plasmid carrying the leader sequence (LS) of 3E8 antibody (FIG. 4). In this regard, the primer designed to bind to a 5' region of 3E8 leader sequence (LS) had the BamH I restriction site while the primer designed to bind to a 3' region of 3E8 leader sequence (LS) had 12 nucleotide sequences of the variable heavy chain (VH) of the anti-c-Met antibody. The PCR product thus obtained had the nucleotide sequence of BamH I-3E8 LS-scFv (Table 5). The PCR product was used in subsequent PCR procedures.

Example 3-3. Preparation of Hinge, TM, ICD, Costimulatory Domain, and CD3ζ Gene Sequences PCR was performed using the primers of SEQ ID NOS: 11 and 12 (Table 3) on the template pMT-CAR-002 plasmid including a hinge of human IgD, a hinge and CH3 of IgG1, TM and ICD of CD28, and the costimulatory domains OX40 and CD3ζ-iso1 (FIG. 4). In this regard, the primer designed to bind to a 5' region of the hIgD hinge had 12 nucleotide sequences of the variable light chain (VL) of anti-c-Met antibody while the primer designed to bind to a 3' region of CD3ζ-iso1 had a Xho I restriction site. The PCR product thus obtained had the nucleotide sequence of scFv-IgD hinge-IgG1 hinge-CH3-CD28 TM-CD28 ICD-OX40-CD3ζ-iso1-Xho I (Table 5). The PCR product was used in subsequent PCR procedures.

Example 4. Preparation of c-Met-CAR-004 Gene

Example 4-1. Preparation of Anti-c-Met scFv Antibody Gene

Amplification was performed by PCR using the primers of SEQ ID NOS: 7 and 8 (Table 3) on the template pBHA-c-Met-CAR-001 (FIG. 2) obtained through gene synthesis. In this regard, the primer designed to bind to a 5' region of the variable heavy chain (VH) of the anti-c-Met scFv antibody had 12 nucleotide sequences of 3E8 leader sequence (LS) while the primer designed to bind to a 3' region of the variable light chain (VL) of the anti-c-Met scFv antibody had 12 nucleotide sequences of hIgD hinge. The PCR product thus obtained had the nucleotide sequence of 3E8 LS-scFv-hinge-hIgD hinge (Table 6). The PCR product was used in subsequent PCR procedures.

TABLE 6

LS, Hinge, TM, ICD, Costimulatory Domain, and CD3ζ
Gene Sequence

| ID | Nucleotide sequence |
|---|---|
| BamH I-start codon-3E8 LS | GGATCCATGGAATGGAGCTGGGTCTTTCTCTTCTTCCTGTCAGTAA<br>CTACAGGTGTCCACTCC |
| ScFv | (Table 1) |
| IgD hinge | CGCTGGCCAGGTTCTCCAAAGGCACAGGCCTCCTCCGTGCCCACT<br>GCACAACCCCAAGCAGAGGGCAGCCTCGCCAAGGCAACCACAGC<br>CCCAGCCACCACCCGTAACACAGGTAGAGGAGGAGAAGAGAAGA<br>AGAAGGAGAAGGAGAAAGAGGAACAAGAAGAGAGAGAGACAAAG<br>ACACCAGGTTGTCCG |
| CD28 TM | TTTTGGGTGCTGGTGGTGGTTGGTGGAGTCCTGGCTTGCTATAGC<br>TTGCTAGTAACAGTGGCCTTTATTATTTTCTGGGTG |
| CD28 ICD | AGGAGTAAGAGGAGCAGGCTCCTGCACAGTGACTACATGAACATG<br>ACTCCCCGCCGCCCCGGGCCCACCCGCAAGCATTACCAGCCCTAT<br>GCCCCACCACGCGACTTCGCAGCCTATCGCTCC |
| OX40 | GCCCTGTACCTGCTCCGGAGGGACCAGAGGCTGCCCCCCGATGC<br>CCACAAGCCCCTGGGGGAGGCAGTTTCCGGACCCCCATCCAAG<br>AGGAGCAGGCCGACGCCCACTCCACCCTGGCCAAGATC |
| CD3ζ-iso1-stop codon-Xho I | AGAGTGAAGTTCAGCAGGAGCGCAGACGCCCCCGCGTACCAGCA<br>GGGCCAGAACCAGCTCTATAACGAGCTCAATCTAGGACGAAGAGA<br>GGAGTACGATGTTTTGGACAAGAGACGTGGCCGGGACCCTGAGAT<br>GGGGGGAAAGCCGCAGAGAAGGAAGAACCCTCAGGAAGGCCTGT<br>ACAATGAACTGCAGAAAGATAAGATGGCGGAGGCCTACAGTGAGA<br>TTGGGATGAAAGGCGAGCGCCGGAGGGGCAAGGGGCACGATGG<br>CCTTTACCAGGGTCTCAGTACAGCCACCAAGGACACCTACGACGC<br>CCTTCACATGCAGGCCCTGCCCCCTCGCTAACTCGAG |

Example 4-2. Preparation of Leader Sequence (LS) Gene of 3E8 Antibody

Figure 5:
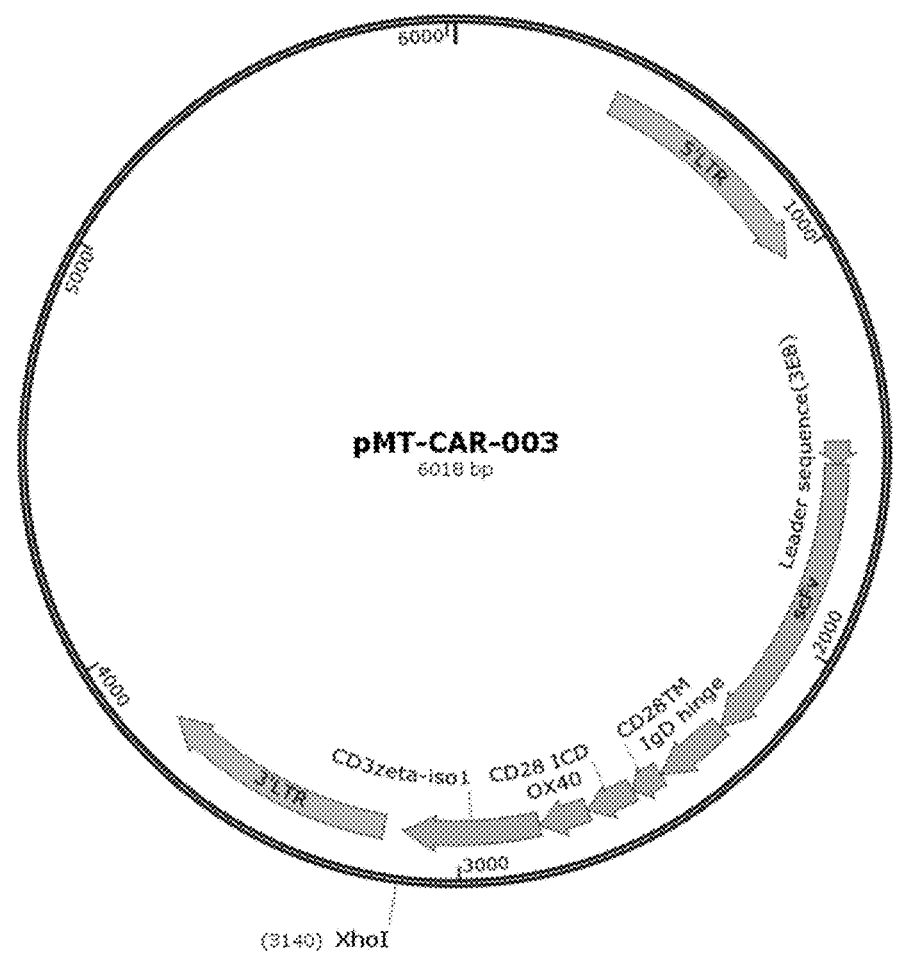
FIG. 5 is a map illustrating the structure of pMT-CAR-003 plasmid according to the present disclosure.

Amplification was performed by PCR using the primers of SEQ ID NOS: 9 and 10 (Table 3) on the template pMT-CAR-003 plasmid carrying the leader sequence (LS) of 3E8 antibody (FIG. 5). In this regard, the primer designed to bind to a 5' region of 3E8 leader sequence (LS) had the BamH I restriction site while the primer designed to bind to a 3' region of 3E8 leader sequence (LS) had 12 nucleotide sequences of the variable heavy chain (VH) of the anti-c-Met antibody. The PCR product thus obtained had the nucleotide sequence of BamH I-3E8 LS-scFv (Table 6). The PCR product was used in subsequent PCR procedures.

Example 4-3. Preparation of Hinge, TM, ICD, Costimulatory Domain, and CD3ζ Gene Sequences PCR was performed using the primers of SEQ ID NOS: 11 and 12 (Table 3) on the template pMT-CAR-003 plasmid including the hinge of human IgD, TM and ICD of CD28, and the costimulatory domains OX40 and CD3ζ-iso1 (FIG. 5). In this regard, the primer designed to bind to a 5' region of the hIgD hinge had 12 nucleotide sequences of the variable light chain (VL) of anti-c-Met antibody while the primer designed to bind to a 3' region of CD3ζ-iso1 had a Xho I restriction site. The PCR product thus obtained had the nucleotide sequence of scFv-hIgD hinge-CD28 TM-CD28 ICD-OX40-CD3ζ-iso1-Xho I (Table 6). The PCR product was used in subsequent PCR procedures.

Example 5. Construction of pGemT-c-Met-CAR Vector

Example 5-1. Construction of pGemT-c-Met-CAR-002 Vector

Figure 6:
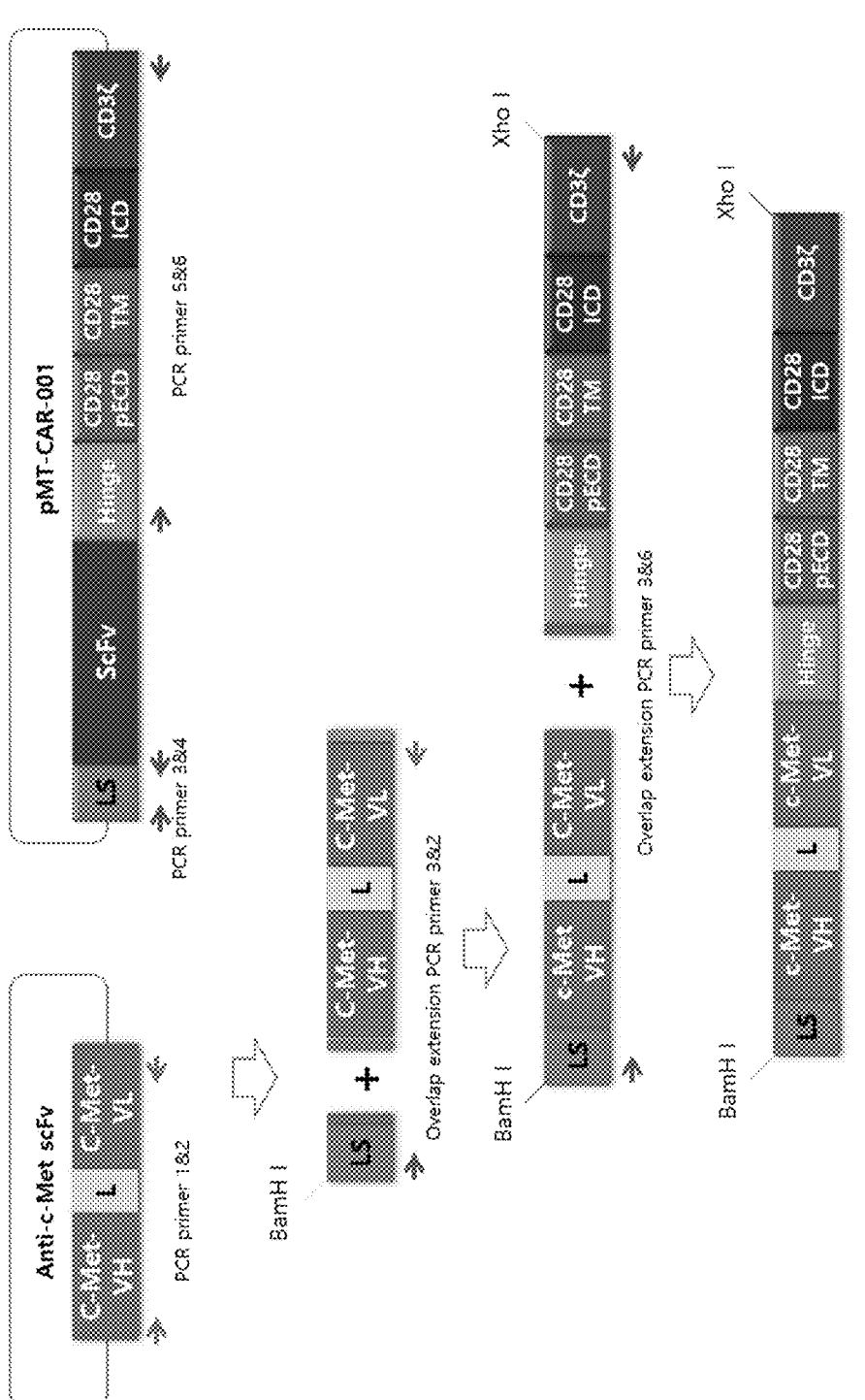
FIG. 6 is a schematic diagram illustrating a PCR amplification procedure for c-Met-CAR-002 according to the present disclosure.
Figure 7:
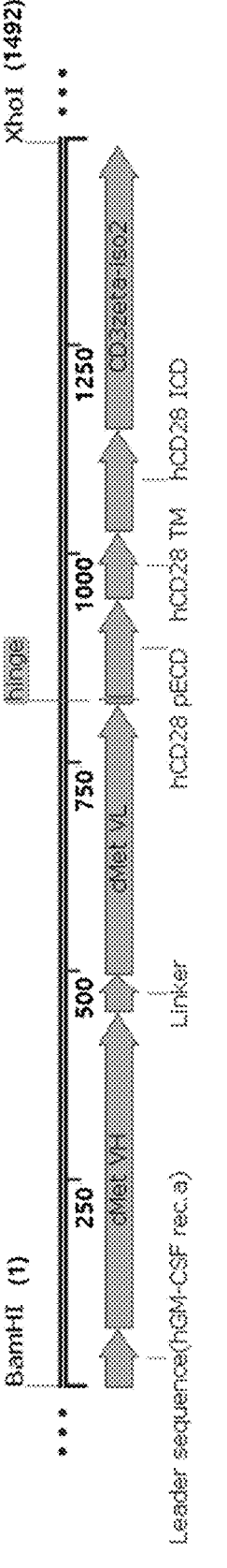
FIG. 7 is a schematic diagram illustrating the structure of c-Met-CAR-002 construct according to the present disclosure.

Amplification was performed by OE-PCR (overlap extension PCR) using the primers of SEQ ID NOS: 2 and 3 (Table 3), with the PCR products BamH I-hGM-CSF rec.α-scFv and hGM-CSF rec.α-scFv-hinge-hCD28 pECD serving as templates. OE-PCR was performed using the primers of SEQ ID NOS: 3 and 6 (Table 3) while the amplicons BamH I-hGM-CSF rec.α-scFv-hinge-hCD28 pECD and scFv-Hinge-hCD28 pECD-hCD28 TM-hCD28 ICD-CD3ζ-iso2-Xho I were used as templates (FIG. 6). The PCR product thus obtained had the nucleotide sequence of SEQ ID NO: 61 and was named c-Met-CAR-002 which was structured to include BamH I-hGM-CSF rec.α-scFv-Hinge-hCD28 pECD-hCD28 TM-hCD28 ICD-CD3ζ-iso2-Xho I (FIG. 7). This PCR product was ligated to pGemT ESAY vector (Promega, WI, USA) containing poly-T sequences at both ends of the linear DNA to attain pGemT-c-Met-CAR-002 construct. Sequencing analysis with the aid of primers of SEQ ID NOS: 13 and 14 (Table 3) confirmed that the amplicon has the same original sequence.

Example 5-2. Construction of pGemT-c-Met-CAR-003 Vector

Amplification was performed by OE-PCR (overlap extension PCR) using the primers of SEQ ID NOS: 9 and 8 (Table 3), with the PCR products BamH I-3E8 LS-scFv and 3E8 LS-scFv-hIgD hinge serving as templates. OE-PCR was performed using the primers of SEQ ID NOS: 9 and 12

Figure 8:
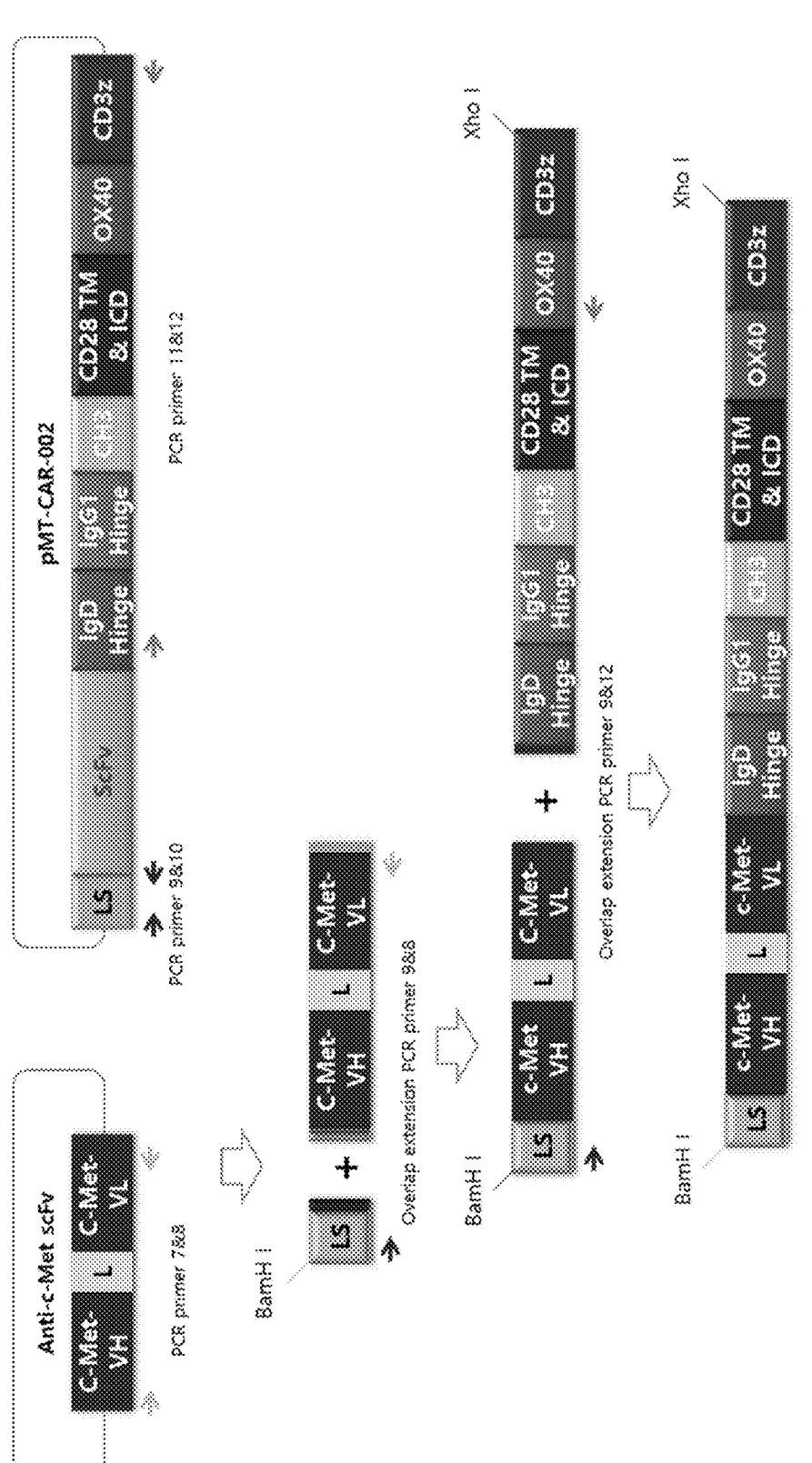
FIG. 8 is a schematic diagram illustrating a PCR amplification procedure for c-Met-CAR-003 according to the present disclosure.
Figure 9:
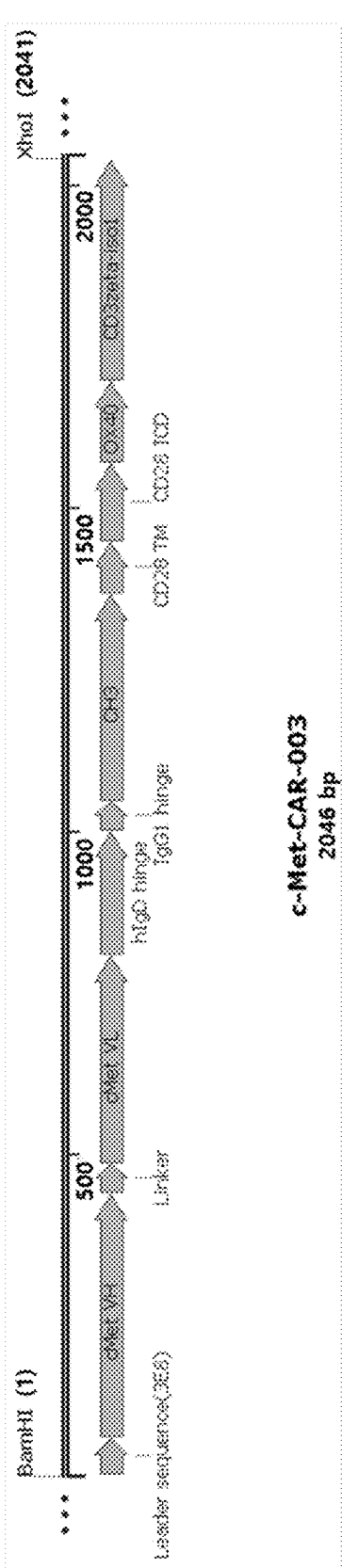
FIG. 9 is a schematic diagram illustrating the structure of c-Met-CAR-003 construct according to the present disclosure.

(Table 3) while the amplicons BamH I-3E8 LS-scFv-hIgD hinge and scFv-IgD hinge-IgG1 hinge-CH3-CD28 TM-CD28 ICD-OX40-CD3ζ-iso1-Xho I were used as templates (FIG. 8). The PCR product thus obtained had the nucleotide sequence of SEQ ID NO: 62 and was named c-Met-CAR-003 which was structured to include BamH I-3E8 LS-scFv-hIgD hinge-IgG1 hinge-CH3-CD28 TM-CD28 ICD-OX40-CD3ζ-iso1-Xho I (FIG. 9). This PCR product was ligated to pGemT ESAY vector containing poly-T sequences at both ends of the linear DNA to attain pGemT-c-Met-CAR-003 construct. Sequencing analysis with the aid of primers of SEQ ID NOS: 13 and 14 (Table 3) confirmed that the amplicon has the same original sequence.

Example 5-3. Construction of pGemT-c-Met-CAR-004 Vector

Figure 10:
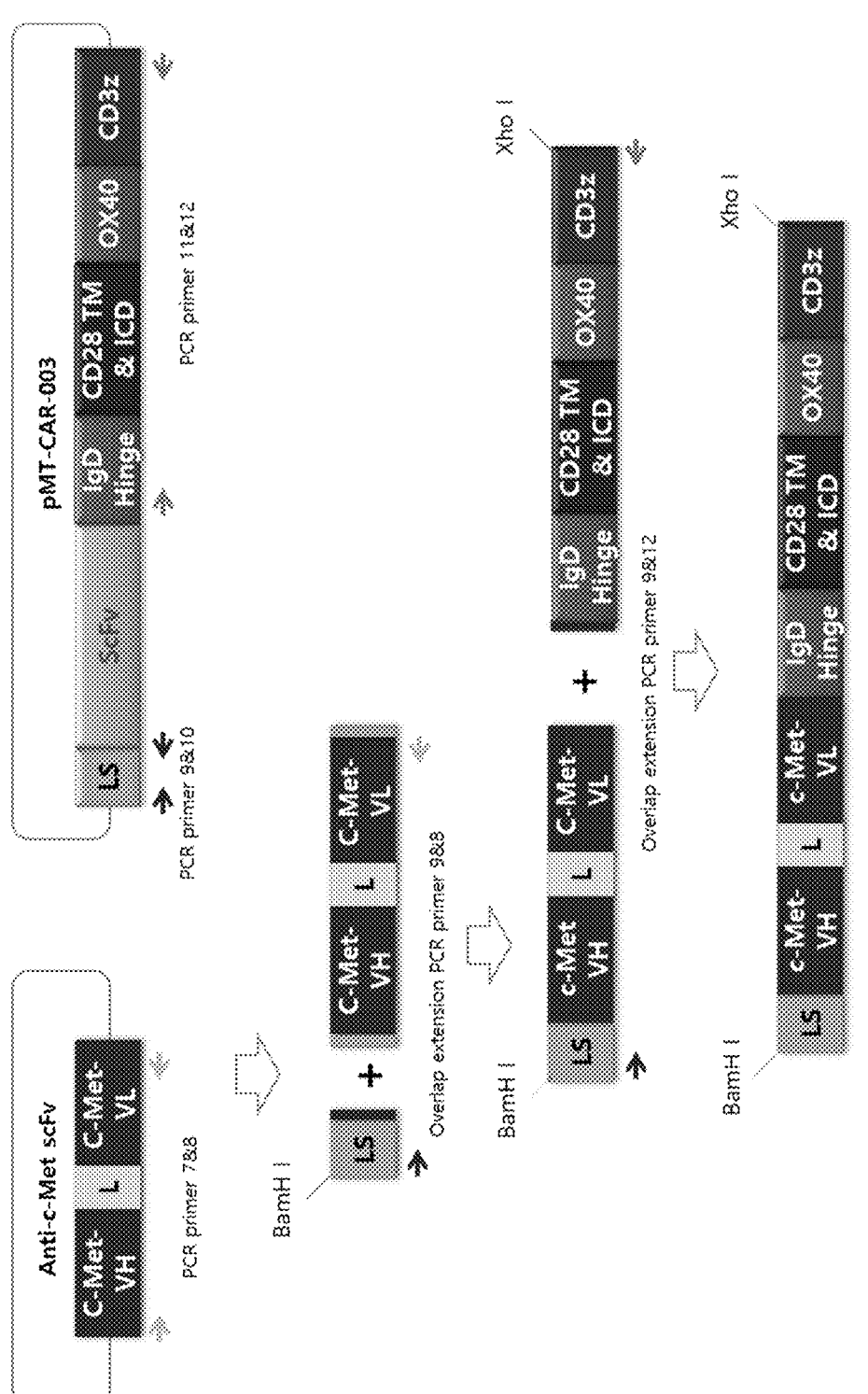
FIG. 10 is a schematic diagram illustrating a PCR amplification procedure for c-Met-CAR-004 according to the present disclosure.
Figure 11:
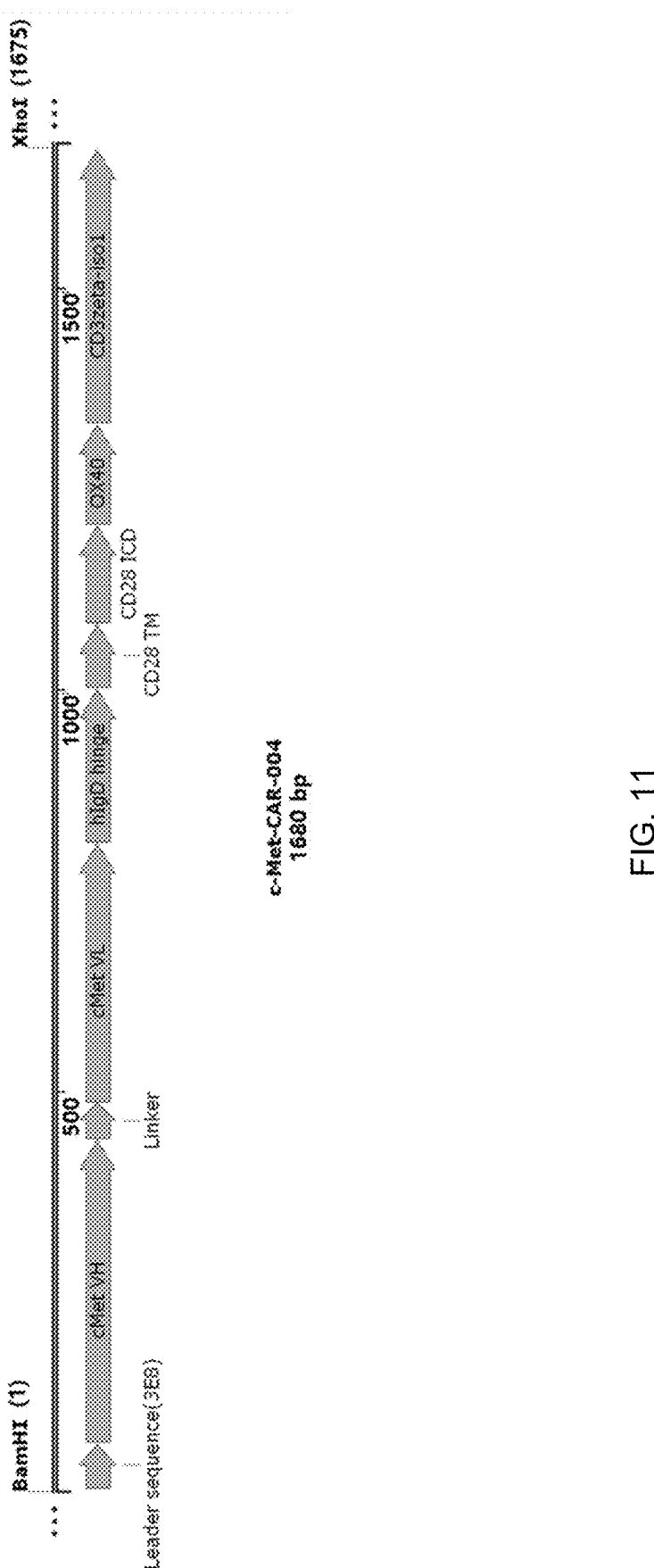
FIG. 11 is a schematic diagram illustrating the structure of c-Met-CAR-004 construct according to the present disclosure.
Figure 12A:
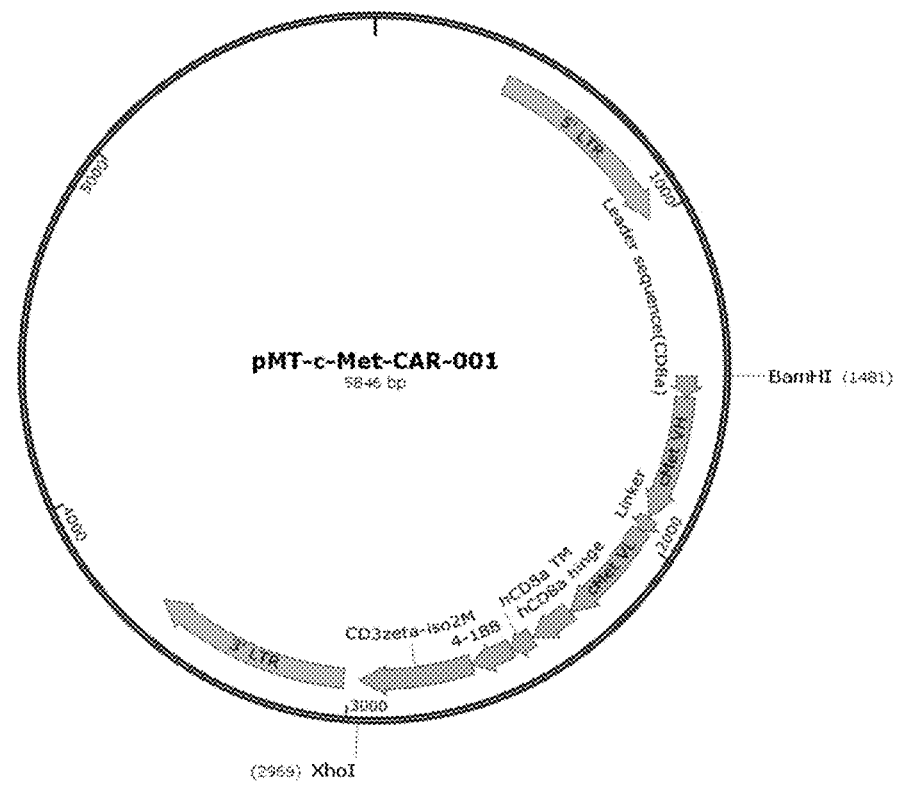
FIGS. 12a, 12b, 12c and 12d are maps illustrating the structures of pMT-c-Met-CAR-001, pMT-c-Met-CAR-002, pMT-c-Met-CAR-003, and pMT-c-Met-CAR-004 plasm ids according to the present disclosure.
Figure 12B:
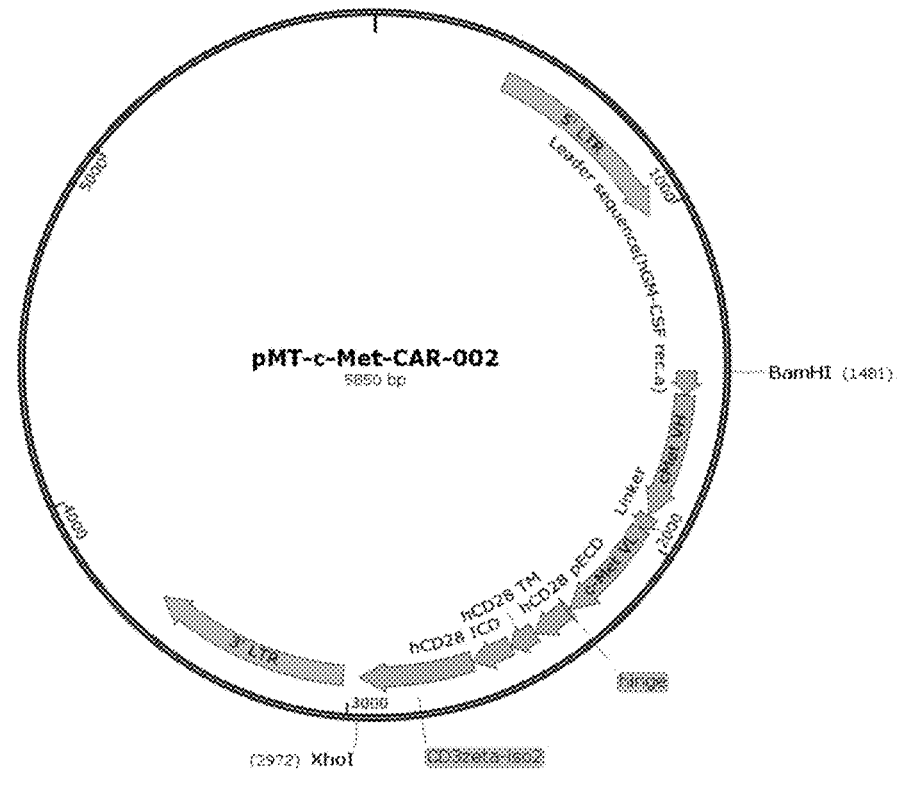
Figure 12C:
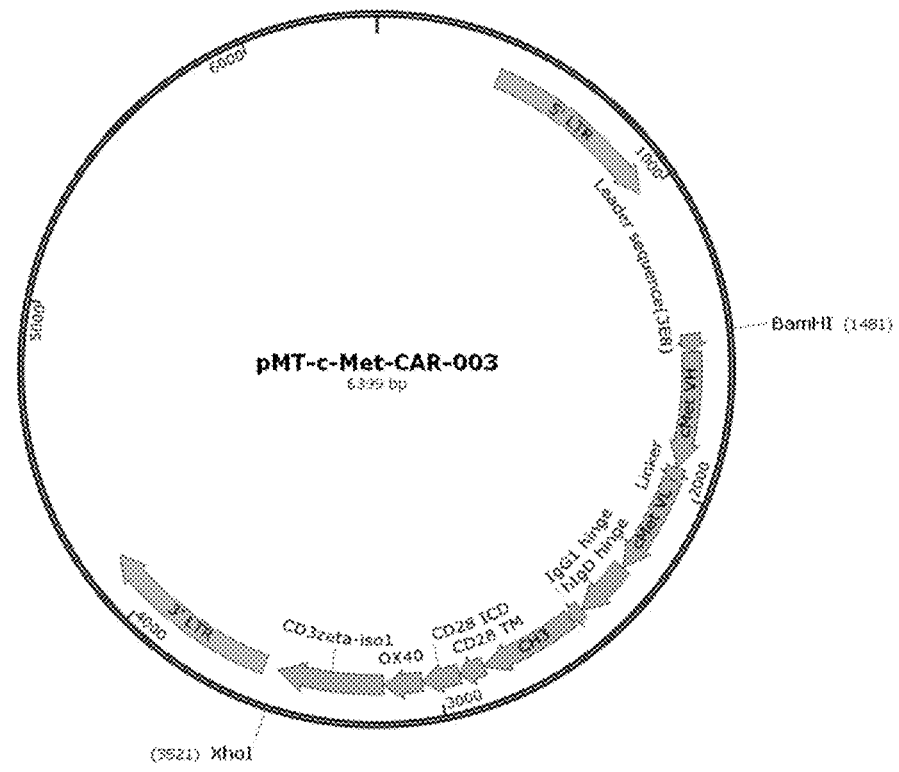
Figure 12D:
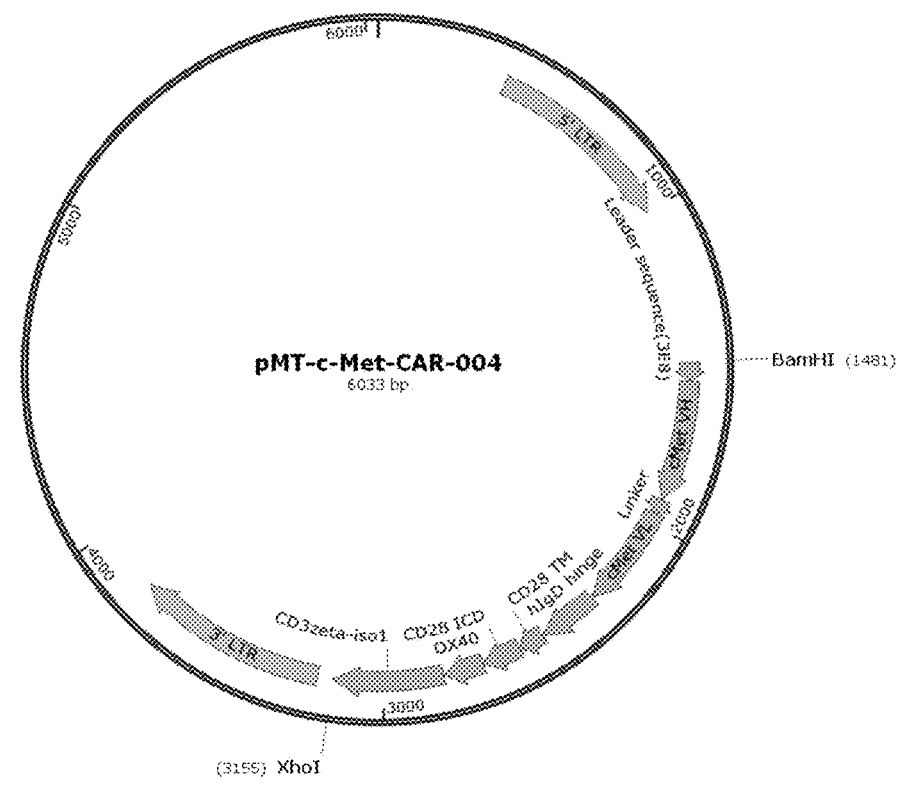

Amplification was performed by OE-PCR (overlap extension PCR) using the primers of SEQ ID NOS: 9 and 8 (Table 3), with the PCR products BamH I-3E8 LS-scFv and 3E8 LS-scFv-hIgD hinge serving as templates. OE-PCR was performed using the primers of SEQ ID NOS: 9 and 12 (Table 3) while the amplicons BamH I-3E8 LS-scFv-hIgD hinge and scFv-IgD hinge-CD28 TM-CD28 ICD-OX40-CDζ3-iso1-Xho I were used as templates (FIG. 10). The PCR product thus obtained had the nucleotide sequence of SEQ ID NO: 63 and was named c-Met-CAR-004 which was structured to include BamH I-3E8 LS-scFv-IgD hinge-CD28 TM-CD28 ICD-OX40-CDζ3-iso1-Xho I (FIG. 11). This PCR product was ligated to pGemT ESAY vector containing poly-T sequences at both ends of the linear DNA to attain pGemT-c-Met-CAR-004 construct. Sequencing analysis with the aid of primers of SEQ ID NOS: 13 and 14 (Table 3) confirmed that the amplicon has the same original sequence.

Example 6. Construction of pMT-c-Met-CAR Retroviral Vector

A single type of pBHA-c-Met-CAR-001 and three types of pGemT-c-Met-CAR vectors (pGemT-c-Met-CAR-002, pGemT-c-Met-CAR-003, pGemT-c-Met-CAR-004) were treated with BamH I and Xho I restriction enzymes to obtain DNA fragments. These DNA fragments were ligated to the pMT retroviral vector (U.S. Pat. No. 6,451,595) previously cut with BamH I and Xho I restriction enzymes to construct four types of pMT-c-Met-CAR retroviral vectors (pMT-c-Met-CAR-001, -002, -003, and -004) (FIGS. 12a to 12d). The pMT-c-Met-CAR retroviral vectors each include a sequence encoding c-Met-CAR under the control of the MLV LTR promoter.

Example 7. Preparation of Anti-c-Met-CAR Gene-Expressing T Cell

Example 7-1. Construction of Anti-c-Met-CAR Gene-Expressing Retrovirus

The retroviruses for anti-c-Met-CAR gene delivery were prepared using plasmid DNA transformation (Soneoka Y et al., 1995). The TransIT 293 transformation system (Mirus Bio LLC, WI, USA) was used and operated according to the manufacturer's protocol. The four types of pMT-c-Met-CAR retroviral vectors, the gag-pol expression vector, and the RD114 env expression vector were transformed into 293T cell lines seeded at a density of $1 \times 10^6$ cells per 60 mm dish on the previous day, and then the cells were incubated for about 48 hours. After completion of the incubation, the cell cultures were all harvested, and then filtered through a 0.45-μm filter. The four types of anti-c-Met-CAR retroviruses thus produced were measured for titer by real-time PCR using a retrovirus titer set kit (TaKaRa, JAPAN), and then stored frozen at −80° C. before use.

Example 7-2. Preparation of Anti-c-Met-CAR Gene-Expressing T Cell

Mononuclear cells were obtained from the blood of a donor by using SepMate™-50 (STEMCELL) and Ficoll-Paque PLUS (GE healthcare, Sweden). The mononuclear cells were dispensed at $1 \times 10^7$ cells in 100-mm dishes while AIMV medium (Invitrogen) supplemented with 5% human serum was used as a culture medium, and then the anti-CD3 (OKT3, eBioscience) antibody was added at 50 ng per mL, thereby activating T cells. For the growth of T cells, human IL-2 (R&D) was added to the culture medium at 300 U per mL, and cultured. After 48-hour incubation, the activated T cells were harvested, and used for delivery of four types of anti-c-Met-CAR retroviruses.

Retronectin (TaKaRa, Japan) prepared at a concentration of 10 μg/mL was added to 6-well plates at 2 mL per well, and then coated on the plates by incubation at room temperature for 2 hours. After the incubation, the residual Retronectin was removed, and then phosphate-buffered saline (PBS) containing 2.5% human serum albumin was added at 2 mL per well, and blocked by incubation at room temperature for 30 minutes. After the incubation, the solution used for blocking was removed, and the wells were washed by addition of HBSS containing 2.5% of 1 M HEPES at 3 mL per well. The anti-c-Met-CAR retroviruses were diluted to $3 \times 10^{10}$ copies per well with AIMV media containing 5% human serum, and 4 mL of the dilution was added, followed by centrifugation under conditions of 2000×g and 32° C. for 2 hours, thereby immobilizing the retroviruses on Retronectin. The same amount of the medium used for retrovirus dilution was added to the wells to be used as a control. After the incubation, the residual retroviruses were removed. Activated T cells were added at $2 \times 10^6$ cells per well, followed by centrifugation at 1000×g for 15 minutes, thereby delivering anti-c-Met-CAR retroviruses to T cells. To increase the delivery efficiency, the delivery procedure was repeated once more the next day, and thus a total of 2 rounds of delivery was performed. After 24 hours of delivery, the T cells were all harvested, and subcultured in T flasks at $5 \times 10^5$ cells per mL with AIMV media containing 5% human serum and 300 U/mL human IL-2. The cells were passaged at $5 \times 10^5$ cells per mL every 3-4 days, and maintained so as not to exceed $2 \times 10^6$ cells per mL.

Figure 13A:
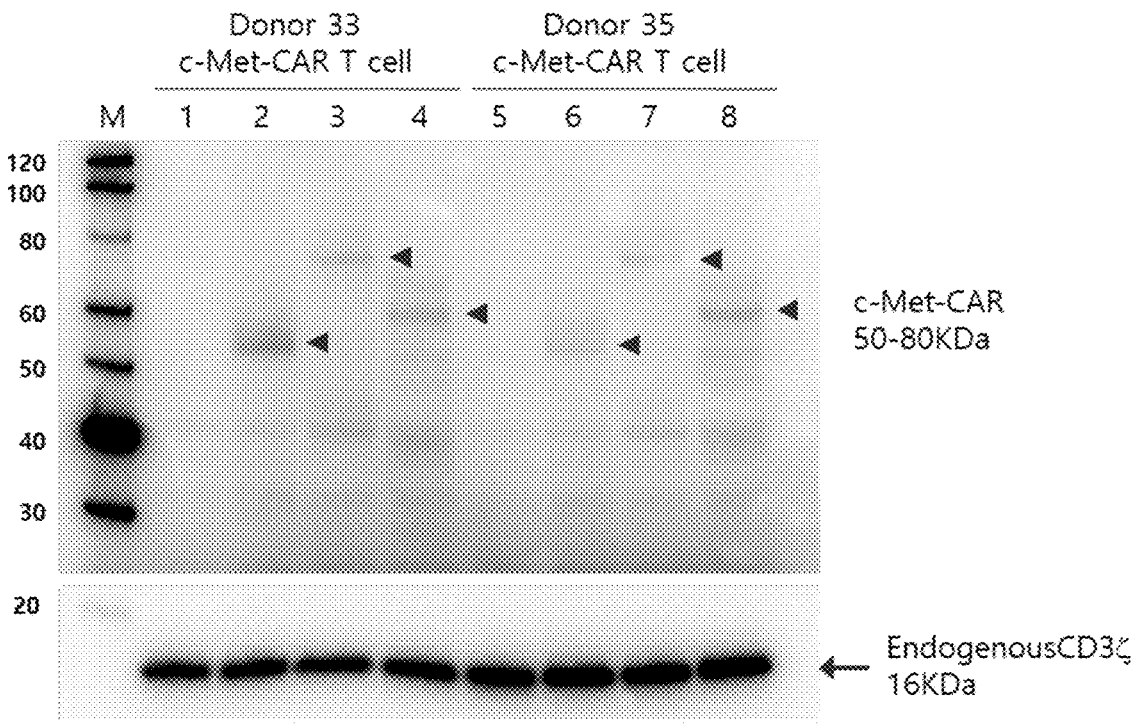
FIGS. 13a, 13b and 13c are views illustrating the CAR expression as confirmed by the expression of CD3 zeta in the anti-c-Met-CAR-expressing T cells according to the present disclosure.
Figure 13B:
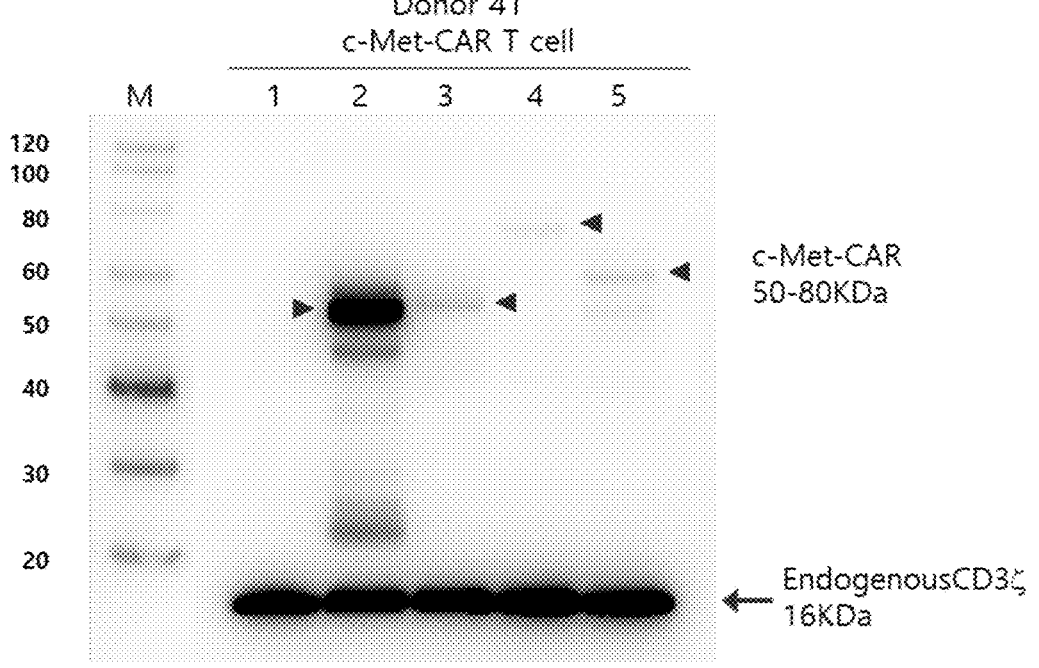
Figure 13C:
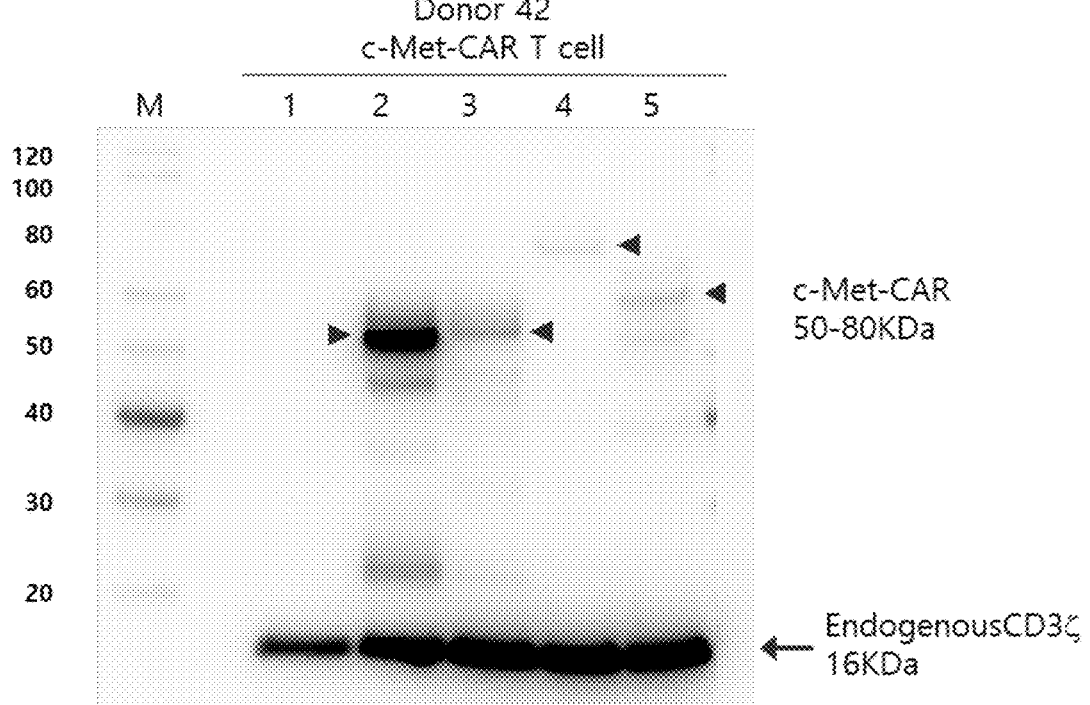

Next, it was investigated whether the anti-c-Met-CAR was expressed in the activated T cells (anti-c-Met-CAR-expressing T cells) to which the anti-c-Met-CAR retroviruses had been delivered. Proteins were extracted from $2 \times 10^6$ cells harvested, and quantitatively analyzed by the Bradford assay. The proteins were mixed with a 4× sample buffer (Invitrogen) and dithiothreitol and then boiled at 95° for 5 minutes for reduction. The expression of anti-c-Met-CAR was confirmed by western blotting. To this end, mouse anti-human CD247 (BD, CA, USA) was used as a primary antibody against CD3ζ while goat anti-mouse IgG(H+L)-HRP (Thermo, USA) was used as a secondary antibody. The western blotting analysis for the four types of anti-c-Met-CAR-expressing T cells detected a band at 50-80 KDa in each cell, demonstrating the expression of anti-c-Met-CAR (FIGS. 13a to 13c).

Figure 14:
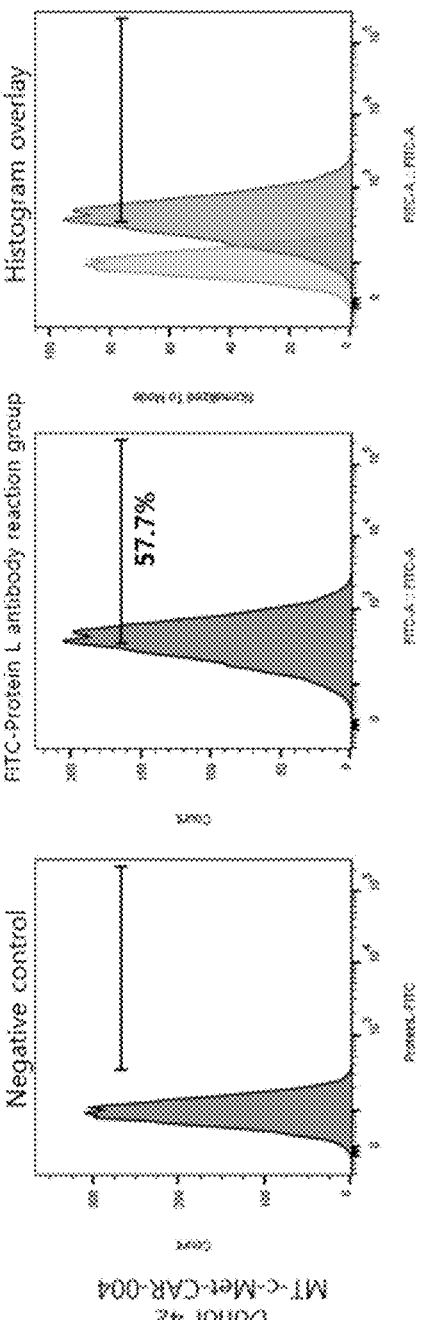
FIG. 14 are views illustrating the CAR expression on the surface of the anti-c-Met-CAR-expressing T cells according to the present disclosure.
Figure 15A:
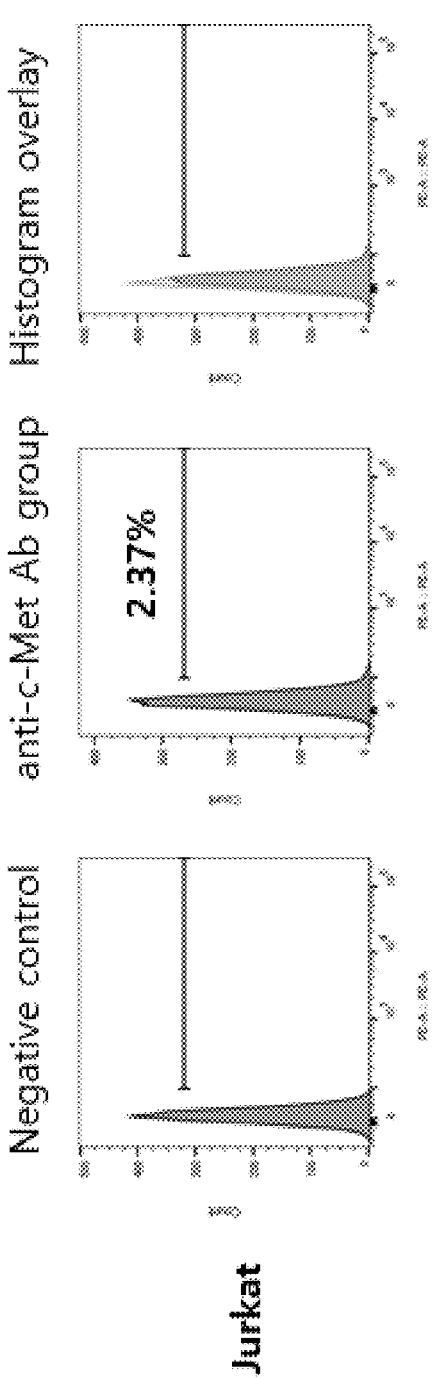
FIGS. 15a, 15b, 15c, 15d, 15e and 15f are views illustrating c-Met expression levels in the cancer cell lines A549, PC-3, MCF-7, SKOV3, SK-HEP-1, and Jurkat.
Figure 15B:
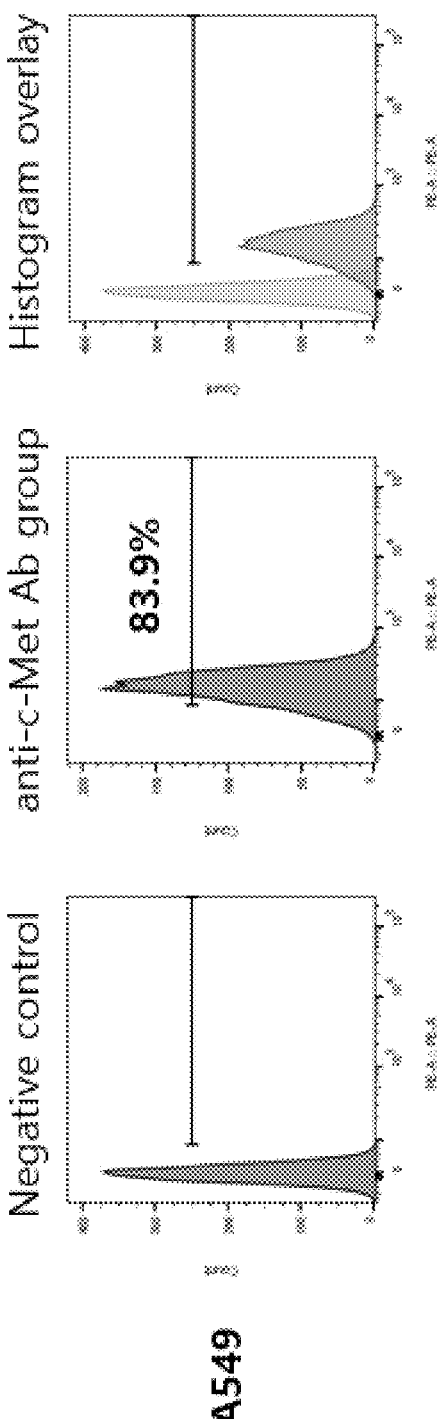
Figure 15C:
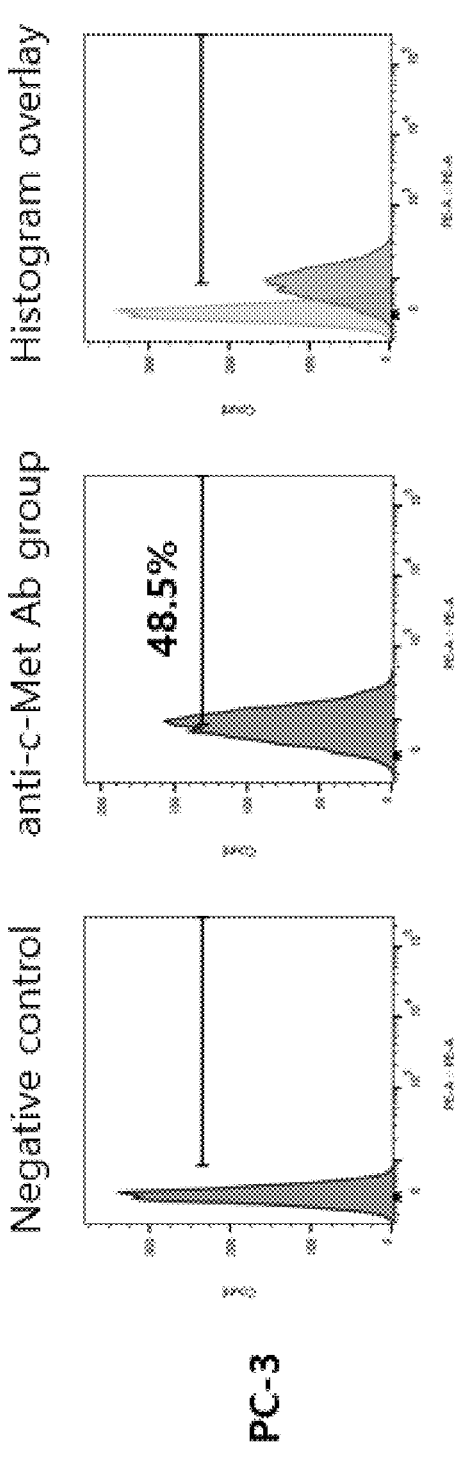
Figure 15D:
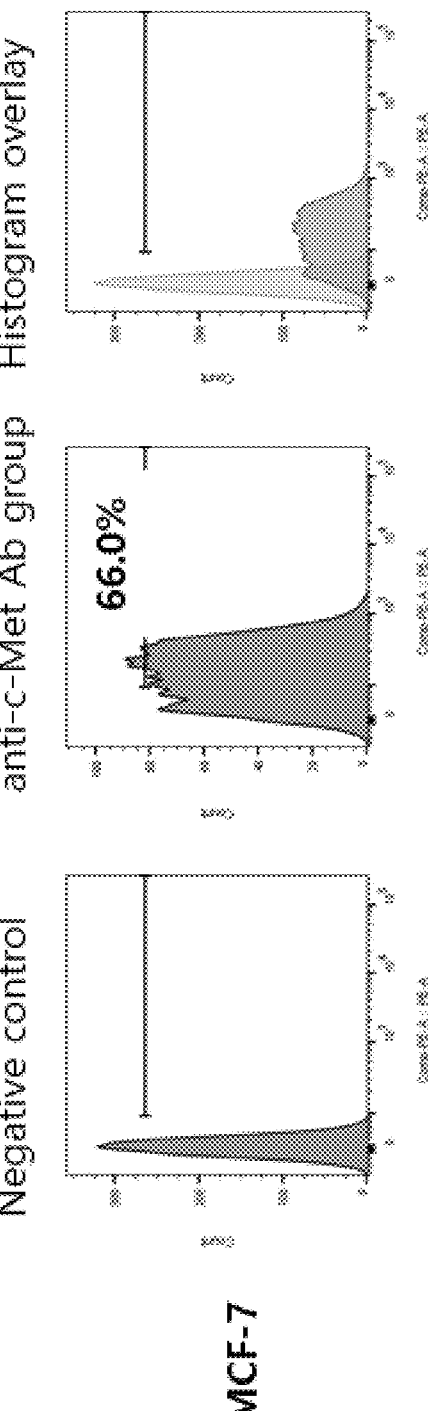
Figure 15E:
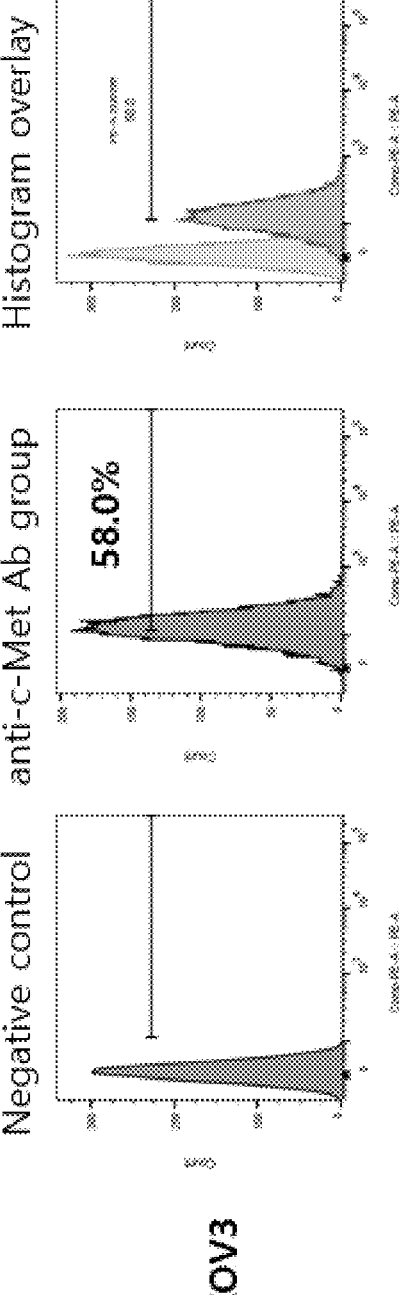
Figure 15F:
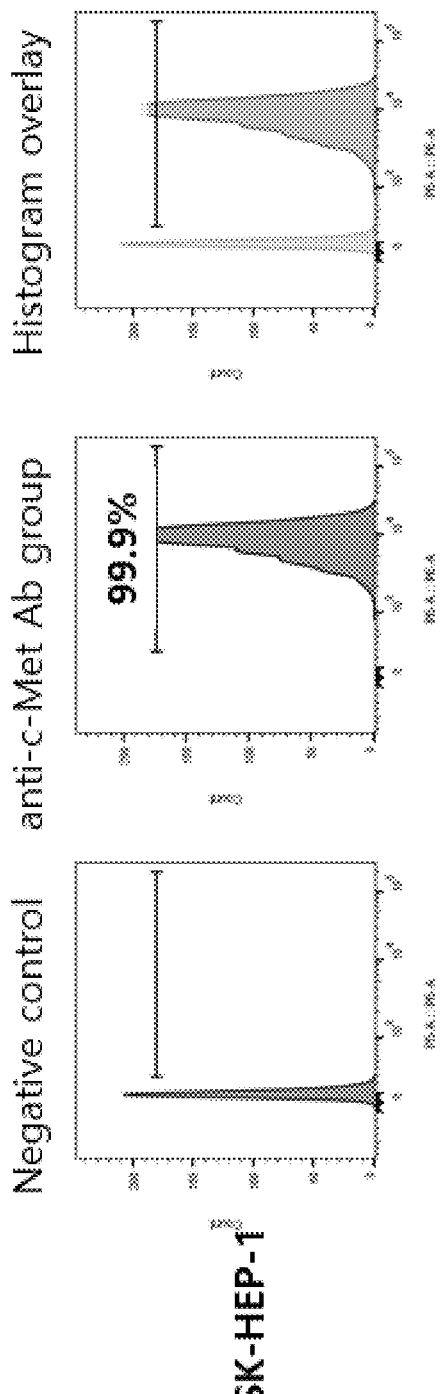
Figure 16A:
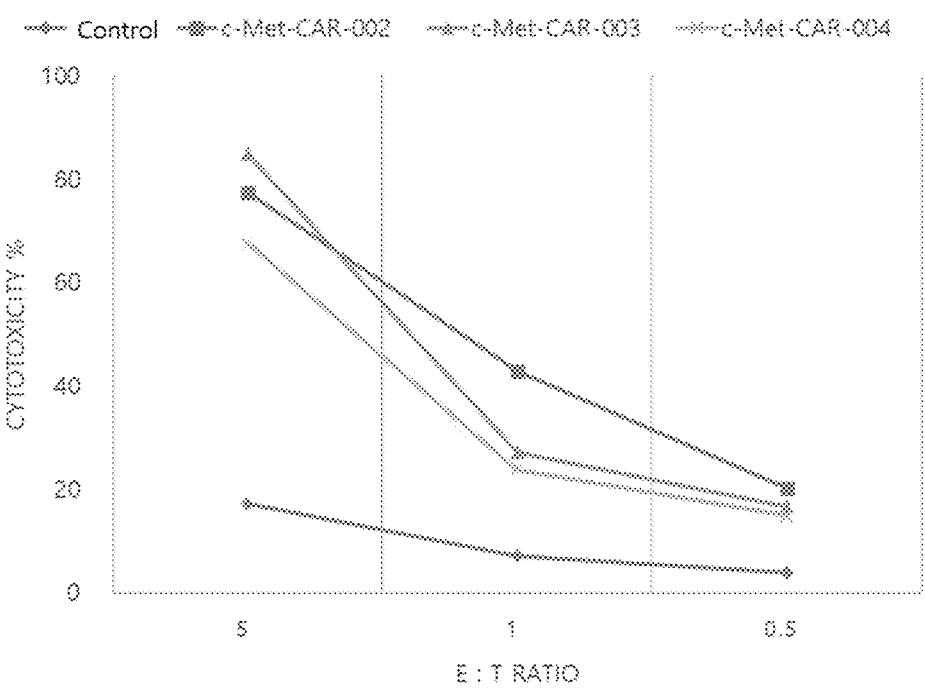
FIGS. 16a, 16b, 16c and 16d are plots illustrating anti-cancer activity of the anti-c-Met CAR-expressing T cells according to the present disclosure against A549 cancer cell line.
Figure 16B:
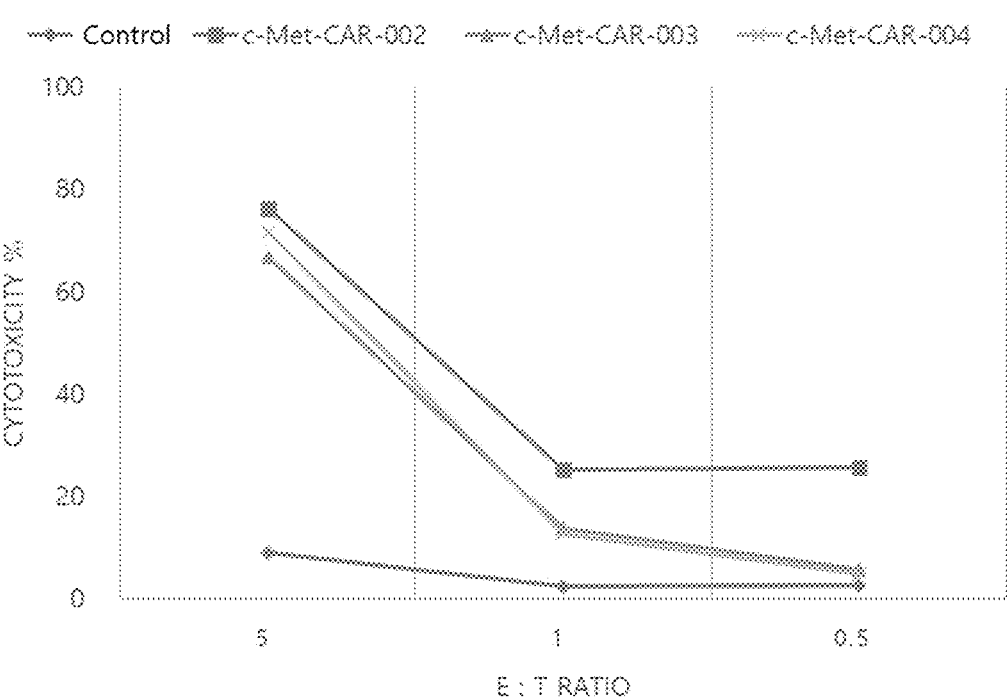
Figure 16C:
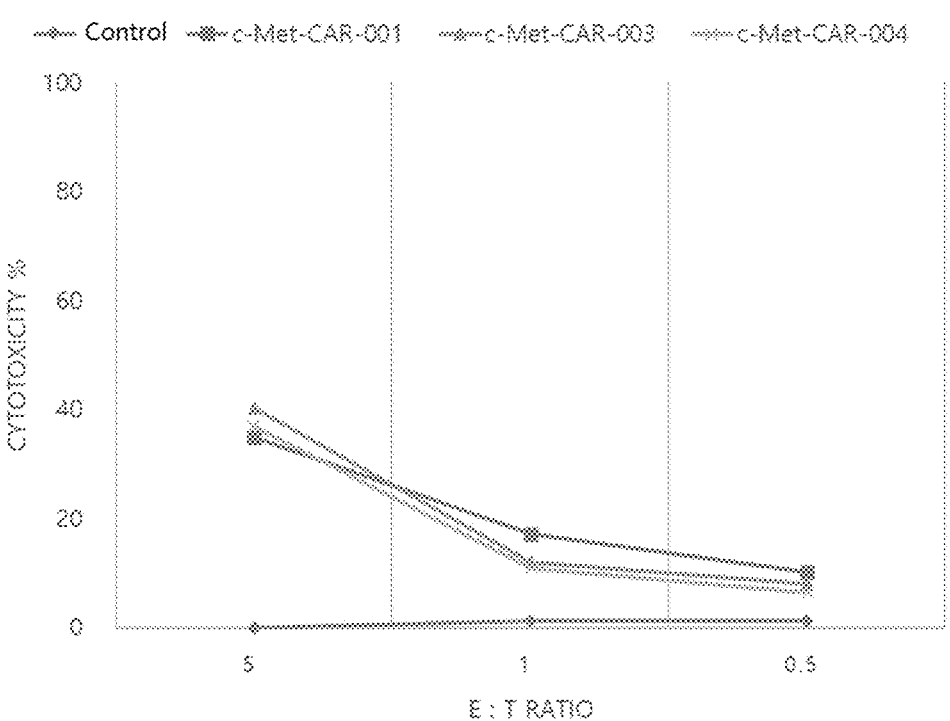
Figure 16D:
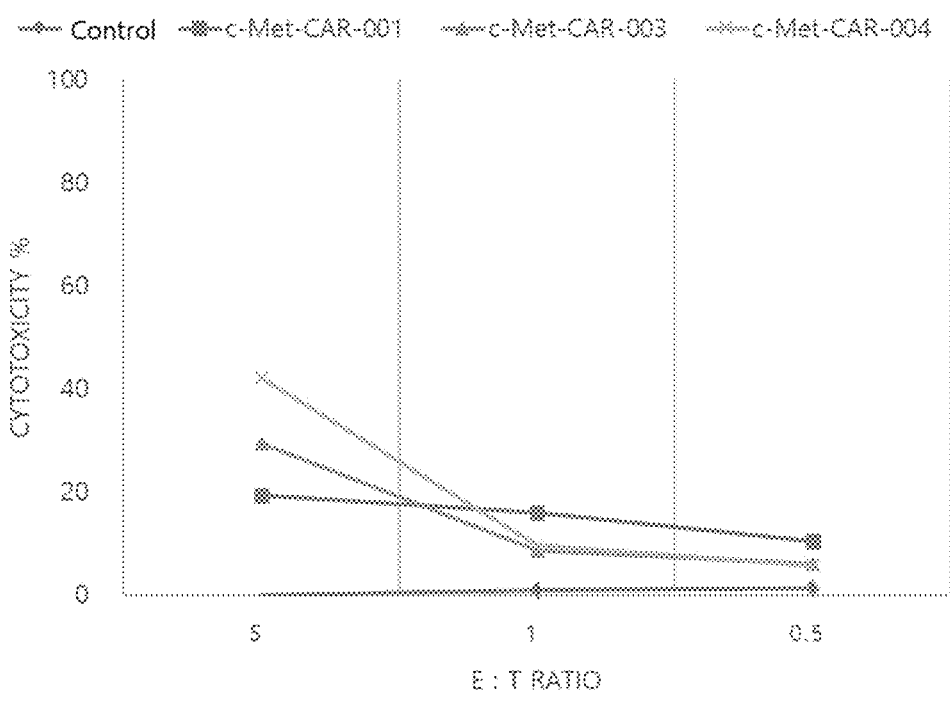
Figure 17A:
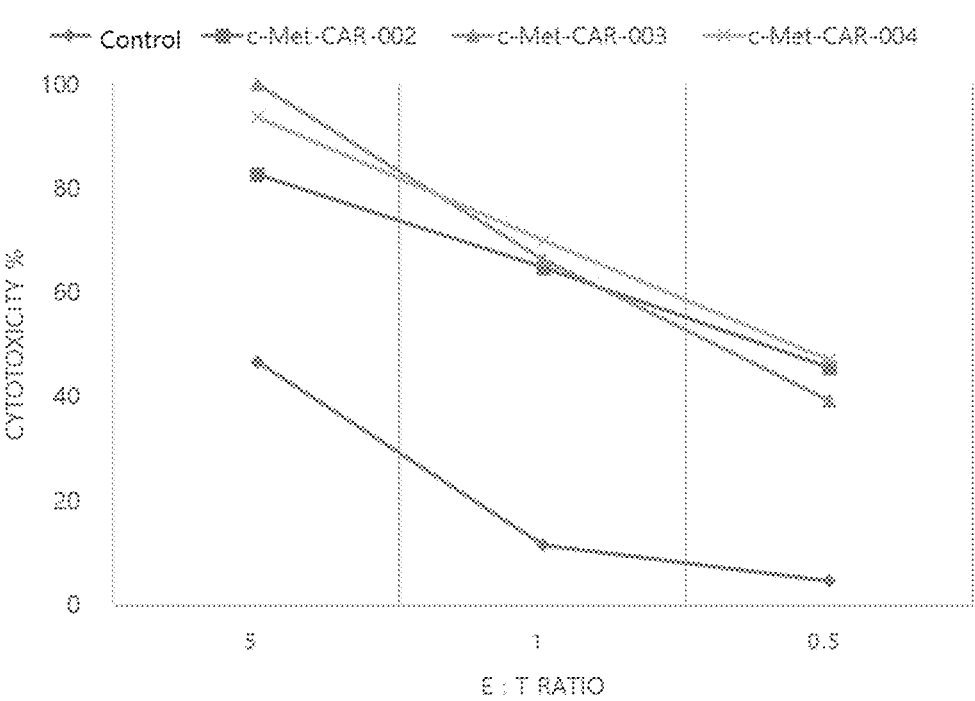
FIGS. 17a, 17b, 17c and 17d are plots illustrating anti-cancer activity of the anti-c-Met CAR-expressing T cells according to the present disclosure against PC-3 cancer cell line.
Figure 17B:
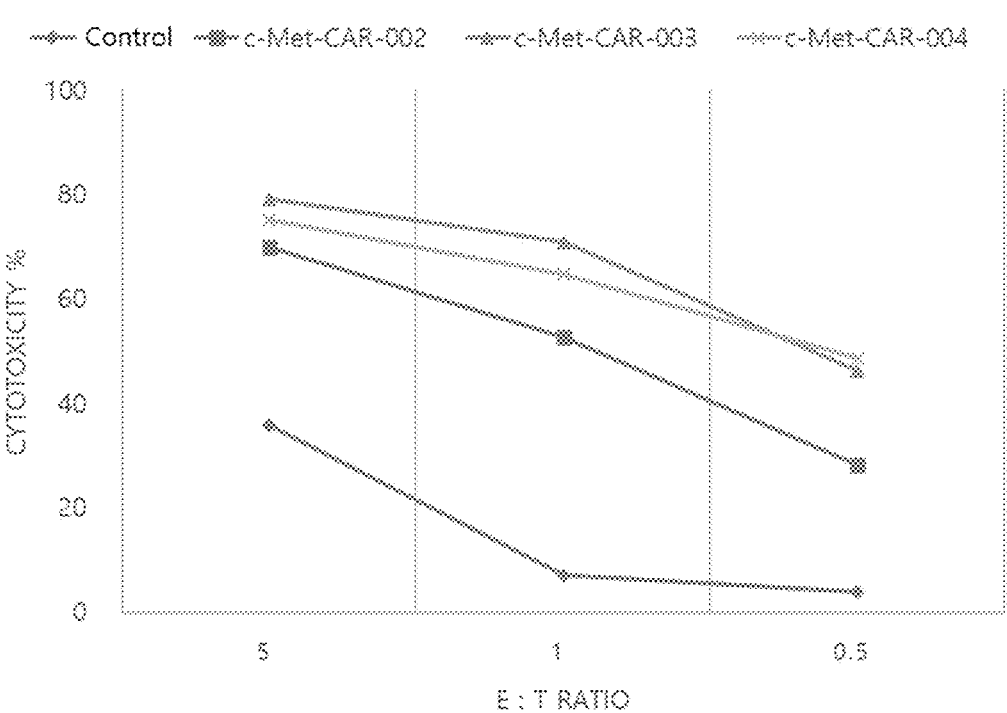
Figure 17C:
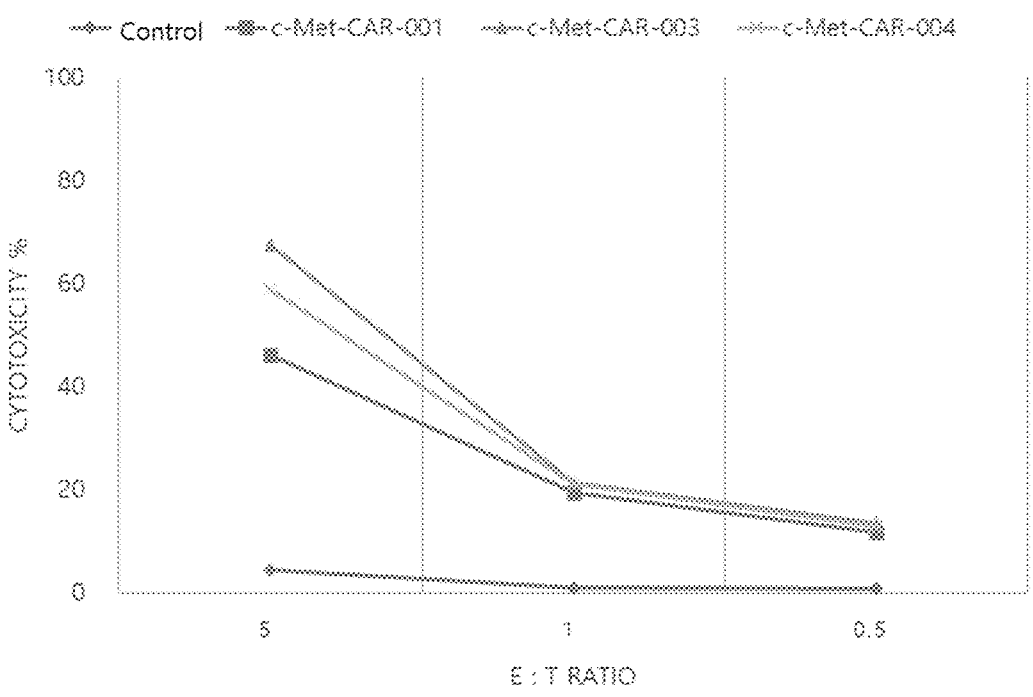
Figure 17D:
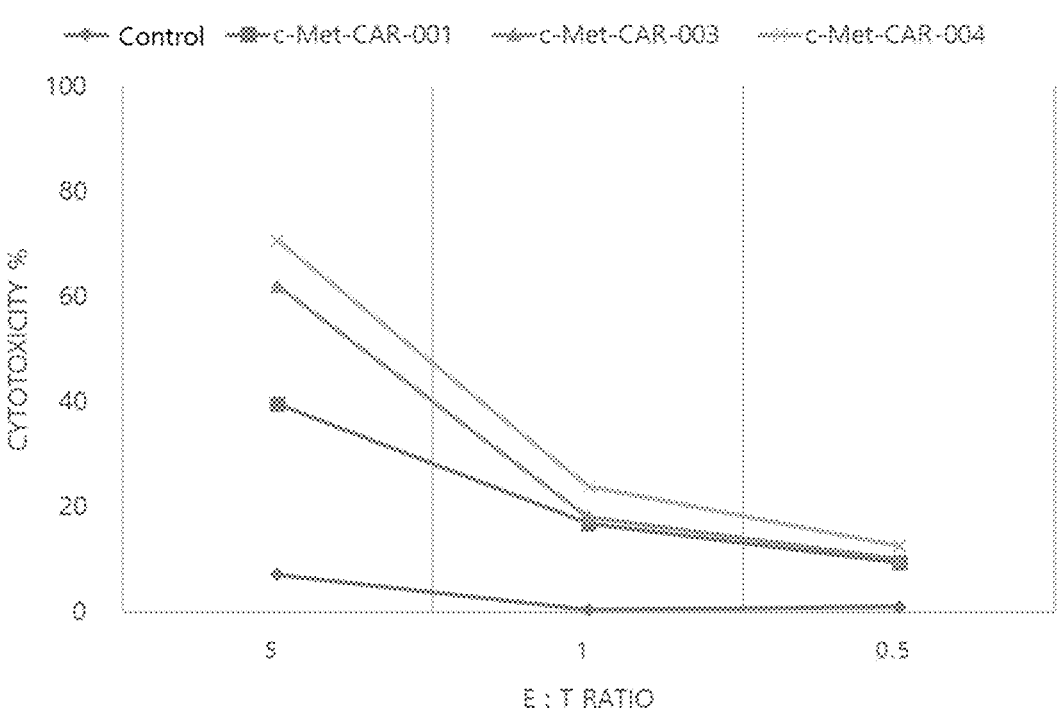
Figure 18A:
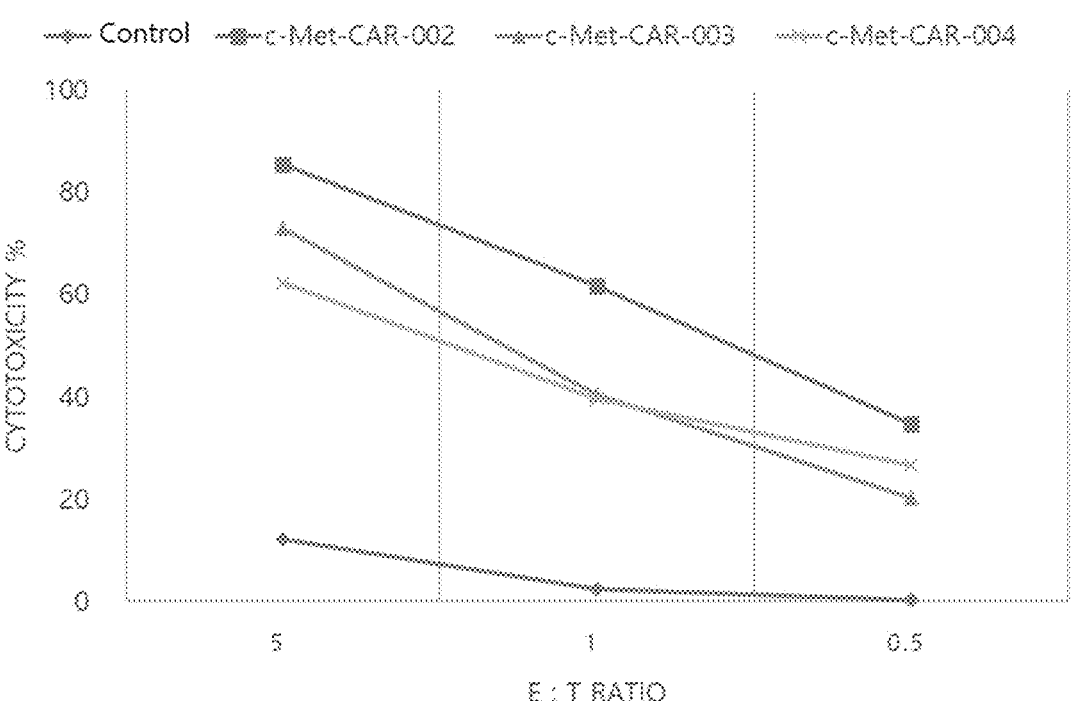
FIGS. 18a, 18b, 18c and 18d are plots illustrating anti-cancer activity of the anti-c-Met CAR-expressing T cells according to the present disclosure against MCF-7 cancer cell line.
Figure 18B:
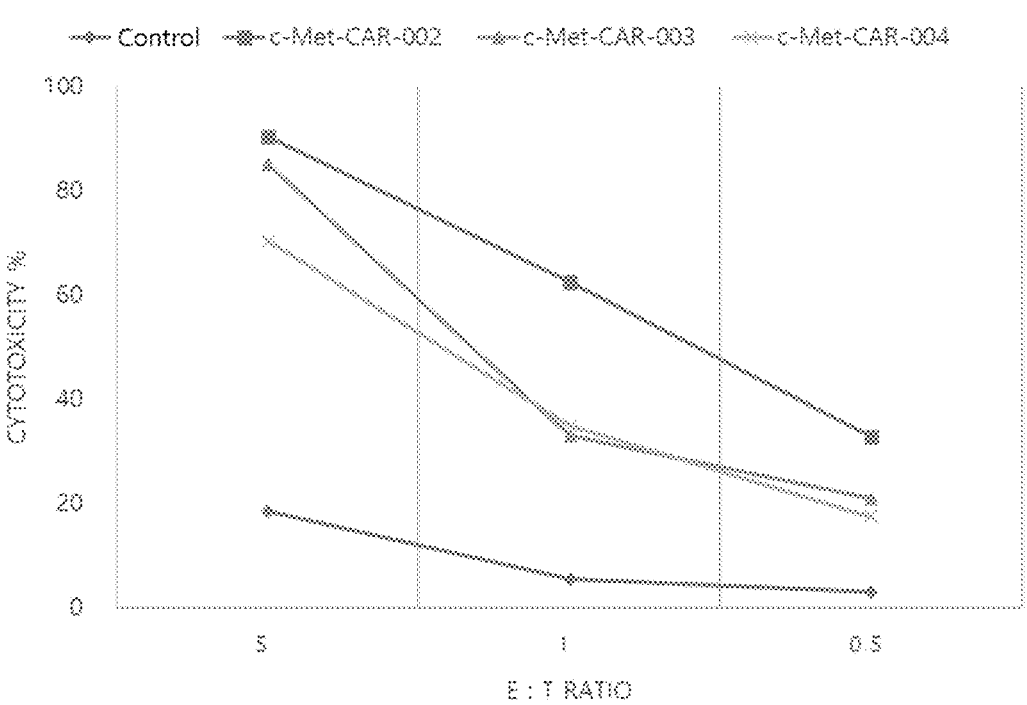
Figure 18C:
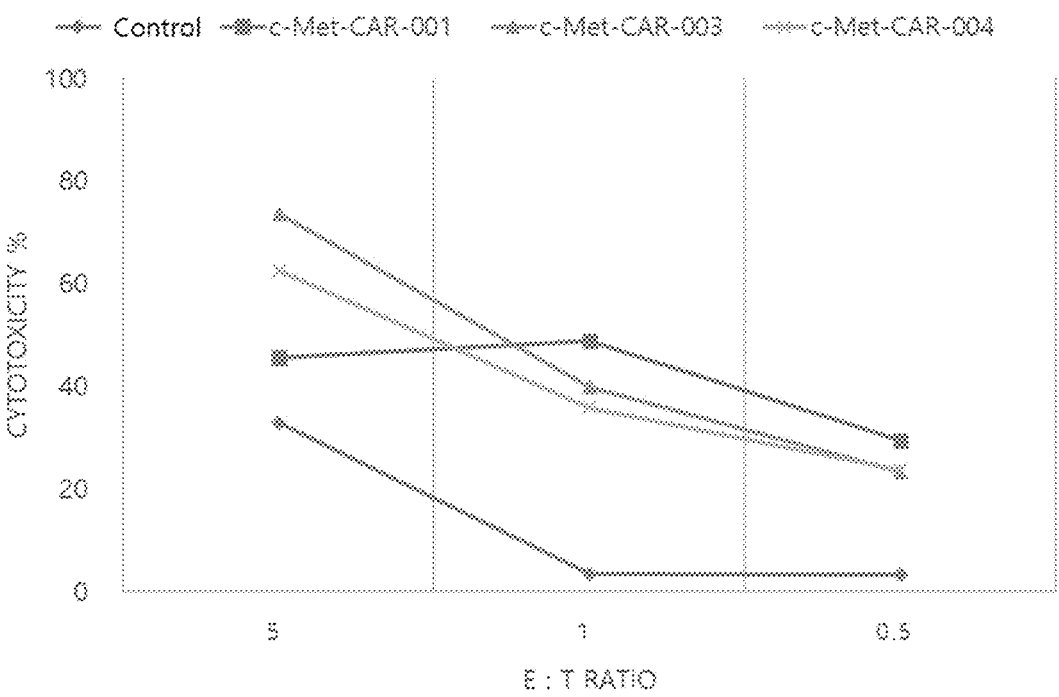
Figure 18D:
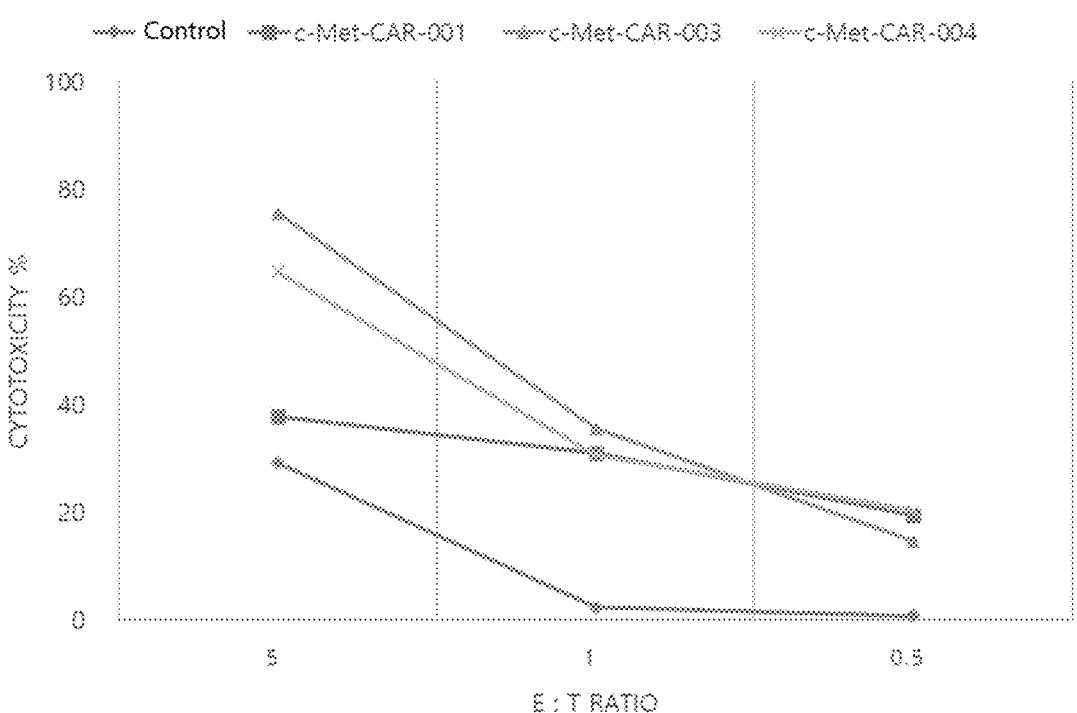
Figure 19A:
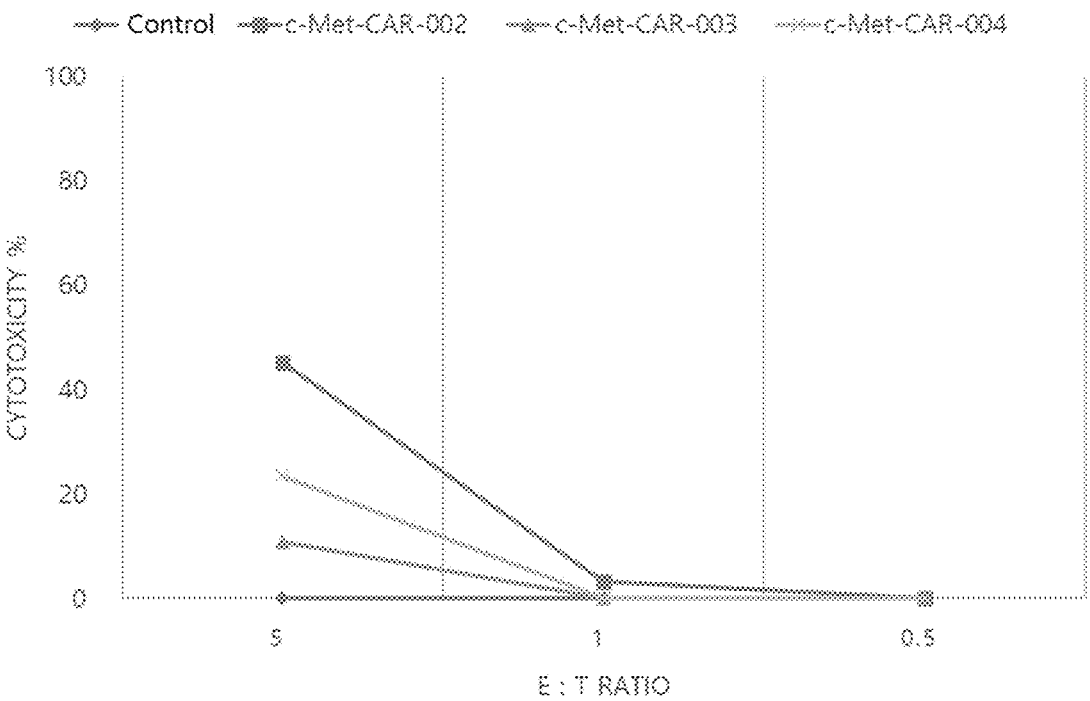
FIGS. 19a. 19b, 19c and 19d are plots illustrating anti-cancer activity of the anti-c-Met CAR-expressing T cells according to the present disclosure against SKOV3 cancer cell line.
Figure 19B:
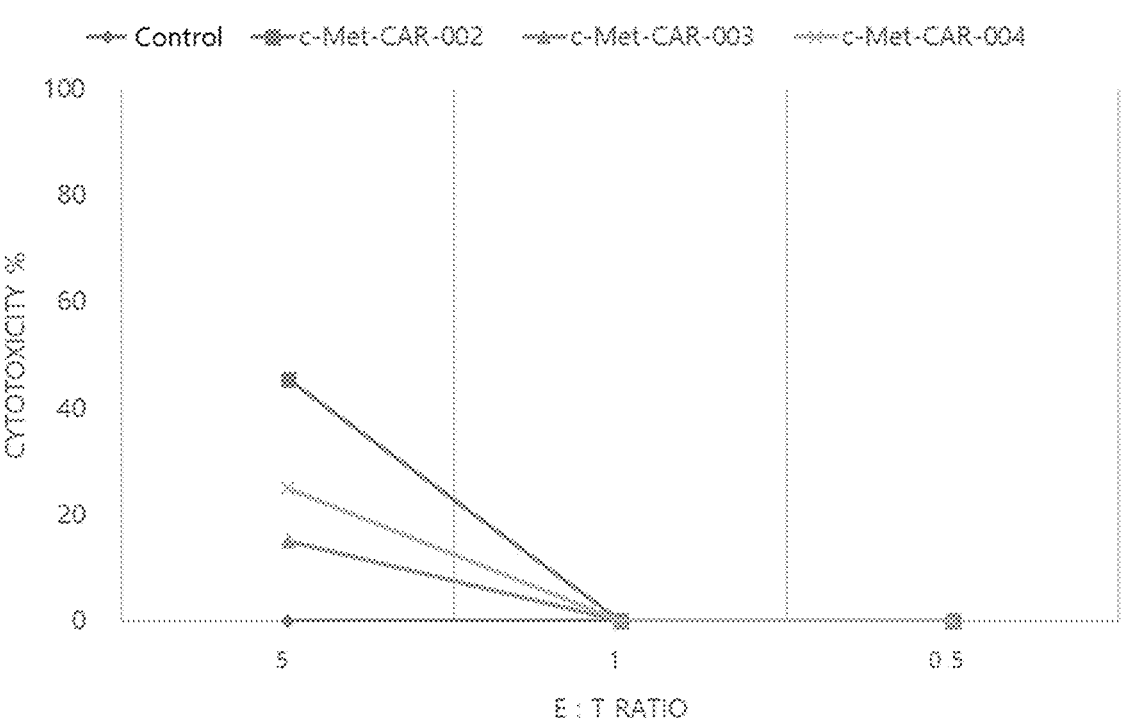
Figure 19C:
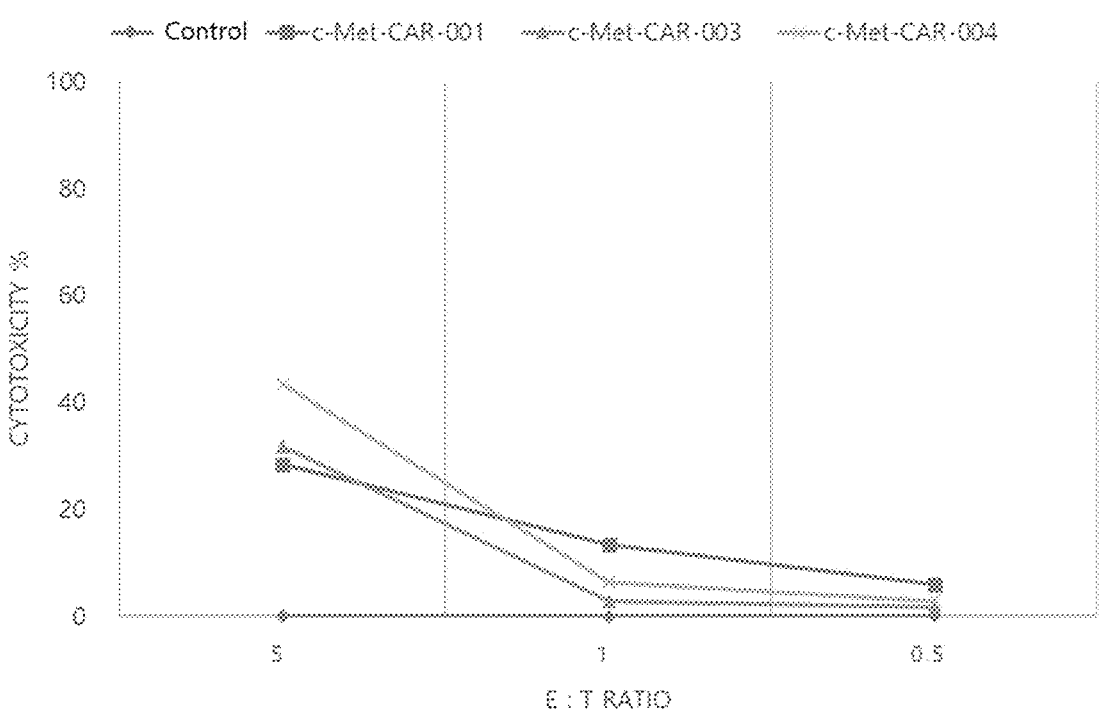
Figure 19D:
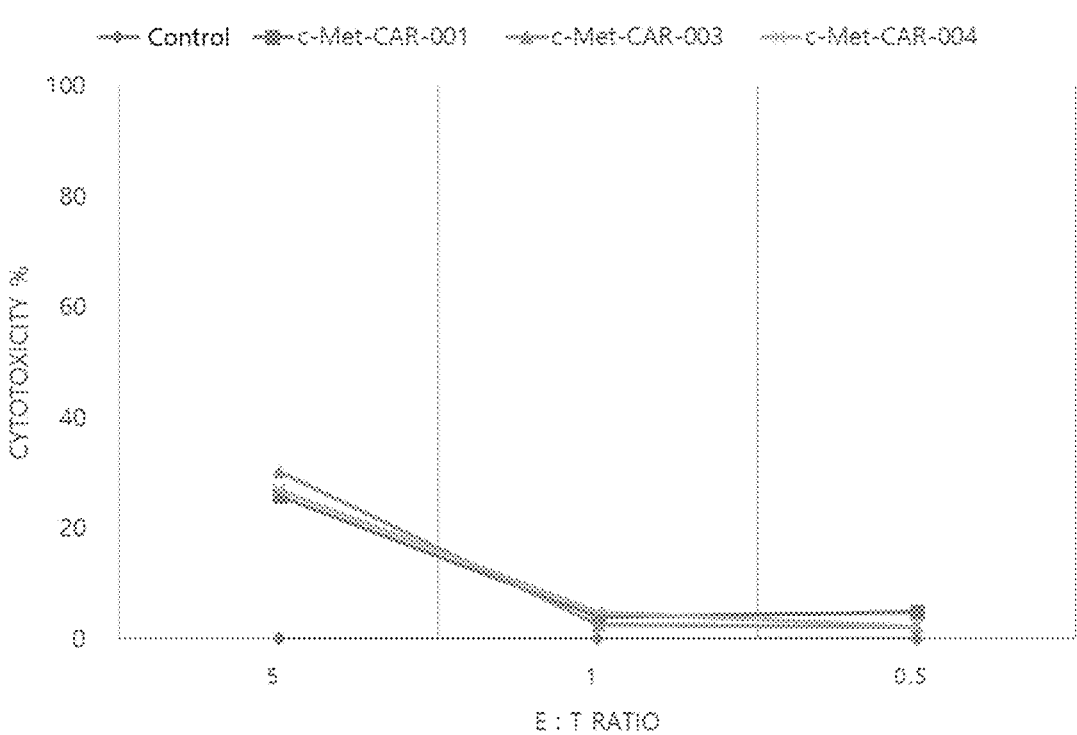

It was investigated whether the anti-c-Met-CAR-expressing T cells expressed anti-c-Met-CAR on the surface thereof. After being harvested, $5×10^5$ cells were washed twice with PBS (phosphate buffered saline) and incubated at 4° C. for 30 minutes with 2.5 μg of FITC-conjugated Protein L (AcroBiosystem, RPL-PF141), which binds specifically to the single-chain variable fragment of CAR. After incubation, the cells were washed twice with PBS and analyzed for the expression of the anti-c-Met-CAR by flow cytometry. As a result, about 57.7% of the T cells to which MT-c-Met-CAR-004 retrovirus had been transfected were observed to have the anti-c-Met-CAR expressed on the surface thereof (FIG. 14).

Example 8. In Vitro Assay For Anticancer Activity of Anti-c-Met-CAR-Expressing T Cell

Example 8-1. Assay For Expression Rate of c-Met on Target Cell

The lung cancer cell line A549 is known to express c-Met at a high level and as such, exhibits adequacy for examining the anticancer activity of the anti-c-Met-CAR-expressing T cells. In this regard, $5×10^5$ A549 cells in 100 μL of PBS was incubated with 1 μg of 1E4-H4k2 antibody at 4° C. for 30 minutes. After incubation, the cells were washed twice with PBS and reacted with 2 μL of goat anti-human IgG-PE (Southern Biotech) at 4° C. for 30 minutes. Thereafter, the cells were washed twice with PBS and analyzed for c-Met expression by flow cytometry. As a result, the A549 cancer cells were observed to exhibit a c-Met expression rate of about 83.9%. In the same manner, c-Met was measured to be expressed at a rate of about 48.5% in the human prostate cancer cell line PC-3, about 66.0% in the human breast cancer cell line MCF-7, about 58.0% in the ovarian cancer cell line SKOV3, about 99.9% in the human liver adeno-carcinoma cell line SK-HEP-1, and about 2.37% in the human acute T cell leukemia cell line Jurkat.

Example 8-2. Assay For Anticancer Activity Using CellTox™ Green Dye

To investigate the anticancer activity of the anti-c-Met-CAR-expressing T cells (effector cells, E) on target cells (T), CellTox™ Green dye was used. CellTox™ Green dye is a dye that attaches to DNA released from dead cells to exhibit fluorescence, and is used to investigate anticancer activity (cytotoxicity). The target cells were prepared at a density of $1×10^4$ cells per 50 μL of a culture medium, and added with 0.2 μL of CellTox™ Green dye, and the mix was seeded to 96-well black plates. The anti-c-Met-CAR-expressing T cells were prepared at a density of $5×10^3$, $1×10^4$, or $5×10^4$ cells (E:T ratio=0.5, 1, and 5) in 50 μL of AIMV medium containing human serum and human IL-2, and added to wells containing the target cells, followed by incubation in a $CO_2$ incubator at 37° C. for 24 hours. The group added with only anti-c-Met-CAR-expressing T cells was prepared in the wells containing CellTox™ Green dye and the target cell culture medium, and the reaction value of the dye, occurring by attachment to DNA released from dead anti-c-Met-CAR-expressing T cells during the incubation was excluded. The wells containing only target cells were prepared to correct the low control (spontaneous DNA release) value, and a lysis solution was added to the well containing only the target cells to correct the high control (maximum DNA release) value. The cytotoxicity on the target cells was calculated by the following equation.

$$\text{Cytotoxicity \%} = \{(\text{Reaction value of Target cells and Effector cells}) - (\text{Reaction value of Effector cells})\} - (\text{Low control})/(\text{High control} - \text{Low control}) × 100 \qquad \text{Equation}$$

As a result, four types of T cells expressing c-Met-CAR-001, -002, -003, and -004 showed high cytotoxicity against A549 cancer cells, compared with T cells expressing no anti-c-Met-CAR (FIG. 16).

In the same assay manner, cytotoxicity against PC-3 cancer cells was confirmed. T cells expressing c-Met-CAR-001, -002, -003, and -004 were observed to exhibit higher anticancer activity against PC-3 cells, compared with T cells expressing no anti-c-Met-CAR (FIG. 17). Particularly, c-Met-CAR-001 was inferior to the other CAR structures in terms of cytotoxic effect.

In the same assay manner, cytotoxicity against MCF-7 cancer cells was confirmed. T cells expressing c-Met-CAR-001, -002, -003, and -004 were observed to exhibit higher anticancer activity against MCF-7 cells, compared with T cells expressing no anti-c-Met-CAR (FIG. 18).

In the same assay manner, cytotoxicity against SKOV3 cancer cells was confirmed. T cells expressing c-Met-CAR-001, -002, -003, and -004 were observed to exhibit higher anticancer activity against SKOV3 cells, compared with T cells expressing no anti-c-Met-CAR (FIG. 19).

Figure 20:
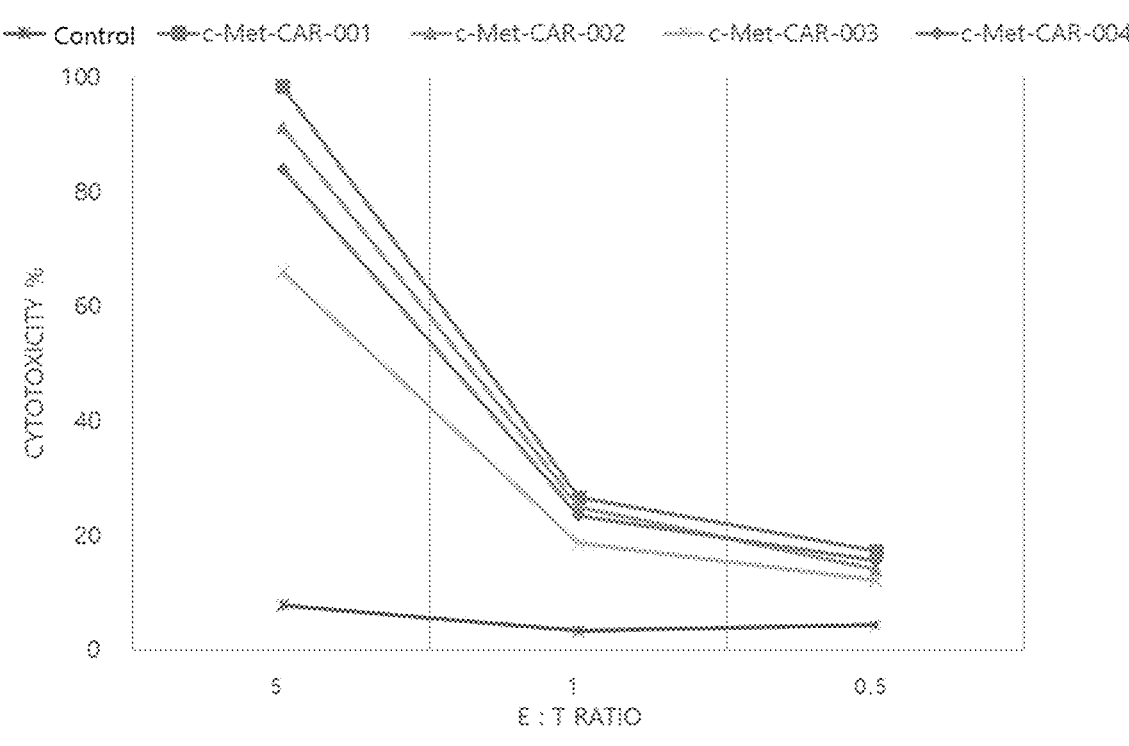
FIG. 20 is a plot illustrating anticancer activity of the anti-c-Met CAR-expressing T cells according to the present disclosure against SK-HEP-1 cancer cell line.

In the same assay manner, cytotoxicity against SK-HEP-1 was confirmed. T cells expressing c-Met-CAR-001, -002, -003, and -004 were observed to exhibit higher anticancer activity against SK-HEP-1 cancer cells, compared with T cells expressing no anti-c-Met-CAR (FIG. 20).

Figure 21A:
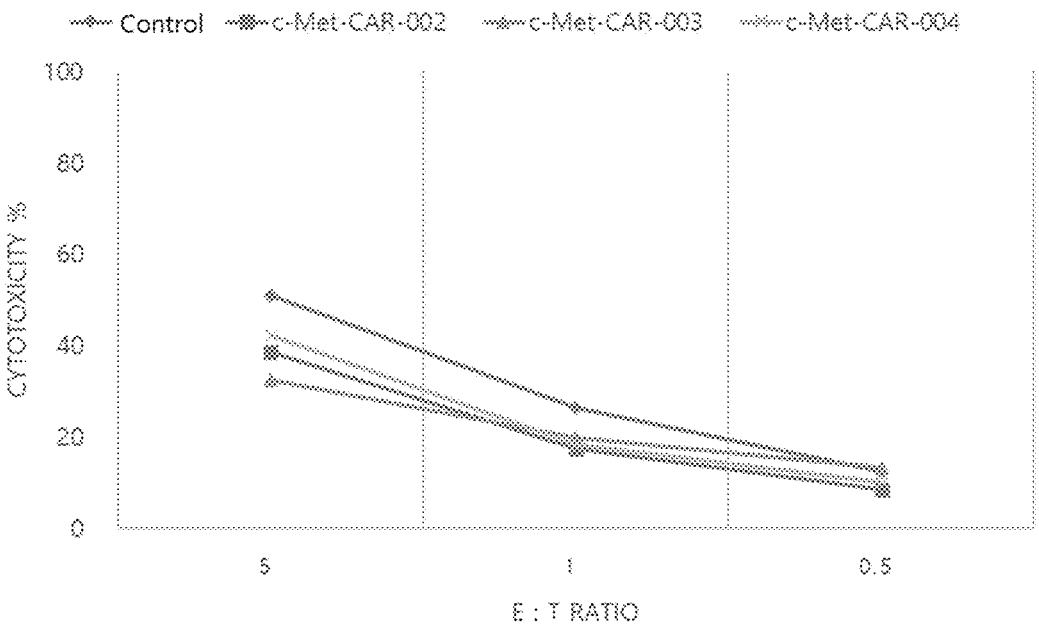
FIGS. 21a, 21b and 21c are plots illustrating anticancer activity of the anti-c-Met CAR-expressing T cells according to the present disclosure against Jurkat cell line.
Figure 21B:
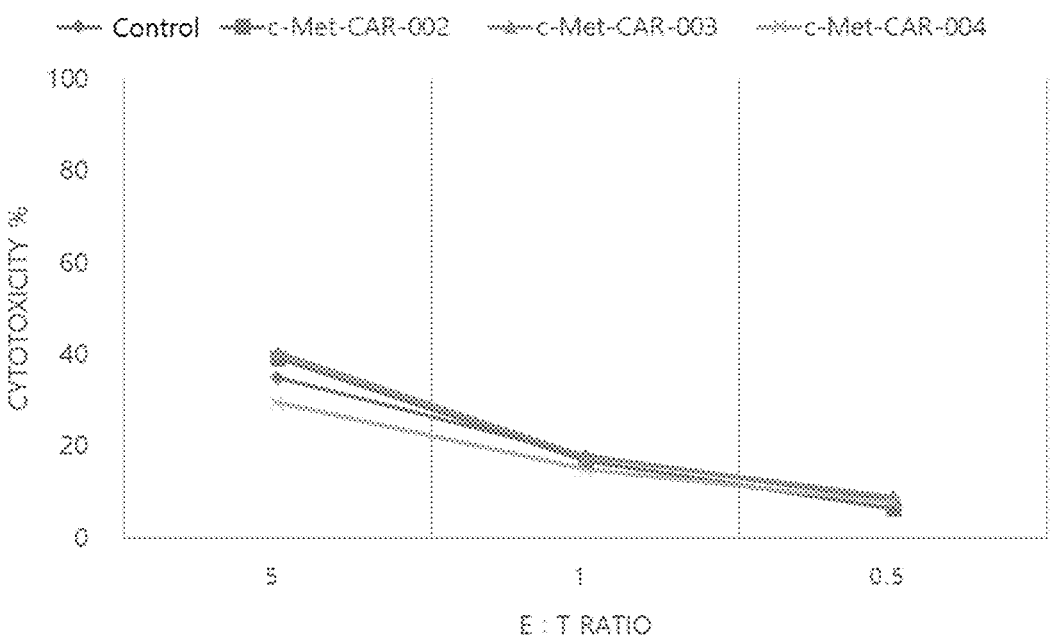
Figure 21C:
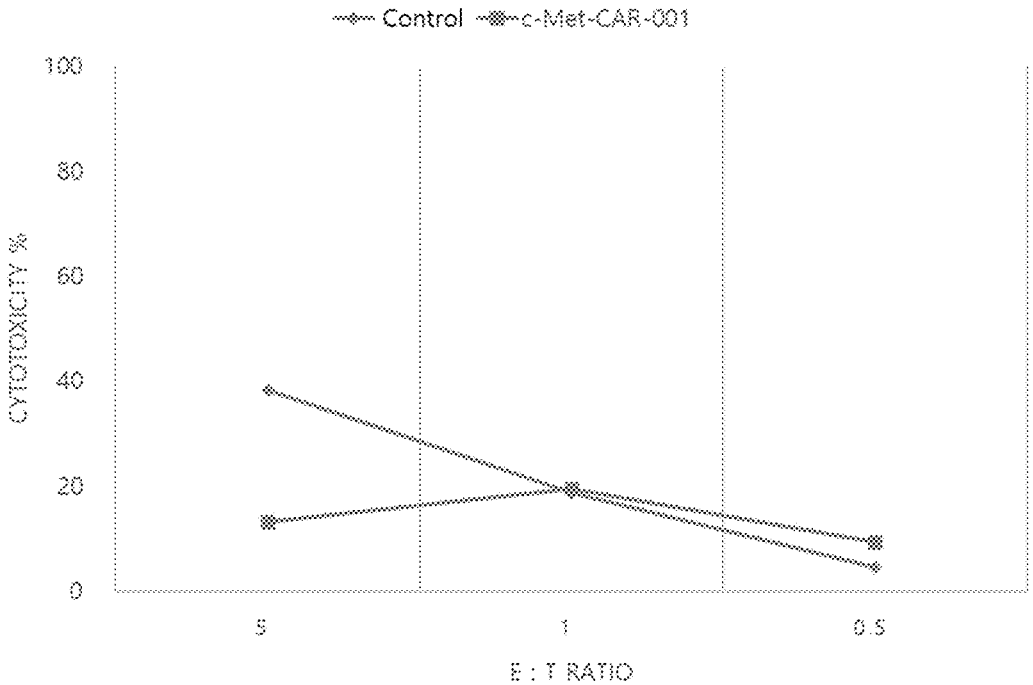

In the same assay manner, cytotoxicity against Jurkat was examined. T cells expressing c-Met-CAR-001, -002, -003, and -004 were observed to have almost no cytotoxicity against Jurkat, which expresses c-Met at a low level. Taken together, the data imply that anti-c-Met-CAR-expressing T cells exhibit specific cytotoxicity only for cells expressing high levels of c-Met (FIG. 21).

Although the preferred embodiments of the present disclosure have been disclosed for illustrative purposes, those skilled in the art will appreciate that various modifications, additions and substitutions are possible, without departing from the scope and spirit of the invention as disclosed in the accompanying claims.

This application contains references to amino acid sequences and/or nucleic acid sequences which have been submitted concurrently herewith as the sequence listing text file entitled "000302usnp_SequenceListing. TXT", file size 37 kilobytes (KB), created on 24 Mar. 2022. The aforementioned sequence listing is hereby incorporated by reference in its entirety pursuant to 37 C.F.R. § 1.52 (e) (5).

---

What is claimed is:

1. A nucleic acid molecule coding for an anti-c-Met chimeric antigen receptor, comprising:

a c-Met-binding domain, a transmembrane domain, and an intracellular signaling domain, wherein the c-Met-binding domain is an antibody or an antigen binding fragment thereof binding specifically to c-Met, wherein the antibody or the antigen binding fragment thereof comprises a heavy chain variable region (VH) consisting of the amino acid sequence of SEQ ID NO: 21; and a light chain variable region (VL) consisting of the amino acid sequence of SEQ ID NO: 22.

2. The nucleic acid molecule of claim 1, wherein the chimeric antigen receptor further comprises a leader sequence (LS).

3. The nucleic acid molecule of claim 2, wherein the leader sequence is a leader sequence of hCD8 alpha, a leader sequence of hGM-CSF receptor alpha-chain, or a leader sequence of 3E8 antibody.

4. The nucleic acid molecule of claim 2, wherein the leader sequence is a leader sequence comprising the amino acid sequence encoded by the nucleotide sequence of SEQ ID NO: 26, 28, or 30.

5. The nucleic acid molecule of claim 1, wherein the c-Met-binding domain is linked to the transmembrane domain by a hinge region, a spacer region, or a combination thereof.

6. The nucleic acid molecule of claim 5, wherein the hinge region and the spacer region is a hinge of IgG1, a hinge of IgG4, a hinge of IgD, a hinge of CD8 alpha, IgG1 CH3, an extracellular domain of CD28, or a combination thereof.

7. The nucleic acid molecule of claim 5, wherein the hinge region or the spacer region comprises the amino acid sequence encoded by the nucleotide sequence of 32, 34, 36, 38, 40, or 44.

8. The nucleic acid molecule of claim 1, wherein the chimeric antigen receptor comprises a transmembrane domain of a protein selected from the group consisting of a T-cell receptor, CD28, CD3, CD45, CD4, CD5, CD8, CD9, CD16, CD22, CD33, CD37, CD64, CD80, CD86, CD134, CD137, and CD154.

9. The nucleic acid molecule of claim 8, wherein the transmembrane domain comprises the amino acid sequence encoded by the nucleotide sequence of SEQ ID NO: 42, 46, or 47.

10. The nucleic acid molecule of claim 1, wherein the intracellular signaling domain comprises a signaling domain of CD3 zeta.

11. The nucleic acid molecule of claim 10, wherein the signaling domain of CD3 zeta comprises an amino acid sequence encoded by the nucleotide sequence of SEQ ID NO: 55, 57, or 59.

12. The nucleic acid molecule of claim 1, wherein the intracellular signaling domain further comprises as a costimulatory domain a signaling domain of a protein selected from the group consisting of OX40, CD2, CD27, CD28, CDS, ICAM-1, LFA-1 (CD11a/CD18), ICOS (CD278), and 4-1BB (CD137).

13. The nucleic acid molecule of claim 12, wherein the costimulatory domain comprises an amino acid sequence encoded by the nucleotide sequence of SEQ ID NO: 49, 51, or 53.

14. An anti-c-Met chimeric antigen receptor molecule comprising a polypeptide encoded by the nucleic acid molecule of claim 1.

15. An effector cell, having the anti-c-Met chimeric antigen receptor molecule of claim 14 expressed on a surface thereof.

16. The effector cell of claim 15, wherein the effector cell is selected from the group consisting of dendritic cells, killer dendritic cells, mast cells, natural killer cells, B lymphocytes, T lymphocytes, macrophages, and progenitor cells thereof.

\* \* \* \* \*

SEQUENCE LISTING

<160> NUMBER OF SEQ ID NOS: 66

<210> SEQ ID NO 1
<211> LENGTH: 27

```
<212> TYPE: DNA
<213> ORGANISM: Artificial Sequence
<220> FEATURE:
<223> OTHER INFORMATION: Primer: GMCSF rec.a LS+1E4-H4k2 scFv (F)

<400> SEQUENCE: 1
ctcctgatcc cacaggtgca gctggtg                                              27

<210> SEQ ID NO 2
<211> LENGTH: 27
<212> TYPE: DNA
<213> ORGANISM: Artificial Sequence
<220> FEATURE:
<223> OTHER INFORMATION: Primer: 1E4-H4k2 scFv +hCD28 pECD+hinge(R)

<400> SEQUENCE: 2
aattgcggcc gcacgtttga tttccac                                             27

<210> SEQ ID NO 3
<211> LENGTH: 27
<212> TYPE: DNA
<213> ORGANISM: Artificial Sequence
<220> FEATURE:
<223> OTHER INFORMATION: Primer: AS+BamHI+GMCSF rec.a LS(F)

<400> SEQUENCE: 3
cgggatccat gcttctcctg gtgacaa                                             27

<210> SEQ ID NO 4
<211> LENGTH: 27
<212> TYPE: DNA
<213> ORGANISM: Artificial Sequence
<220> FEATURE:
<223> OTHER INFORMATION: Primer: GMCSF rec.a LS+1E4-H4k2 scFv(R)

<400> SEQUENCE: 4
cagctgcacc tgtgggatca ggaggaa                                             27

<210> SEQ ID NO 5
<211> LENGTH: 27
<212> TYPE: DNA
<213> ORGANISM: Artificial Sequence
<220> FEATURE:
<223> OTHER INFORMATION: Primer: 1E4-H4k2 scFv+hinge+CD28 pECD(F)

<400> SEQUENCE: 5
gaaatcaaac gtgcggccgc aattgaa                                             27

<210> SEQ ID NO 6
<211> LENGTH: 28
<212> TYPE: DNA
<213> ORGANISM: Artificial Sequence
<220> FEATURE:
<223> OTHER INFORMATION: Primer: AS+Xho1+CD3-zeta (R)

<400> SEQUENCE: 6
ccgctcgagt tattagcgag ggggcagg                                            28

<210> SEQ ID NO 7
<211> LENGTH: 27
<212> TYPE: DNA
<213> ORGANISM: Artificial Sequence
<220> FEATURE:
<223> OTHER INFORMATION: Primer: 3E8 LS+1E4-H4k2 scFv(F)

<400> SEQUENCE: 7
```

-continued ggtgtccact cccaggtgca gctggtg                                                27

<210> SEQ ID NO 8
<211> LENGTH: 27
<212> TYPE: DNA
<213> ORGANISM: Artificial Sequence
<220> FEATURE:
<223> OTHER INFORMATION: Primer: 1E4-H4k2 scFv+hIgD hinge(R)

<400> SEQUENCE: 8
acctggccag cgacgtttga tttccac                                                27

<210> SEQ ID NO 9
<211> LENGTH: 24
<212> TYPE: DNA
<213> ORGANISM: Artificial Sequence
<220> FEATURE:
<223> OTHER INFORMATION: Primer: BamHI+3E8 VH(F)

<400> SEQUENCE: 9
ggatccatgg aatggagctg ggtc                                                   24

<210> SEQ ID NO 10
<211> LENGTH: 27
<212> TYPE: DNA
<213> ORGANISM: Artificial Sequence
<220> FEATURE:
<223> OTHER INFORMATION: Primer: 1E4-H4k2 scFv+3E8 LS(R)

<400> SEQUENCE: 10
cagctgcacc tgggagtgga cacctgt                                               27

<210> SEQ ID NO 11
<211> LENGTH: 27
<212> TYPE: DNA
<213> ORGANISM: Artificial Sequence
<220> FEATURE:
<223> OTHER INFORMATION: Primer: 1E4-H4k2 scFv+hIgD hinge(F)

<400> SEQUENCE: 11
gaaatcaaac gtcgctggcc aggttct                                               27

<210> SEQ ID NO 12
<211> LENGTH: 27
<212> TYPE: DNA
<213> ORGANISM: Artificial Sequence
<220> FEATURE:
<223> OTHER INFORMATION: Primer: XhoI+CD3zeta(R)

<400> SEQUENCE: 12
ccgctcgagt tagcgagggg gcagggc                                               27

<210> SEQ ID NO 13
<211> LENGTH: 19
<212> TYPE: DNA
<213> ORGANISM: Artificial Sequence
<220> FEATURE:
<223> OTHER INFORMATION: Primer: T7(F)

<400> SEQUENCE: 13
tatacgactc actataggg                                                        19

<210> SEQ ID NO 14
<211> LENGTH: 18
<212> TYPE: DNA
<213> ORGANISM: Artificial Sequence -continued
<220> FEATURE:
<223> OTHER INFORMATION: Primer: SP6(R)

<400> SEQUENCE: 14
atttaggtga cactatag                                                              18

<210> SEQ ID NO 15
<211> LENGTH: 5
<212> TYPE: PRT
<213> ORGANISM: Artificial Sequence
<220> FEATURE:
<223> OTHER INFORMATION: CDRH1 (AA)

<400> SEQUENCE: 15

Thr His Trp Ile Thr
1               5

<210> SEQ ID NO 16
<211> LENGTH: 17
<212> TYPE: PRT
<213> ORGANISM: Artificial Sequence
<220> FEATURE:
<223> OTHER INFORMATION: CDRH2 (AA)

<400> SEQUENCE: 16

Thr Ile Asp Pro Thr Asp Ser Tyr Asn Phe Tyr Gly Pro Ser Phe Gln
1               5                   10                  15

Gly

<210> SEQ ID NO 17
<211> LENGTH: 17
<212> TYPE: PRT
<213> ORGANISM: Artificial Sequence
<220> FEATURE:
<223> OTHER INFORMATION: CDRH3 (AA)

<400> SEQUENCE: 17

Asp Gly Asn Tyr Tyr Asp Ser Arg Gly Tyr Tyr Tyr Asp Thr Phe Asp
1               5                   10                  15

Met

<210> SEQ ID NO 18
<211> LENGTH: 11
<212> TYPE: PRT
<213> ORGANISM: Artificial Sequence
<220> FEATURE:
<223> OTHER INFORMATION: CDRL1 (AA)

<400> SEQUENCE: 18

Arg Ala Ser Gln Gly Ile Ser Thr Tyr Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: CDRL2 (AA)

<400> SEQUENCE: 19

Ser Ala Ser Thr Leu Glu Ser
1               5

<210> SEQ ID NO 20
<211> LENGTH: 9

```
<212> TYPE: PRT
<213> ORGANISM: Artificial Sequence
<220> FEATURE:
<223> OTHER INFORMATION: CDRL3 (AA)

<400> SEQUENCE: 20

Gln Gln Ala Asp Ser Phe Pro Leu Thr
1               5

<210> SEQ ID NO 21
<211> LENGTH: 126
<212> TYPE: PRT
<213> ORGANISM: Artificial Sequence
<220> FEATURE:
<223> OTHER INFORMATION: 1E4-H4k2 heavy chain variable region (AA)

<400> SEQUENCE: 21

Gln Val Gln Leu Val Gln Ser Gly Ala Glu Val Lys Lys Pro Gly Ser
1               5                   10                  15

Ser Val Lys Val Ser Cys Gln Gly Ser Gly Tyr Ser Phe Pro Thr His
            20                  25                  30

Trp Ile Thr Trp Val Arg Gln Ala Pro Gly Gln Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly Arg Val Thr Ile Thr Ala Asp Ser Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Asp Gly Asn Tyr Tyr Asp Ser Arg Gly Tyr Tyr Tyr Asp Thr
                100                 105                 110

Phe Asp Met Trp Gly Gln Gly Thr Leu Val Thr Val Ser Ser
        115                 120                 125

<210> SEQ ID NO 22
<211> LENGTH: 107
<212> TYPE: PRT
<213> ORGANISM: Artificial Sequence
<220> FEATURE:
<223> OTHER INFORMATION: 1E4-H4k2 light chain variable region (AA)

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Lys Ala Pro Lys Leu Leu Ile
        35                  40                  45

Tyr Ser Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Pro Leu
                85                  90                  95

Thr Phe Gly Gly Gly Thr Lys Val Glu Ile Lys
            100                 105

<210> SEQ ID NO 23
<211> LENGTH: 249
<212> TYPE: PRT
```

-continued

```
<213> ORGANISM: Artificial Sequence
<220> FEATURE:
<223> OTHER INFORMATION: 1E4-H4k2 scFv (AA)

<400> SEQUENCE: 23

Gln Val Gln Leu Val Gln Ser Gly Ala Glu Val Lys Lys Pro Gly Ser
1               5                   10                  15

Ser Val Lys Val Ser Cys Gln Gly Ser Gly Tyr Ser Phe Pro Thr His
                20                  25                  30

Trp Ile Thr Trp Val Arg Gln Ala Pro Gly Gln Gly Leu Glu Trp Met
            35                  40                  45

Gly Thr Ile Asp Pro Thr Asp Ser Tyr Asn Phe Tyr Gly Pro Ser Phe
        50                  55                  60

Gln Gly Arg Val Thr Ile Thr Ala Asp Ser Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Val Thr Val Ser Ser Gly Gly
            115                 120                 125

Gly Gly Ser Gly Gly Gly Gly Ser Gly Gly Gly Gly Ser Asp Ile Gln
        130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Gly Ile Ser Thr Tyr Leu Ala Trp
            165                 170                 175

Tyr Gln Gln Lys Pro Gly Lys Ala Pro Lys Leu Leu Ile Tyr Ser Ala
            180                 185                 190

Ser Thr Leu Glu Ser Gly Val Pro Ser Arg Phe Ser Gly Ser Gly Ser
            195                 200                 205

Gly Thr Asp Phe Thr Leu Thr Ile Ser Ser Leu Gln Pro Glu Asp Phe
        210                 215                 220

Ala Thr Tyr Tyr Cys Gln Gln Ala Asp Ser Phe Pro Leu Thr Phe Gly
225                 230                 235                 240

Gly Gly Thr Lys Val Glu Ile Lys Arg
                245

<210> SEQ ID NO 24
<211> LENGTH: 747
<212> TYPE: DNA
<213> ORGANISM: Artificial Sequence
<220> FEATURE:
<223> OTHER INFORMATION: 1E4-H4k2 scFv (NA)

<400> SEQUENCE: 24
caggtgcagc tggtgcagtc tggcgccgaa gtgaagaagc ccggctcctc cgtgaaggtc      60
tcctgccagg gctccggcta ctccttcccc acccactgga tcacctgggt cgcacaggcc     120
cccggccaag gcctggaatg gatgggcacc atcgacccca ccgactccta caacttctac     180
ggccccagct ccagggcag agtgaccatc accgccgact cctccacgtc caccgcctac     240
atggagctgt cctccctgag atctgaggac accgccatgt actactgcgc cagggacggc     300
aactactacg actcccgggg ctactactac gatccttcg acatgtgggg ccagggcacc      360
ctggtcaccg tctcctcagg cggtggagga tctggaggag cggctctgg ggggggcggc      420 tctgacatcc agatgaccca gtcccccagc tccctgtccg cctccgtggg cgacagagtg     480
```

-continued

```
accatcacct gtcgggcctc ccagggcatc tccacctacc tggcctggta tcagcagaag      540
cccggcaaag cccccaagct gctgatctac tccgcctcca ccctggaatc cggcgtgccc      600
tccagattct ccggctccgg ctctggcacc gacttcaccc tgaccatctc cagcctgcag      660
cccgaggact ttgccaccta ctactgccag caggccgact ccttccccct gaccttcggc      720
ggaggcacca aggtggaaat caaacgt                                         747
```

```
<210> SEQ ID NO 25
<211> LENGTH: 22
<212> TYPE: PRT
<213> ORGANISM: Artificial Sequence
<220> FEATURE:
<223> OTHER INFORMATION: hGM-CSF rec.a LS (AA)

<400> SEQUENCE: 25

Met Leu Leu Leu Val Thr Ser Leu Leu Leu Cys Glu Leu Pro His Pro
1               5                   10                  15

Ala Phe Leu Leu Ile Pro
            20
```

```
<210> SEQ ID NO 26
<211> LENGTH: 66
<212> TYPE: DNA
<213> ORGANISM: Artificial Sequence
<220> FEATURE:
<223> OTHER INFORMATION: hGM-CSF rec.a LS (NA)

<400> SEQUENCE: 26
atgcttctcc tggtgacaag ccttctgctc tgtgagttac cacacccagc attcctcctg      60
atccca                                                                66
```

```
<210> SEQ ID NO 27
<211> LENGTH: 21
<212> TYPE: PRT
<213> ORGANISM: Artificial Sequence
<220> FEATURE:
<223> OTHER INFORMATION: hCD8a LS (AA)

<400> SEQUENCE: 27

Met Ala Leu Pro Val Thr Ala Leu Leu Leu Pro Leu Ala Leu Leu Leu
1               5                   10                  15

His Ala Ala Arg Pro
            20
```

```
<210> SEQ ID NO 28
<211> LENGTH: 63
<212> TYPE: DNA
<213> ORGANISM: Artificial Sequence
<220> FEATURE:
<223> OTHER INFORMATION: hCD8a LS (NA)

<400> SEQUENCE: 28
atggccctcc ctgtcaccgc cctgctgctt ccgctggctc ttctgctcca cgccgctcgg      60
ccc                                                                   63
```

```
<210> SEQ ID NO 29
<211> LENGTH: 19
<212> TYPE: PRT
<213> ORGANISM: Artificial Sequence
<220> FEATURE:
<223> OTHER INFORMATION: 3E8 LS (AA)
```

<400> SEQUENCE: 29

Met Glu Trp Ser Trp Val Phe Leu Phe Phe Leu Ser Val Thr Thr Gly
1               5                   10                  15

Val His Ser

<210> SEQ ID NO 30
<211> LENGTH: 57
<212> TYPE: DNA
<213> ORGANISM: Artificial Sequence
<220> FEATURE:
<223> OTHER INFORMATION: 3E8 LS (NA)

<400> SEQUENCE: 30
atggaatgga gctgggtctt tctcttcttc ctgtcagtaa ctacaggtgt ccactcc          57

<210> SEQ ID NO 31
<211> LENGTH: 3
<212> TYPE: PRT
<213> ORGANISM: Artificial Sequence
<220> FEATURE:
<223> OTHER INFORMATION: Hinge (AA)

<400> SEQUENCE: 31

Ala Ala Ala
1

<210> SEQ ID NO 32
<211> LENGTH: 9
<212> TYPE: DNA
<213> ORGANISM: Artificial Sequence
<220> FEATURE:
<223> OTHER INFORMATION: Hinge (NA)

<400> SEQUENCE: 32 gcggccgca                                                                9

<210> SEQ ID NO 33
<211> LENGTH: 15
<212> TYPE: PRT
<213> ORGANISM: Artificial Sequence
<220> FEATURE:
<223> OTHER INFORMATION: hIgG1 hinge (AA)

<400> SEQUENCE: 33

Glu Pro Lys Ser Cys Asp Lys Thr His Thr Cys Pro Pro Cys Pro
1               5                   10                  15

<210> SEQ ID NO 34
<211> LENGTH: 45
<212> TYPE: DNA
<213> ORGANISM: Artificial Sequence
<220> FEATURE:
<223> OTHER INFORMATION: hIgG1 hinge (NA)

<400> SEQUENCE: 34
gagcccaaat cttgtgacaa aactcacaca tgcccaccgt gccca                       45

<210> SEQ ID NO 35
<211> LENGTH: 64
<212> TYPE: PRT
<213> ORGANISM: Artificial Sequence
<220> FEATURE:
<223> OTHER INFORMATION: hIgD hinge (AA)

<400> SEQUENCE: 35

-continued

```
Arg Trp Pro Gly Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Gly Cys Pro
    50                  55                  60
```

<210> SEQ ID NO 36
<211> LENGTH: 192
<212> TYPE: DNA
<213> ORGANISM: Artificial Sequence
<220> FEATURE:
<223> OTHER INFORMATION: hIgD hinge (NA)

<400> SEQUENCE: 36

```
cgctggccag gttctccaaa ggcacaggcc tcctccgtgc ccactgcaca accccaagca     60
gagggcagcc tcgccaaggc aaccacagcc ccagccacca cccgtaacac aggtagagga    120
ggagaagaga agaagaagga gaaggagaaa gaggaacaag aagagagaga gacaaagaca    180
ccaggttgtc cg                                                        192
```

<210> SEQ ID NO 37
<211> LENGTH: 107
<212> TYPE: PRT
<213> ORGANISM: Artificial Sequence
<220> FEATURE:
<223> OTHER INFORMATION: hIgG1 CH3 (AA)

<400> SEQUENCE: 37

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 38
<211> LENGTH: 321
<212> TYPE: DNA
<213> ORGANISM: Artificial Sequence
<220> FEATURE:
<223> OTHER INFORMATION: hIgG1 CH3 (NA)

<400> SEQUENCE: 38

```
gggcagcccc gagaaccaca ggtgtacacc ctgcccccat cccgggatga gctgaccaag     60
aaccaggtca gcctgacctg cctggtcaaa ggcttctatc ccagcgacat cgccgtggag    120
tgggagagca atgggcagcc ggagaacaac tacaagacca cgcctcccgt gctggactcc    180
gacggctcct tcttcctcta cagcaagctc accgtggaca gagcaggtg gcagcagggg     240
```

-continued aacgtcttct catgctccgt gatgcatgag gctctgcaca accactacac gcagaagagc          300
ctctccctgt ctccgggtaa a                                                    321

<210> SEQ ID NO 39
<211> LENGTH: 45
<212> TYPE: PRT
<213> ORGANISM: Artificial Sequence
<220> FEATURE:
<223> OTHER INFORMATION: hCD8a hinge (AA)

<400> SEQUENCE: 39

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 40
<211> LENGTH: 135
<212> TYPE: DNA
<213> ORGANISM: Artificial Sequence
<220> FEATURE:
<223> OTHER INFORMATION: hCD8a hinge (NA)

<400> SEQUENCE: 40
accactaccc cagcaccgag gccacccacc ccggctccta ccatcgcctc ccagcctctg          60
tccctgcgtc cggaggcatg tagacccgca gctggtgggg ccgtgcatac ccggggtctt         120
gacttcgcct gcgat                                                          135

<210> SEQ ID NO 41
<211> LENGTH: 24
<212> TYPE: PRT
<213> ORGANISM: Artificial Sequence
<220> FEATURE:
<223> OTHER INFORMATION: hCD8a TM (AA)

<400> SEQUENCE: 41

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 42
<211> LENGTH: 72
<212> TYPE: DNA
<213> ORGANISM: Artificial Sequence
<220> FEATURE:
<223> OTHER INFORMATION: hCD8a TM (NA)

<400> SEQUENCE: 42
atctacattt gggcccctct ggctggtact tgcggggtcc tgctgctttc actcgtgatc          60
actctttact gt                                                              72

<210> SEQ ID NO 43
<211> LENGTH: 39
<212> TYPE: PRT
<213> ORGANISM: Artificial Sequence
<220> FEATURE:
<223> OTHER INFORMATION: hCD28 pECD (AA)

<400> SEQUENCE: 43

-continued

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 44
<211> LENGTH: 117
<212> TYPE: DNA
<213> ORGANISM: Artificial Sequence
<220> FEATURE:
<223> OTHER INFORMATION: hCD28 pECD (NA)

<400> SEQUENCE: 44
attgaagtta tgtatcctcc tccttaccta gacaatgaga agagcaatgg aaccattatc      60
catgtgaaag ggaaacacct tgtccaagt cccctatttc ccggaccttc taagccc       117

<210> SEQ ID NO 45
<211> LENGTH: 27
<212> TYPE: PRT
<213> ORGANISM: Artificial Sequence
<220> FEATURE:
<223> OTHER INFORMATION: hCD28 TM (AA)

<400> SEQUENCE: 45

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 46
<211> LENGTH: 81
<212> TYPE: DNA
<213> ORGANISM: Artificial Sequence
<220> FEATURE:
<223> OTHER INFORMATION: hCD28 TM (NA)

<400> SEQUENCE: 46
ttttgggtgc tggtggtggt tgggggagtc ctggcttgct atagcttgct agtaacagtg      60
gcctttatta ttttctgggt g                                                81

<210> SEQ ID NO 47
<211> LENGTH: 81
<212> TYPE: DNA
<213> ORGANISM: Artificial Sequence
<220> FEATURE:
<223> OTHER INFORMATION: hCD28 TM (NA)

<400> SEQUENCE: 47
ttttgggtgc tggtggtggt tggtggagtc ctggcttgct atagcttgct agtaacagtg      60
gcctttatta ttttctgggt g                                                81

<210> SEQ ID NO 48
<211> LENGTH: 42
<212> TYPE: PRT
<213> ORGANISM: Artificial Sequence
<220> FEATURE:
<223> OTHER INFORMATION: h4-1BB (AA)

<400> SEQUENCE: 48

Lys Arg Gly Arg Lys Lys Leu Leu Tyr Ile Phe Lys Gln Pro Phe Met
1               5                   10                  15
```

Arg Pro Val Gln Thr Thr Gln Glu Glu Asp Gly Cys Ser Cys Arg Phe
          20              25              30

Pro Glu Glu Glu Glu Gly Gly Cys Glu Leu
          35              40

<210> SEQ ID NO 49
<211> LENGTH: 126
<212> TYPE: DNA
<213> ORGANISM: Artificial Sequence
<220> FEATURE:
<223> OTHER INFORMATION: h4-1BB (NA)

<400> SEQUENCE: 49
aagcgcggtc ggaagaagct gctgtacatc tttaagcaac ccttcatgag gcctgtgcag      60
actactcaag aggaggacgg ctgttcatgc cggttcccag aggaggagga aggcggctgc     120
gaactg                                                                 126

<210> SEQ ID NO 50
<211> LENGTH: 41
<212> TYPE: PRT
<213> ORGANISM: Artificial Sequence
<220> FEATURE:
<223> OTHER INFORMATION: hCD28 ICD (AA)

<400> SEQUENCE: 50

Arg Ser Lys Arg Ser Arg Leu Leu His Ser Asp Tyr Met Asn Met Thr
1               5               10              15

Pro Arg Arg Pro Gly Pro Thr Arg Lys His Tyr Gln Pro Tyr Ala Pro
          20              25              30

Pro Arg Asp Phe Ala Ala Tyr Arg Ser
          35              40

<210> SEQ ID NO 51
<211> LENGTH: 123
<212> TYPE: DNA
<213> ORGANISM: Artificial Sequence
<220> FEATURE:
<223> OTHER INFORMATION: hCD28 ICD (NA)

<400> SEQUENCE: 51
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                    123

<210> SEQ ID NO 52
<211> LENGTH: 42
<212> TYPE: PRT
<213> ORGANISM: Artificial Sequence
<220> FEATURE:
<223> OTHER INFORMATION: hOX-40 (AA)

<400> SEQUENCE: 52

Ala Leu Tyr Leu Leu Arg Arg Asp Gln Arg Leu Pro Pro Asp Ala His
1               5               10              15

Lys Pro Pro Gly Gly Gly Ser Phe Arg Thr Pro Ile Gln Glu Glu Gln
          20              25              30

Ala Asp Ala His Ser Thr Leu Ala Lys Ile
          35              40

<210> SEQ ID NO 53

```
<211> LENGTH: 126
<212> TYPE: DNA
<213> ORGANISM: Artificial Sequence
<220> FEATURE:
<223> OTHER INFORMATION: hOX-40 (NA)

<400> SEQUENCE: 53
gccctgtacc tgctccggag ggaccagagg ctgccccccg atgcccacaa gccccctggg      60
ggaggcagtt tccggacccc catccaagag gagcaggccg acgcccactc caccctggcc     120
aagatc                                                               126

<210> SEQ ID NO 54
<211> LENGTH: 112
<212> TYPE: PRT
<213> ORGANISM: Artificial Sequence
<220> FEATURE:
<223> OTHER INFORMATION: hCD3z iso2M (AA)

<400> SEQUENCE: 54

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 55
<211> LENGTH: 336
<212> TYPE: DNA
<213> ORGANISM: Artificial Sequence
<220> FEATURE:
<223> OTHER INFORMATION: hCD3z iso2M (NA)

<400> SEQUENCE: 55
cgcgtgaaat tcagccgcag cgcagatgct ccagcctaca gcaggggca gaaccagctc       60 tacaacgaac tcaatcttgg tcggagagag gagtacgacg tgctggacaa gcggagagga     120
cgggacccag aaatgggcgg gaagccgcgc agaaagaatc cccaagaggg cctgtacaac     180
gagctccaaa aggataagat ggcagaagcc tatagcgaga ttggtatgaa aggggaacgc     240
agaagaggca aaggccacga cggactgtac cagggactca gcaccgccac caaggacacc     300
tatgacgctc ttcacatgca ggccctgccg cctcgg                              336

<210> SEQ ID NO 56
<211> LENGTH: 112
<212> TYPE: PRT
<213> ORGANISM: Artificial Sequence
<220> FEATURE:
<223> OTHER INFORMATION: hCD3z iso2 (AA)

<400> SEQUENCE: 56

Arg Val Lys Phe Ser Arg Ser Ala Asp Ala Pro Ala Tyr Gln Gln Gly
1               5                   10                  15
```

```
Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 57
<211> LENGTH: 336
<212> TYPE: DNA
<213> ORGANISM: Artificial Sequence
<220> FEATURE:
<223> OTHER INFORMATION: hCD3z iso2 (NA)

<400> SEQUENCE: 57

```
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat     180
gaactgcaga agataagat ggcggaggcc tacagtgaga ttgggatgaa aggcgagcgc     240
cggaggggca aggggcacga tggcctttac caggtctca gtacagccac caaggacacc      300
tacgacgccc ttcacatgca ggccctgccc cctcgc                                336
```

<210> SEQ ID NO 58
<211> LENGTH: 113
<212> TYPE: PRT
<213> ORGANISM: Artificial Sequence
<220> FEATURE:
<223> OTHER INFORMATION: hCD3z iso1 (AA)

<400> SEQUENCE: 58

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
        50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

<210> SEQ ID NO 59
<211> LENGTH: 339
<212> TYPE: DNA
<213> ORGANISM: Artificial Sequence

```
<220> FEATURE:
<223> OTHER INFORMATION: hCD3z iso1 (NA)

<400> SEQUENCE: 59
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgcag agaaggaaga accctcagga aggcctgtac     180
aatgaactgc agaaagataa gatggcggag gcctacagtg agattgggat gaaaggcgag     240
cgccggaggg gcaagggggca cgatggcctt taccagggtc tcagtacagc caccaaggac    300
acctacgacg cccttcacat gcaggccctg cccctcgc                            339

<210> SEQ ID NO 60
<211> LENGTH: 1479
<212> TYPE: DNA
<213> ORGANISM: Artificial Sequence
<220> FEATURE:
<223> OTHER INFORMATION: c-Met-CAR-001 (NA)

<400> SEQUENCE: 60
atggccctcc ctgtcaccgc cctgctgctt ccgctggctc ttctgctcca cgccgctcgg      60
ccccaggtgc agctggtgca gtctggcgcc gaagtgaaga gcccggctc ctccgtgaag       120 gtctcctgcc agggctccgg ctactccttc cccaccact ggatcacctg ggtgcgacag       180
gcccccggcc aaggcctgga atggatgggc accatcgacc ccaccgactc ctacaacttc      240
tacggcccca gcttccaggg cagagtgacc atcaccgccg actcctccac gtccaccgcc      300
tacatggagc tgtcctccct gagatctgag gacaccgcca tgtactactg cgccagggac      360
ggcaactact acgactcccg gggctactac tacgatacct cgacatgtg gggccagggc       420 accctggtca ccgtctcctc aggcggtgga ggatctggag gaggcggctc tggggggggc      480
ggctctgaca tccagatgac ccagtccccc agctccctgt ccgcctccgt gggcgacaga      540
gtgaccatca cctgtcgggc ctcccagggc atctccacct acctggcctg gtatcagcag      600
aagcccggca agcccccaa gctgctgatc tactccgcct ccaccctgga atccggcgtg       660
ccctccagat tctccggctc cggctctggc accgacttca ccctgaccat ctccagcctg      720
cagcccgagg actttgccac ctactactgc cagcaggccg actccttccc cctgaccttc      780
ggcggaggca ccaaggtgga aatcaaacgt accactaccc cagcaccgag gccacccacc      840
ccggctccta ccatcgcctc ccagcctctg tccctgcgtc cggaggcatg tagacccgca      900
gctggtgggg ccgtgcatac ccggggtctt gacttcgcct gcgatatcta catttgggcc      960
cctctggctg gtacttgcgg ggtcctgctg ctttcactcg tgatcactct ttactgtaag     1020
cgcggtcgga gaagctgct gtacatcttt aagcaaccct catgaggcc tgtgcagact        1080 actcaagagg aggacggctg ttcatgccgg ttcccagagg aggaggaagg cggctgcgaa     1140
ctgcgcgtga aattcagccg cagcgcagat gctccagcct acaagcaggg gcagaaccag     1200
ctctacaacg aactcaatct tggtcggaga gaggagtacg acgtgctgga caagcggaga     1260
ggacgggacc cagaaatggg cgggaagccg cgcagaaaga tcccccaaga gggcctgtac     1320
aacgagctcc aaaaggataa gatggcagaa gcctatagcg agattggtat gaaaggggaa     1380
cgcagaagag gcaaaggcca cgacggactg taccaggac tcagcaccgc caccaaggac       1440
acctatgacg ctcttcacat gcaggccctg ccgcctcgg                           1479

<210> SEQ ID NO 61
```

```
<211> LENGTH: 1479
<212> TYPE: DNA
<213> ORGANISM: Artificial Sequence
<220> FEATURE:
<223> OTHER INFORMATION: c-Met-CAR-002 (NA)

<400> SEQUENCE: 61
atgcttctcc tggtgacaag ccttctgctc tgtgagttac cacacccagc attcctcctg        60
atcccacagg tgcagctggt gcagtctggc gccgaagtga agaagcccgg ctcctccgtg       120
aaggtctcct gccagggctc cggctactcc ttccccaccc actggatcac ctgggtgcga       180
caggcccccg gccaaggcct ggaatggatg ggcaccatcg accccaccga ctcctacaac       240
ttctacggcc ccagcttcca gggcagagtg accatcaccg ccgactcctc cacgtccacc       300
gcctacatgg agctgtcctc cctgagatct gaggacaccg ccatgtacta ctgcgccagg       360
gacggcaact actacgactc ccggggctac tactacgata ccttcgacat gtggggccag       420
ggcaccctgg tcaccgtctc ctcaggcggt ggaggatctg aggaggcggg ctctgggggg       480
ggcggctctg acatccagat gacccagtcc cccagctccc tgtccgcctc cgtgggcgac       540
agagtgacca tcacctgtcg ggcctcccag ggcatctcca cctacctggc ctggtatcag       600
cagaagcccg gcaaagcccc caagctgctg atctactccg cctccaccct ggaatccggc       660
gtgccctcca gattctccgg ctccggctct ggcaccgact caccctgac catctccagc        720 ctgcagcccg aggactttgc cacctactac tgccagcagg ccgactcctt cccccctgacc      780 ttcggcggag gcaccaaggt ggaaatcaaa cgtgcggccg caattgaagt tatgtatcct       840
cctccttacc tagacaatga gaagagcaat ggaaccatta tccatgtgaa agggaaacac       900
ctttgtccaa gtcccctatt tcccggacct tctaagccct tttgggtgct ggtggtggtt       960
gggggagtcc tggcttgcta tagcttgcta gtaacagtgg cctttattat tttctgggtg      1020
aggagtaaga ggagcaggct cctgcacagt gactacatga acatgactcc ccgccgcccc      1080
gggcccaccc gcaagcatta ccagccctat gccccaccac gcgacttcgc agcctatcgc      1140
tccagagtga agttcagcag gagcgcagac gccccgcgt accagcaggg ccagaaccag       1200
ctctataacg agctcaatct aggacgaaga gaggagtacg atgtttttgga caagagacgt      1260 ggccgggacc ctgagatggg gggaaagccg agaaggaaga accctcagga aggcctgtac      1320
aatgaactgc agaaagataa gatggcggag gcctacagtg agattgggat gaaaggcgag      1380
cgccggaggg gcaagggcca cgatggcctt taccagggtc tcagtacagc caccaaggac      1440
acctacgacg cccttcacat gcaggccctg ccccctcgc                             1479

<210> SEQ ID NO 62
<211> LENGTH: 2031
<212> TYPE: DNA
<213> ORGANISM: Artificial Sequence
<220> FEATURE:
<223> OTHER INFORMATION: c-Met-CAR-003 (NA)

<400> SEQUENCE: 62
atggaatgga gctgggtctt tctcttcttc ctgtcagtaa ctacaggtgt ccactcccag        60
gtgcagctgg tgcagtctgg cgccgaagtg aagaagcccg gctcctccgt gaaggtctcc       120
tgccagggct ccggctactc cttccccacc cactggatca cctgggtgcg acaggccccc       180
ggccaaggcc tggaatggat gggcaccatc gaccccaccg actcctacaa cttctacggc       240
cccagcttcc agggcagagt gaccatcacc gccgactcct ccacgtccac cgcctacatg       300
gagctgtcct ccctgagatc tgaggacacc gccatgtact actgcgccag ggacggcaac       360
```

-continued

```
tactacgact cccggggcta ctactacgat accttcgaca tgtggggcca gggcaccctg       420
gtcaccgtct cctcaggcgg tggaggatct ggaggaggcg gctctggggg gggcggctct       480
gacatccaga tgacccagtc ccccagctcc ctgtccgcct ccgtgggcga cagagtgacc       540
atcacctgtc gggcctccca gggcatctcc acctacctgg cctggtatca gcagaagccc       600
ggcaaagccc ccaagctgct gatctactcc gcctccaccc tggaatccgg cgtgccctcc       660
agattctccg gctccggctc tggcaccgac ttcaccctga ccatctccag cctgcagccc       720
gaggactttg ccacctacta ctgccagcag gccgactcct cccccctgac cttcggcgga       780
ggcaccaagg tggaaatcaa acgtcgctgg ccaggttctc caaaggcaca ggcctcctcc       840
gtgcccactg cacaacccca agcagagggc agcctcgcca aggcaaccac agccccagcc       900
accacccgta acacaggtag aggaggagaa gagaagaaga aggagaagga gaaagaggaa       960
caagaagaga gagacaaa gacaccaggt tgtccggagc ccaaatcttg tgacaaaact      1020
cacacatgcc caccgtgccc agggcagccc cgagaaccac aggtgtacac cctgcccccca     1080 tcccgggatg agctgaccaa gaaccaggtc agcctgacct gcctggtcaa aggcttctat      1140
cccagcgaca tcgccgtgga gtgggagagc aatgggcagc cggagaacaa ctacaagacc      1200
acgcctcccg tgctggactc cgacggctcc ttcttcctct acagcaagct caccgtggac      1260
aagagcaggt ggcagcaggg gaacgtcttc tcatgctccg tgatgcatga ggctctgcac      1320
aaccactaca cgcagaagag cctctccctg tctccgggta aattttgggt gctggtggtg      1380
gttggtggag tcctggcttg ctatagcttg ctagtaacag tggcctttat tattttctgg      1440
gtgaggagta agaggagcag gctcctgcac agtgactaca tgaacatgac tccccgccgc      1500
cccgggccca cccgcaagca ttaccagccc tatgccccac cacgcgactt cgcagcctat      1560
cgctccgccc tgtacctgct ccggagggac cagaggctgc cccccgatgc ccacaagccc      1620
cctgggggag gcagtttccg gacccccatc aagaggagc aggccgacgc ccactccacc      1680
ctggccaaga tcagagtgaa gttcagcagg agcgcagacg cccccgcgta ccagcagggc      1740
cagaaccagc tctataacga gctcaatcta ggacgaagag aggagtacga tgttttggac      1800
aagagacgtg gccgggaccc tgagatgggg ggaaagccgc agagaaggaa gaaccctcag      1860
gaaggcctgt acaatgaact gcagaaagat aagatggcgg aggcctacag tgagattggg      1920
atgaaaggcg agcgccggag gggcaagggg cacgatggcc tttaccaggg tctcagtaca      1980
gccaccaagg acacctacga cgcccttcac atgcaggccc tgcccccctcg c            2031
```

<210> SEQ ID NO 63
<211> LENGTH: 1665
<212> TYPE: DNA
<213> ORGANISM: Artificial Sequence
<220> FEATURE:
<223> OTHER INFORMATION: c-Met-CAR-004 (NA)

<400> SEQUENCE: 63

```
atggaatgga gctgggtctt tctcttcttc ctgtcagtaa ctacaggtgt ccactcccag        60
gtgcagctgg tgcagtctgg cgccgaagtg aagaagcccg gctcctccgt gaaggtctcc       120
tgccagggct ccggctactc cttccccacc cactggatca cctgggtgcg acaggccccc       180
ggccaaggcc tggaatggat gggcaccatc gaccccaccg actcctacaa cttctacggc       240
cccagcttcc agggcagagt gaccatcacc gccgactcct ccacgtccac cgcctacatg       300
gagctgtcct ccctgagatc tgaggacacc gccatgtact actgcgccag ggacggcaac       360
```

-continued

```
tactacgact cccggggcta ctactacgat accttcgaca tgtggggcca gggcaccctg      420
gtcaccgtct cctcaggcgg tggaggatct ggaggaggcg gctctggggg gggcggctct      480
gacatccaga tgacccagtc ccccagctcc ctgtccgcct ccgtgggcga cagagtgacc      540
atcacctgtc gggcctccca gggcatctcc acctacctgg cctggtatca gcagaagccc      600
ggcaaagccc ccaagctgct gatctactcc gcctccaccc tggaatccgg cgtgccctcc      660
agattctccg gctccggctc tggcaccgac ttcaccctga ccatctccag cctgcagccc      720
gaggactttg ccacctacta ctgccagcag gccgactcct cccccctgac cttcggcgga      780
ggcaccaagg tggaaatcaa acgtcgctgg ccaggttctc aaaggcaca  ggcctcctcc      840 gtgcccactg cacaacccca agcagagggc agcctcgcca aggcaaccac agccccagcc      900
accacccgta acacaggtag aggagggaaa gagaagaaga aggagaagga gaaagaggaa      960
caagaagaga gagagacaaa gacaccaggt tgtccgtttt gggtgctggt ggtggttggt     1020
ggagtcctgg cttgctatag cttgctagta acagtggcct ttattatttt ctgggtgagg     1080
agtaagagga gcaggctcct gcacagtgac tacatgaaca tgactccccg ccgcccc ggg     1140 cccacccgca agcattacca gccctatgcc ccaccacgcg acttcgcagc ctatcgctcc     1200
gccctgtacc tgctccggag ggaccagagg ctgcccccccg atgcccacaa gcccctgggg     1260
ggaggcagtt ccggaccccc catccaagag gagcaggccg acgcccactc caccctggcc     1320
aagatcagag tgaagttcag caggagcgca gacgcccccg cgtaccagca gggccagaac     1380
cagctctata cgagctcaa  tctaggacga agagaggagt acgatgtttt ggacaagaga     1440
cgtggccggg accctgagat ggggggaaag ccgcagagaa ggaagaaccc tcaggaaggc     1500
ctgtacaatg aactgcagaa agataagatg gcggaggcct acagtgagat tgggatgaaa     1560
ggcgagcgcc ggaggggcaa ggggcacgat ggcctttacc agggtctcag tacagccacc     1620
aaggacacct acgacgccct tcacatgcag gccctgcccc ctcgc                      1665
```

<210> SEQ ID NO 64
<211> LENGTH: 126
<212> TYPE: PRT
<213> ORGANISM: Artificial Sequence
<220> FEATURE:
<223> OTHER INFORMATION: 1E4-H5k2 heavy chain variable region (AA)

<400> SEQUENCE: 64

```
Gln Val Gln Leu Val Gln Ser Gly Ala Glu Val Lys Lys Pro Gly Ser
1               5                   10                  15

Ser Val Lys Val Ser Cys Gln Gly Ser Gly Tyr Ser Phe Pro Thr His
            20                  25                  30

Trp Ile Thr Trp Val Arg Gln Ala Pro Gly Gln Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly Arg Val Thr Ile Thr Ala Asp Ser Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Val Thr Val Ser Ser
        115                 120                 125
```

```
<210> SEQ ID NO 65
<211> LENGTH: 126
<212> TYPE: PRT
<213> ORGANISM: Artificial Sequence
<220> FEATURE:
<223> OTHER INFORMATION: 1E4-H6k2 heavy chain variable region (AA)

<400> SEQUENCE: 65

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Pro Thr His
            20                  25                  30

Trp Ile Thr Trp Val Arg Gln Ala Pro Gly Gln Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Val Thr Val Ser Ser
            115                 120                 125

<210> SEQ ID NO 66
<211> LENGTH: 107
<212> TYPE: PRT
<213> ORGANISM: Artificial Sequence
<220> FEATURE:
<223> OTHER INFORMATION: 1E4-H6k0 light chain variable region (AA)

<400> SEQUENCE: 66

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Thr Ala Pro Lys Leu Leu Ile
        35                  40                  45

Tyr Ser Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ala Asp Ser Phe Pro Leu
                85                  90                  95

Thr Phe Gly Gly Gly Thr Lys Val Glu Ile Lys
            100                 105
```